United States Patent
Offermanns et al.

(10) Patent No.: US 9,198,966 B2
(45) Date of Patent: Dec. 1, 2015

(54) B-TYPE PLEXIN ANTAGONISTS AND USES THEREOF

(75) Inventors: Stefan Offermanns, Bad Nauheim (DE); Jakub Swiercz, Bad Nauheim (DE); Thomas Worzfeld, Bad Nauheim (DE)

(73) Assignees: Ruprecht-Karls-Universität Heidelberg, Heidelberg (DE); Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 13/983,715

(22) PCT Filed: Feb. 9, 2012

(86) PCT No.: PCT/EP2012/052238
§ 371 (c)(1),
(2), (4) Date: Oct. 21, 2013

(87) PCT Pub. No.: WO2012/107531
PCT Pub. Date: Aug. 16, 2012

(65) Prior Publication Data
US 2014/0044741 A1 Feb. 13, 2014

(30) Foreign Application Priority Data
Feb. 9, 2011 (EP) .................................. 11153784

(51) Int. Cl.
| | | |
|---|---|---|
| *A61K 48/00* | (2006.01) | |
| *A61K 39/395* | (2006.01) | |
| *A61K 31/713* | (2006.01) | |
| *C07K 16/30* | (2006.01) | |
| *C12N 15/113* | (2010.01) | |
| *A61K 31/7088* | (2006.01) | |
| *A61K 38/02* | (2006.01) | |
| *G01N 33/50* | (2006.01) | |

(52) U.S. Cl.
CPC ....... *A61K 39/39558* (2013.01); *A61K 31/7088* (2013.01); *A61K 31/713* (2013.01); *A61K 38/02* (2013.01); *C07K 16/3015* (2013.01); *C12N 15/1138* (2013.01); *G01N 33/5011* (2013.01); *C12N 2310/14* (2013.01)

(58) Field of Classification Search
None
See application file for complete search history.

(56) References Cited

U.S. PATENT DOCUMENTS
| | | | |
|---|---|---|---|
| 2005/0047996 A1* | 3/2005 | Vogelstein et al. .......... 424/1.49 |
| 2009/0093002 A1 | 4/2009 | Pfeifer et al. | |
| 2010/0119445 A1 | 5/2010 | Leenders et al. | |
| 2011/0206700 A1 | 8/2011 | Hoffee et al. | |

FOREIGN PATENT DOCUMENTS
| | | |
|---|---|---|
| EP | 0 125 023 | 11/1984 |
| WO | WO 96/02576 | 2/1996 |
| WO | WO 99/32619 | 7/1999 |
| WO | WO 01/14420 A2 | 3/2001 |
| WO | WO 01/29058 A1 | 4/2001 |
| WO | WO 03/031930 A2 | 4/2003 |
| WO | WO 2006/110593 A2 | 10/2006 |
| WO | WO 2010/129917 A2 | 11/2012 |

OTHER PUBLICATIONS

Ye et al. (BMC Cancer 2010:10,1-11).*
Slamon et al. (NEJM 2001: 783-792).*
International Search Report issued in related International Patent Application No. PCT/EP2012/052238, dated Apr. 25, 2012.
Bargmann, "The neu oncogene encodes an epidermal growth factor receptor-related protein", *Nature*, vol. 319, pp. 226-230 (1986).
Bernstein, "Role for a bidentate ribonuclease in the initiation step of RNA interference", *Nature*, vol. 409, pp. 363-366 (2001).
Bock, "Selection of single-stranded DNA molecules that bind and inhibit human thrombin", *Nature*, vol. 355, No. 6360, pp. 564-566 (1992).
Elbashir, "RNA interference is mediated by 21-and 22-nucleotide RNAs", *Genes. Dev.*, vol. 15, pp. 188-200 (2001).
Elbashir, "Duplexes of 21-nucleotide RNAs mediate RNA interference in cultured mammalian cells", *Nature*, vol. 411, pp. 494-498 (2001).
Ellington, "In Vitro selection of RNA molecules that bind specific ligands", *Nature*, vol. 346, No. 6287, pp. 818-822 (1990).
Fire "RNA-triggered gene silencing", *Trends Genet.*, vol. 15, pp. 358-363 (1999).
Fire, "Patent and specific genetic interference by double-stranted RNA in *Caenorhabditis elegans*", *Nature*, vol. 391, pp. 806-811 (1998).
Guy, "Expression of the neu protooncogene in the mammary epithelium of transgenic mice induces metastatic disease", *Proc. Natl. Acad. Sci.*, vol. 89, pp. 10578-10582 (1992).
Hamilton, "A species of small antisense RNA in Posttranscriptional Gene Silencing in Plants", *Science*, vol. 286, pp. 950-952 (1999).
Hammond, "An RNA-directed nuclease mediates post-transcriptional gene silencing in *Drosophila* cells", *Nature*, vol. 404, pp. 293-296 (2000).
Hammond, "Post-Transcriptional Gene Silencing by Double-Stranded RNA", *Nature Rev. Genet.*, vol. 2, pp. pp. 110-119 (2001).
Hoppe-Seyler, "Peptide aptamers: powerful new tools for molecular medicine", *J. Mol. Med.*, vol. 78, No. 8, pp. 466-470 (2000).
Lin, "Rho-regulatory proteins in breast cancer cell motility and invasion", *Breast Cancer Res. Treat*, vol. 84, pp. 49-60 (2004).

(Continued)

*Primary Examiner* — Kimberly Chong
(74) *Attorney, Agent, or Firm* — Foley & Lardner LLP

(57) ABSTRACT

The present invention concerns the field of cancer therapy. In particular, it relates to an antagonist of a B-type plexin which prevents the interaction of the B-type plexin with ErbB-2 for use as a medicament, in particular, for treating metastasizing cancer. The present invention also contemplates a method for identifying an antagonist which prevents the interaction of a B-type plexin with ErbB-2. Finally, the invention provides for a polynucleotide encoding a B-type plexin polypeptide which lacks a functional intracellular domain and the said polypeptide.

11 Claims, 43 Drawing Sheets

(56) References Cited

OTHER PUBLICATIONS

Figure 1:
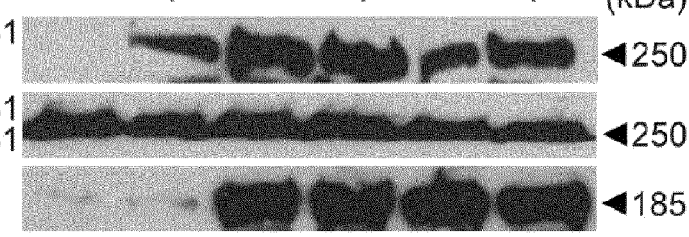
Figure 1:
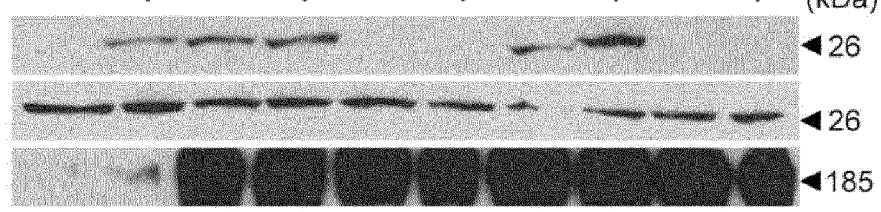
Figure 1:
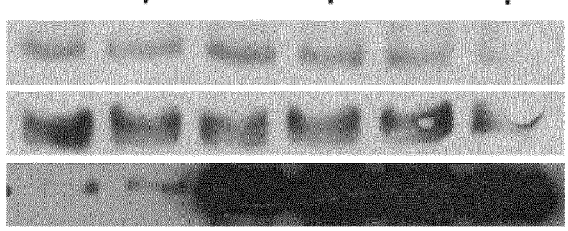
Figure 1:
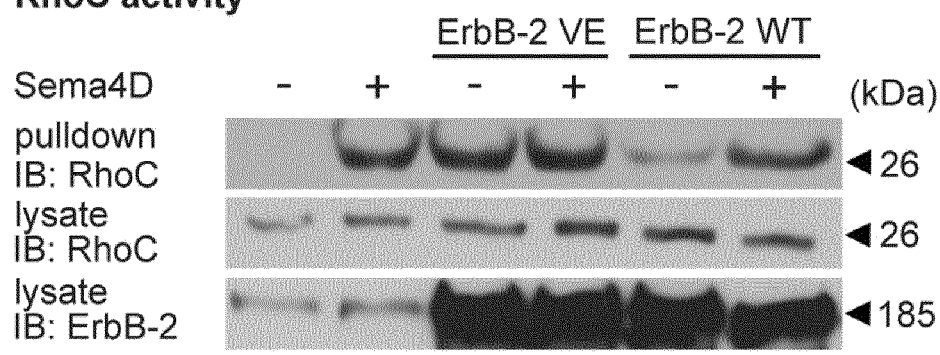
Figure 1:
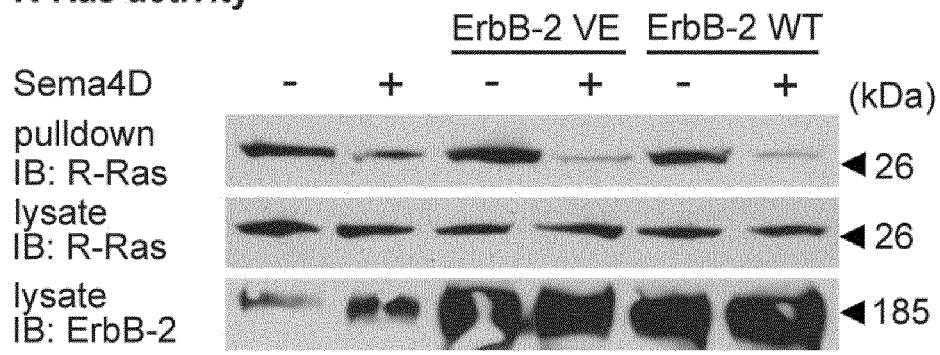

Muller, "Single-Step Induction of Mammary Adenocarcinoma in Transgenic Mice Bearing the Activated c-neu Oncogene" *Cell*, vol. 54, pp. 105-115 (1988).

Sahai, "RHO-GTPASES and Cancer" *Nat. Rev. Cancer*, vol. 2, pp. 133-142 (2002).

Sato, et al., "Reshaping a Human Antibody to Inhibit the Interleukin 6-dependent Tumor Cell Growth", *Cancer Res.*, vol. 53, pp. 851-856 (1993).

Sharp "RNA Interference", *Genes. Dev.*, vol. 15, pp. 485-490 (2001).

Slamon, "Studies of the HER-2/neu Proto-oncogene in Human Breast and Ovarian Cancer," *Science*, vol. 244, pp. 707-712 (1989).

Summerton, et al., "Morpholino Antisense Oligomers: Design, Preparation, and Properties", *Antisense & Nucleic Acid Drug Development*, vol. 7, No. 3, pp. 187-195 (1997).

Summerton, "Morpholino antisense oligomers: the case for an R Nase H-independent structural type," *Biochimica et Biophysica Acta*, vol. 1489, No. 1, pp. 141-158 (1999).

Swiercz et al., "Semaphorin 4D Signaling Requires the Recruitment of Phospholipase C Gamma into the Plexin-B1 Receptor Complex," *Molecular and Cellular Biology*, vol. 29, No. 23, pp. 6321-6334 (2009).

Swiercz, "Plexin-B1/RhoGEF-mediated RhoA activation involves the receptor tyrosine kinase ErbB-2" *J. Cell Biol.*, vol. 165, pp. 869-880 (2004).

Swiercz, et al., "ErbB-2 and Met Reciprocally Regulate Cellular Signaling via Plexin-B1," *Journ. of Biological Chemistry*, vol. 283, No. 4, pp. 1893-1901 (2008).

Tamagnone, "Plexins are a large family of receptors for transmembrane, secreted, and GPI-Anchored semaphorins in Vertebrates" *Cell*, vol. 99, pp. 71-80 (1990).

Tuschl, "RNA Interference and Small Interfering RNAs", *Chem. Biochem.*, vol. 2, pp. 239-245 (2001).

Vandamme, et al., "Construction and characterization of a recombinant murine monoclonal antibody directed against human fibrin fragment-D dimer," *Eur. J. Biochem.*, vol. 192, pp. 767-775 (1990).

Shuangmei et al., "Plexin-B1 Silencing Inhibits Ovarian Cancer Cell Migration and Invasion," *BMC Cancer*, vol. 10, No. 611, pp. 1-11 (2010).

Zamore, "RNAi: Double-Stranded RNA Directs the ATP-Dependent Cleavage of mRNA at 21 to 23 Nucleotide Intervals", *Cell*, vol. 101, pp. 25-33 (2000).

Sun et al., "Hypoxia-inducible Factor 1-Mediated Regulation of Semaphorin 4D Affects Tumor Growth and Vascularity," *The Journ. of Biological Chem.*, vol. 284, No. 46, pp. 32066-32074 (2009).

Deaglio et al., "CD38 and CD100 lead a network of surface receptors relaying positive signals for B-CLL growth and survival," *American Society of Hematology*, vol. 105, No. 8, pp. 3042-3050 (2005).

Janssen et al., "Structural basis of semaphoring-plexin signaling," vol. 467, No. 7319, pp. 1118-1122 (2010).

Hirotani et al., "Interaction of plexin-B1 with PDZ domain-containing Rho guanine nucleotide exchange factors," vol. 297, No. 1, pp. 32-37 (2002).

Wortfeld et al., "Her2/ErbB2 Signals through Plexin-B1 to Promote Breast Cancer Metastasis," *Naunyn-Schmiedeberg's Archives of Pharmacology*, vol. 383, No. Suppl. 1, p. 3 (2011).

Worzfeld et al., "ErbB-2 signals through Plexin-B1 to promote breast cancer metastatis," vol. 122, No. 4, pp. 1296-1305 (2012).

International Preliminary Report on Patentability and Written Opinion issued in related International Patent Application No. PCT/EP2012/052238, dated Aug. 22, 2013.

European Official Action dated Apr. 1, 2015, issued in related European Patent Application No. 12 706 220.6.

* cited by examiner

C

F

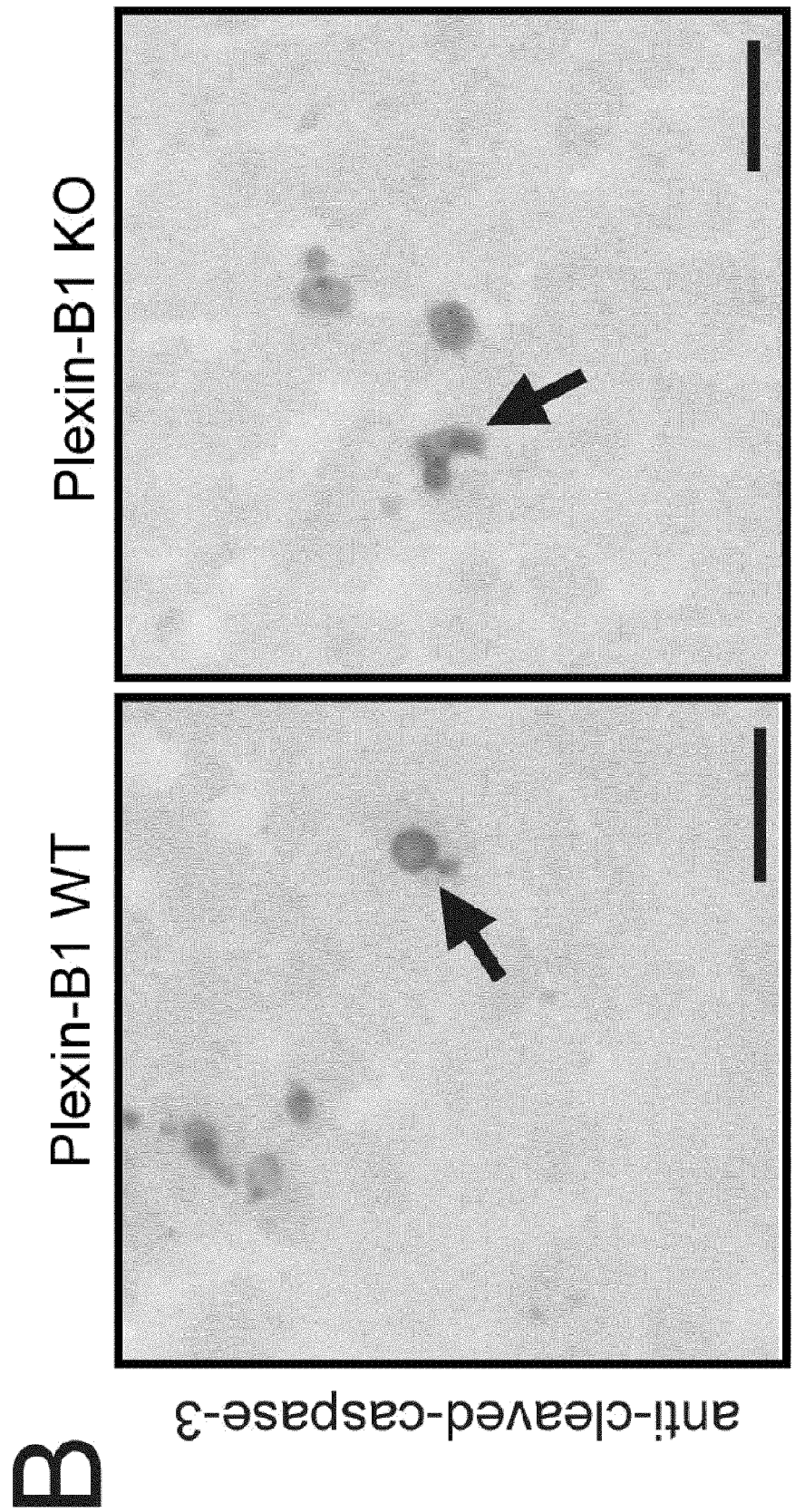

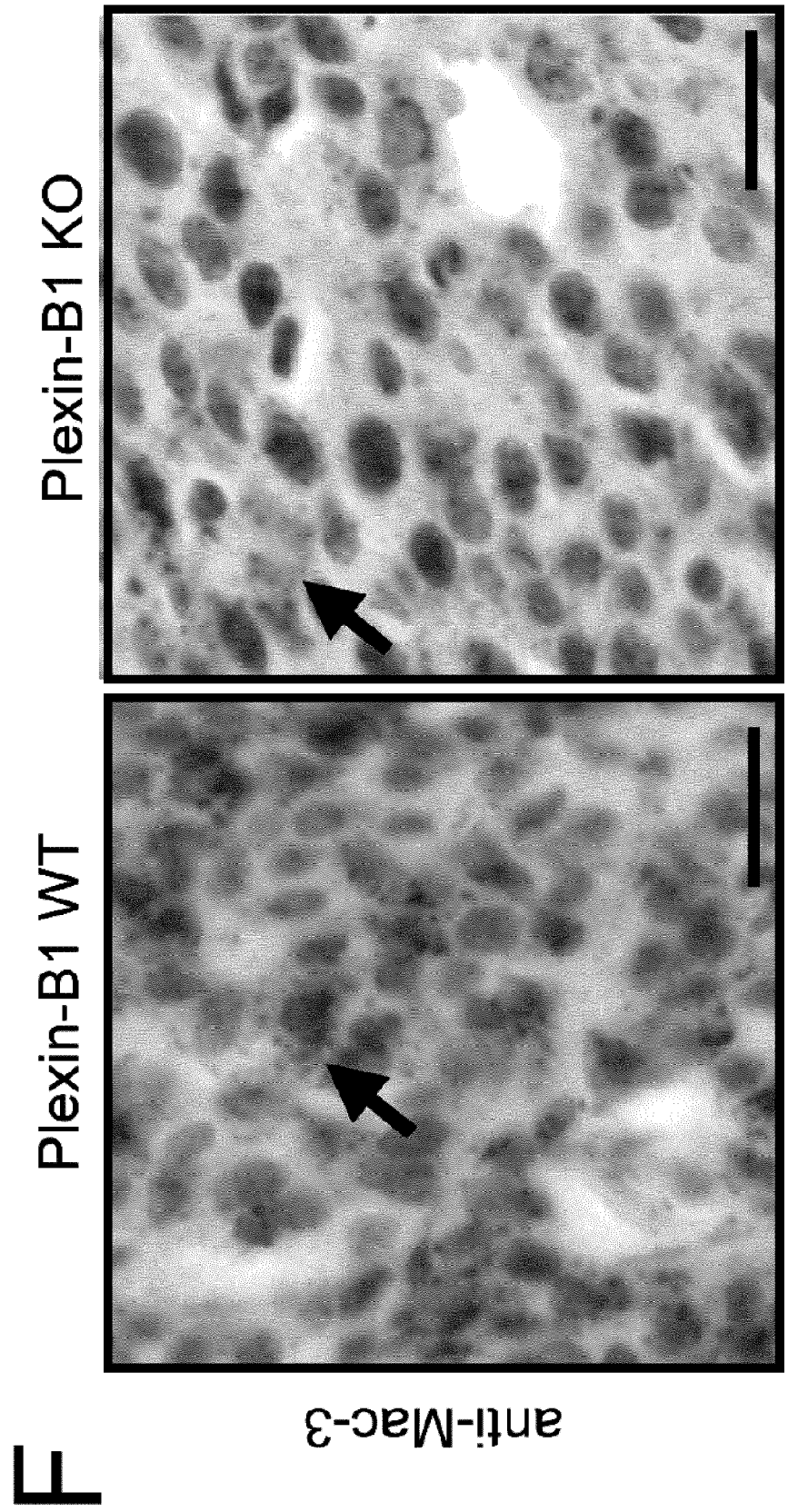

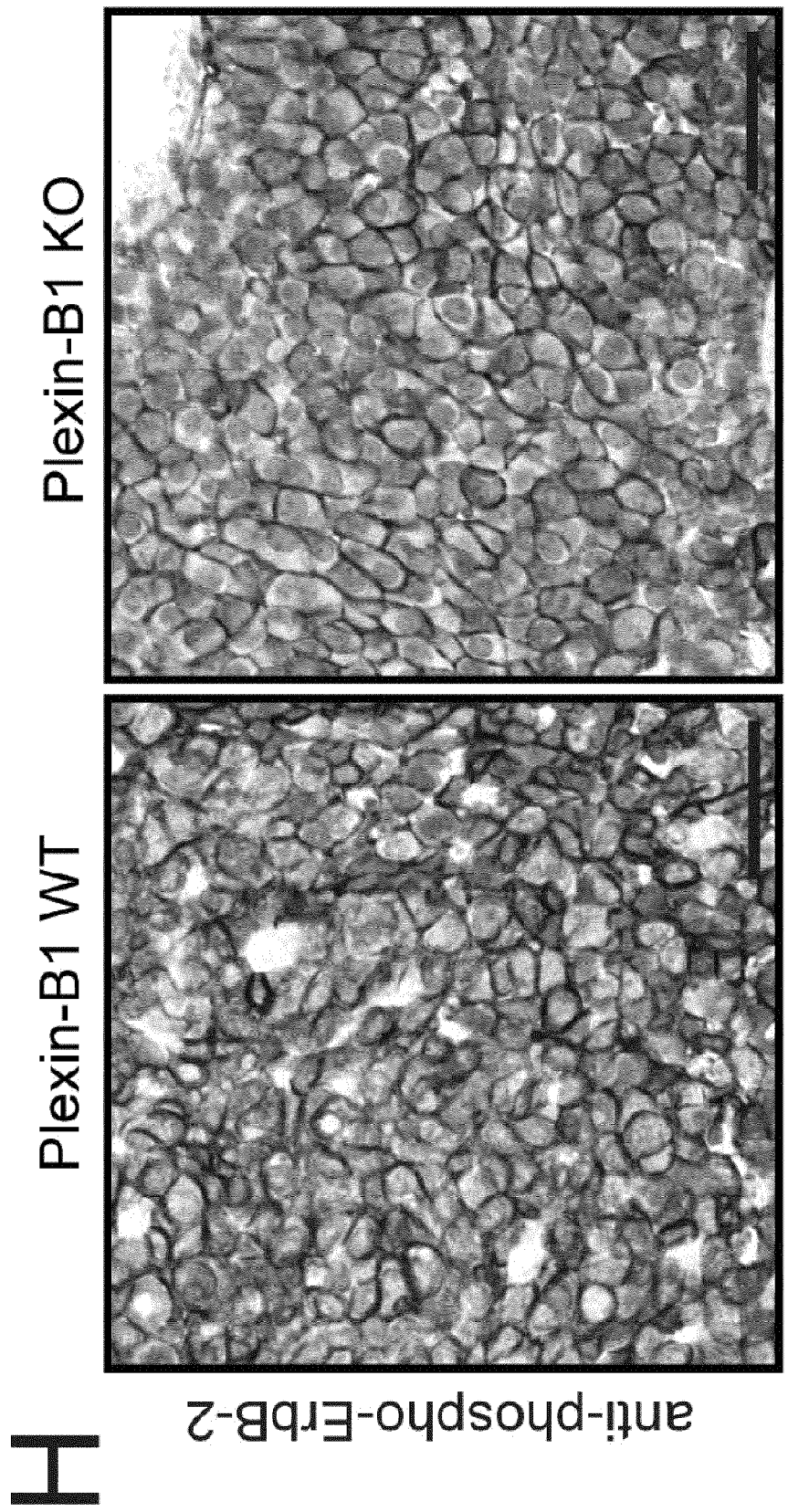

Fig. 10

A

| patient ID | DOB | histopathology | T | N | grade | ErbB-2 score |
|---|---|---|---|---|---|---|
| 2005 | 05/26/1954 | invasive ductal carcinoma | 1c | 0 (0/19) | 3 | 0 |
| 2030 | 03/13/1928 | invasive ductal carcinoma | 1c | 0 (0/23) | 1 | 0 |
| 2051 | 07/01/1930 | invasive lobular carcinoma | 3 (m) | 2 | 3 | 0 |
| 1900 | 08/14/1941 | invasive ductal carcinoma | 2 | 0 (0/22) | 3 | 3+ |
| 1935 | 06/14/1953 | invasive ductal carcinoma | 2 | 0 (0/21) | 3 | 3+ |
| 2004 | 11/27/1940 | invasive ductal carcinoma | 2 | 1 bi (1/21) | 3 | 3+ |

B

| patient ID | histopathology | ErbB-2 score |
|---|---|---|
| 3541 | invasive ductal carcinoma | 0 |
| 16897 | invasive ductal carcinoma | 3+ |

C

| patient ID | histopathology | grade | ErbB-2 score |
|---|---|---|---|
| 372 | invasive lobular carcinoma | G2 | 0 |
| 664 | invasive ductal carcinoma | G2 | 0 |
| 1635 | invasive medullary carcinoma | G3 | 0 |
| 4738 | invasive ductal carcinoma | G2 | 0 |
| 5499 | invasive ductal carcinoma | G2 | 1+ |
| 654 | invasive ductal carcinoma | G2 | 1+ |
| 3531 | invasive ductal carcinoma | G2 | 2+ |
| 4353 | invasive ductal carcinoma | G2 | 3+ |
| 1610 | invasive medullary carcinoma | G3 | 3+ |
| 102 | invasive ductal carcinoma | G2 | 0 |
| 934 | invasive lobular carcinoma | G2 | 0 |
| 851 | invasive ductal carcinoma | G2 | 0 |
| 5809 | invasive ductal carcinoma | G2 | 0 |
| 3405 | invasive mucinous carcinoma | G2 | 1+ |
| 1048 | invasive ductal carcinoma | G3 | 1+ |
| 3156 | invasive ductal carcinoma | G3 | 2+ |
| 5939 | invasive ductal carcinoma | G2 | 3+ |
| 4017 | invasive ductal carcinoma | G2 | 3+ |

Fig. 11

| Input | | Results | | | | | | | | | |
|---|---|---|---|---|---|---|---|---|---|---|---|
| clone number | WB | IP OE | IP native | co-IP ErbB2 | RhoA activity | | | | R-Ras deactivation | ELISA | | Invasion |
| | | | | | basal RhoA (ErbB2-dep/SKOV3) | Sema4d-dep (MCF-7) | Sema4D-dep (MCF-7) | SKOV vs. SKOVsh | blocking Sema4D binding | Crossre-activity other plexins | basal RhoA-dependent invasivity |
| 19 | ++ | + | + | + | no effect | blocks | blocks | binding/no | yes | no | NT |
| 93 | ++ | + | + | - | blocks | blocks | no effect | binding/no | no | no | Yes |
| 527 | - | + | + | + | no effect | blocks | blocks | binding/no | yes | no | NT |
| 538 | - | + | + | - | blocks | blocks | no effect | binding/no | no | no | Yes |
| 635 | + | + | - | NA | no effect | no effect | no effect | no/no | no | NT | NA |
| 830 | nonspec | + | - | NA | no effect | no effect | no effect | binding/binding | no | NT | NA |
| | #1 | #2 | #3 | #4 | #5 | #6 | #7 | #8 | #9 | #10 | #11 |

B-TYPE PLEXIN ANTAGONISTS AND USES THEREOF

This application is the National Phase of International Patent Application No. PCT/EP2012/052238, filed Feb. 9, 2012, which claims priority from European Patent Application No. 11153784.1, filed Feb. 9, 2011. The contents of these applications in incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 11, 2013, is named 099314-0107_SL.txt and is 35,419 bytes in size.

The present invention concerns the field of cancer therapy. In particular, it relates to an antagonist of a B-type plexin which prevents the interaction of the B-type plexin with ErbB-2 for use as a medicament, in particular, for treating metastasizing cancer. The present invention also contemplates a method for identifying an antagonist which prevents the interaction of a B-type plexin with ErbB-2. Finally, the invention provides for a polynucleotide encoding a B-type plexin polypeptide which lacks a functional intracellular domain and the said polypeptide.

Breast cancer is the most common primary malignancy in women. About 30% of all breast cancers overexpress the receptor tyrosine kinase ErbB-2 (Slamon 1989, Science 244: 707-712). These tumors are characterized by aggressive behavior and poor prognosis. A plethora of evidence including transgenic mice which overexpress ErbB-2 in their mammary glands and subsequently develop breast cancer directly implicates ErbB-2 signalling in mammary oncogenesis (Muller 1988, Cell 54:105-15; Guy 1992, Proc Natl Acad Sci USA 89:10578-82). However, the signaling events downstream of ErbB-2 which are responsible for invasion and metastatic progression of these mammary tumors remain poorly understood.

Plexins are a family of transmembrane receptors for semaphorins, initially characterized in the context of axon guidance in the developing nervous system (Tamagnone 1990, Cell 99:71-80). Plexin-B1 has been shown to stably interact with ErbB-2 (Swiercz 2004, J Cell Biol 165:869-880). This interaction is critical for activation of the small GTPase RhoA by semaphorin ligands of Plexin-B1. The Rho family of small GTPases has been extensively studied for their role in invasion of cancer cells (Sahai 2002, Nat Rev Cancer 2:133-42). RhoA and RhoC, in particular, are overexpressed in breast cancer and contribute to metastasis and poor outcome in breast cancer patients (Lin 2004, Breast Cancer Res Treat 84:49-60). Moreover, binding of the ligand Sema4D to its receptor Plexin-B1 stimulates the kinase activity of ErbB-2 which leads to phosphorylation of Plexin-B1 at two specific tyrosine residues (Swiercz 2009, Mol Cell Biol 29:6321-34). Plexin D1 has been reported as a target protein for tumor diagnosis and therapy (US2010/119445).

However, measures for efficiently preventing invasion and metastasis of cancer and, in particular, breast cancer, are not yet available but nevertheless highly desired.

Accordingly, the present invention concerns the technical problem of providing means and methods for complying with the aforementioned needs. The technical problem is solved by the embodiments characterized in the claims and herein below.

Thus, the present invention relates to an antagonist of a B-type plexin which prevents the interaction of the B-type plexin with ErbB-2 for use as a medicament. Preferably, the present invention pertains to an antagonist of human plexin-B1 which prevents the interaction of human plexin-B1 with human ErbB-2 for use as a medicament.

The term "antagonist" as used herein refers to a compound which is capable to prevent the interaction between a B-type plexin and ErbB-2, preferably between human plexin-B1 and human ErbB-2. The prevention of the interaction can be a functional prevention or a functional and physical prevention of the interaction. A functional prevention of the interaction as meant in accordance with the present invention results in an inhibition or reduction of signaling of the ErbB-2/B-type plexin complex. Such an inhibition or reduction of signaling can be determined, preferably, by measuring the tyrosine phosphorylation of the B-type plexin, preferably human plexin-B1, or RhoA and/or RhoC activity, preferably human RhoA and/or RhoC activity, as described in the accompanying Examples, below. A reduction of signaling as referred to herein is, preferably, a statistically significant reduction in the measured activity. The prevention of the interaction can occur directly, i.e. by inhibiting the physical interaction of the B-type plexin with ErbB-2, or indirectly, i.e. via an inhibition of proteins which facilitate said physical interaction or by a reduction of the amount of one of the complex compounds, e.g., the B-type plexin polypeptide available in the cell or the ErbB-2 polypeptide available in the cell. Preferably, said antagonist prevents cancer cells from cancer cell invasion and metastasis in a subject. Preferably, the subject is human. This can be achieved, preferably, by inhibiting cell migration which can be tested as shown, for instance, in the following Examples. The antagonist to be used in accordance with the present invention is a compound which can be a small molecule chemical compound, a protein, particularly an antibody, a peptide compound, a nucleic acid, a polymer, or any other chemical compound. Such compounds are well known in the art and a compound acting as an antagonist can be identified by the methods referred to in accordance with the present invention elsewhere herein.

In one embodiment, said antagonist is a nucleic acid which is capable of hybridizing specifically to the B-type plexin gene, preferably the human plexin-B1 gene, or to its transcripts and which prevents expression of the B-type plexin polypeptide. More preferably, said nucleic acid is selected from the group consisting of: siRNA, micro RNA, antisense RNA, morpholino oligonucleotides, ribozymes, and triple helix forming agents. The aforementioned nucleic acid antagonists are characterized by comprising at least a stretch of contiguous nucleic acids which are complementary to a stretch of nucleic acids from the B-type plexin gene or its transcripts which are envisaged as a target. Details on the nucleic acid sequences of the B-type plexins are found elsewhere herein.

Small interfering RNAs (siRNAs) are complementary to target RNAs (i.e. RNAs transcribed from a gene of interest to be antagonized). The siRNAs elicit RNA interference (RNAi) and, thereby, reduce or abolish the translation of protein from the transcripts of the gene of interest. Similarly, micro RNAs comprise complementary RNA targeting sequences and also act via RNAi mechanisms. Without being bound by theory, RNAi is generally used to silence expression of a gene of interest by targeting mRNA. Briefly, the process of RNAi in the cell is initiated by double stranded RNAs (dsRNAs) which are cleaved by a ribonuclease, thus producing siRNA duplexes. The siRNA binds to another intracellular enzyme complex which is thereby activated to target whatever mRNA molecules are homologous (or complementary) to the siRNA sequence. The function of the complex is to target the homologous mRNA molecule through base pairing interactions between one of the siRNA strands and the target mRNA. The mRNA is then cleaved approximately 12 nucleotides from the 3' terminus of the siRNA and degraded. In this manner, specific mRNAs can be targeted and degraded, thereby resulting in a loss of protein expression from the targeted mRNA. A complementary nucleotide sequence as used herein refers to the region on the RNA strand that is complementary to an RNA transcript of a portion of the target gene. The term "dsRNA" refers to RNA having a duplex structure comprising two complementary and anti-parallel nucleic acid strands. Not all nucleotides of a dsRNA necessarily exhibit complete Watson-Crick base pairs; the two RNA strands may be substantially complementary. The RNA strands forming the dsRNA may have the same or a different number of nucleotides, with the maximum number of base pairs being the number of nucleotides in the shortest strand of the dsRNA. Preferably, the dsRNA is no more than 49, more preferably less than 25, and most preferably between 19 and 23, i.e. 19, 20, 21, 22 or 23 nucleotides in length. dsRNAs of this length are particularly efficient in inhibiting the expression of the target gene using RNAi techniques. dsRNAs are subsequently degraded by a ribonuclease enzyme into short interfering RNAs (siRNAs). The complementary regions of the siRNA allow sufficient hybridization of the siRNA to the target RNA and thus mediate RNAi. In mammalian cells, siRNAs are approximately 21-25 nucleotides in length. The siRNA sequence needs to be of sufficient length to bring the siRNA and target RNA together through complementary base-pairing interactions. The length of the siRNA is preferably greater than or equal to ten nucleotides and of sufficient length to stably interact with the target RNA; specifically 15-30 nucleotides; more specifically any integer between 15 and 30 nucleotides, most preferably 15, 16, 17, 18, 19, 20, 21, 22, 23, 24, 25, 26, 27, 28, 29, and 30 nucleotides. By "sufficient length" is meant an oligonucleotide of greater than or equal to 15 nucleotides that is of a length great enough to provide the intended function under the expected condition. By "stably interact" is meant interaction of the small interfering RNA with target nucleic acid (e.g., by forming hydrogen bonds with complementary nucleotides in the target under physiological conditions). Generally, such complementarity is 100% between the siRNA and the RNA target, but can be less if desired, preferably 90%, 91%, 92%, 93%, 94%, 95%, 96%, 97%, 98%, or 99%. For example, 19 bases out of 21 bases may be base-paired. In some instances, where selection between various allelic variants is desired, 100% complementarity to the target gene is required in order to effectively discern the target sequence from the other allelic sequence. When selecting between allelic targets, choice of length is also an important factor because it is the other factor involved in the percent complementarity and the ability to differentiate between allelic differences. Methods relating to the use of RNAi to silence genes in organisms, including *C. elegans, Drosophila*, plants, and mammals, are known in the art (see, for example, Fire 1998, Nature 391:806-811; Fire 1999, Trends Genet. 15, 358-363; Sharp 2001, Genes Dev. 15,485-490; Hammond 2001, Nature Rev. Genet. 2, 1110-1119; Tuschl 2001, Chem. Biochem. 2, 239-245; Hamilton 1999, Science 286, 950-952; Hammond 2000, Nature 404, 293-296; Zamore 2000, Cell 101, 25-33; Bernstein 2001, Nature 409, 363-366; Elbashir 2001, Genes Dev. 15, 188-200; WO 0129058; WO 09932619; and Elbashir 2001, Nature 411: 494-498).

Antisense nucleic acid molecules are, preferably, RNA and comprise a nucleic acid sequence which is essentially or perfectly complementary to the target transcript. Preferably, an antisense nucleic acid molecule essentially consists of a nucleic acid sequence being complementary to at least 25 contiguous nucleotides, at least 50 contiguous nucleotides, at least 100 contiguous nucleotides, more preferably, at least 200, at least 300, at least 400 or at least 500 contiguous nucleotides of the target transcript. How to generate and use antisense nucleic acid molecules is well known in the art (see, e.g., Weiss, B. (ed.): Antisense Oligodeoxynucleotides and Antisense RNA: Novel Pharmacological and Therapeutic Agents, CRC Press, Boca Raton, Fla., 1997).

Morpholino oligonucleotides (or morpholinos) are synthetic nucleic acid molecules having a length of about 20 to 30 nucleotides and, typically about 25 nucleotides. Morpholinos bind to complementary sequences of target transcripts by standard nucleic acid base-pairing. They have standard nucleic acid bases which are bound to morpholine rings instead of deoxyribose rings and linked through phosphorodiamidate groups instead of phosphates (see, e.g., Summerton 1997, Antisense & Nucleic Acid Drug Development 7 (3): 187-95). Due to replacement of anionic phosphates into the uncharged phosphorodiamidate groups, ionization in the usual physiological pH range is prevented, so that morpholinos in organisms or cells are uncharged molecules. The entire backbone of a morpholino is made from these modified subunits. Unlike inhibitory small RNA molecules, morpholinos do not degrade their target RNA molecules. Rather, they sterically block binding to a target sequence within a RNA and simply getting in the way of molecules that might otherwise interact with the RNA (see, e.g., Summerton 1999, Biochimica et Biophysica Acta 1489 (1): 141-58).

Ribozymes are catalytic RNA molecules possessing a well defined tertiary structure that allows for catalyzing either the hydrolysis of one of their own phosphodiester bonds (self-cleaving ribozymes), or the hydrolysis of bonds in other RNAs, but they have also been found to catalyze the aminotransferase activity of the ribosome. The ribozymes envisaged in accordance with the present invention are, preferably, those which specifically hydrolyse the target transcripts. In particular, hammerhead ribozymes are preferred in accordance with the present invention. How to generate and use such ribozymes is well known in the art (see, e.g., Hean J, Weinberg M S (2008). "The Hammerhead Ribozyme Revisited: New Biological Insights for the Development of Therapeutic Agents and for Reverse Genomics Applications". In Morris K L. RNA and the Regulation of Gene Expression: A Hidden Layer of Complexity. Norfolk, England: Caister Academic Press).

Also envisaged as antagonists of the present invention are triple-helix forming agents. These agents are also oligonucleotides which form a triple-structure with the gene of interest to be antagonized. Usually, said triple-helix shall be formed in regulatory regions of the gene and abolishes efficient transcription of mRNA from the said gene. How to design and generate such triple-helix forming agents is well known in the art.

Moreover, particular preferred antagonistic nucleic acids are described in the accompanying Examples below. Thus, most preferably, the nucleic acid comprises or has a nucleic acid sequence as shown in SEQ ID NO: 3.

In another embodiment, the antagonist of the invention specifically binds to the B-type plexin polypeptide, preferably human plexin-B1, and (i) inhibits binding of said B-type plexin polypeptide, preferably human plexin-B1, to Erb-B2, preferably human Erb-B2, or (ii) inhibits binding of the ligand Sema4D, preferably human Sema4D, to its receptor B-type plexin polypeptide, preferably human plexin-B1. More preferably, said antagonist binds to the extracellular domain of a B-type plexin, more preferably to amino acids 20 to 534 of human plexin-B1 shown in SEQ ID NO: 2, or a fragment thereof which is about 5, 6, 7, 8, 9, 10, 11, 12, 13, 14, 15, 20, 25, 30, 40, 50, 75, 100, 150, 200, or 300 amino acid residues in length. Preferably, said antagonist is selected from the group consisting of: antibodies, aptameres, peptides, and polypeptides. The structure of the B-type plexins is described elsewhere herein. By conventional binding studies, the person skilled in the art can determine whether an antagonist will bind to the extracellular domain of a B-type plexin. Moreover, by the functional tests referred to elsewhere herein, it can be determined whether the interaction of the ErbB-2 and the B-type plexin is functionally prevented. Methods for generating antibodies, aptameres, peptides, and polypeptides which bind to the extracellular domain of the B-type plexins are well known in the art.

Antibodies as referred to herein, preferably, encompass all types of antibodies which, preferably, specifically bind to the extracellular domain or a fragment thereof of a B-type plexin. Preferably, the antibody of the present invention is a monoclonal antibody, a polyclonal antibody, a single chain antibody, a chimeric antibody, a humanized antibody, or any fragment or derivative of such antibodies being still capable of specifically binding to the extracellular domain of a B-type plexin or a fragment thereof. In addition to specifically binding to the extracellular domain of a B-type plexin (preferably human plexin-B1) or a fragment thereof, said antibody or fragment thereof (i) inhibits binding of said B-type plexin polypeptide, preferably human plexin-B1, to Erb-B2, preferably human Erb-B2, or (ii) inhibits binding of the ligand Sema4D, preferably human Sema4D, to its receptor B-type plexin polypeptide, preferably human plexin-B1. Preferably, said antibody is a rodent (e.g. mouse or rat), primate (e.g. chimpanzee, baboon, cynomolgus, rhesus, marmoset, or macaque) or human polyclonal or monoclonal antibody, even more preferred a mouse monoclonal antibody, as characterized elsewhere herein. Fragments and derivatives comprised by the term "antibody" as used herein encompasses a bispecific antibody, a single chain bispecific antibody, a diabody, a synthetic antibody, an Fab, F(ab)$_2$, Fv or scFv fragment as well as any chemically modified derivative of any of these antibodies. Specific binding as used in the context of the antibody of the present invention, preferably, means that the antibody does not cross react with other polypeptides. For example, a monoclonal antibody specifically binding to a B-type plexin polypeptide, e.g. plexin-B1, does not bind to an A-, C- or D-type plexin polypeptide. Specific binding can be tested by various well known techniques and as shown in the following examples. Antibodies or fragments thereof, in general, can be obtained by using methods which are described, e.g., in Harlow and Lane "Antibodies, A Laboratory Manual", CSH Press, Cold Spring Harbor, 1988. Monoclonal antibodies can be prepared by the techniques which comprise the fusion of mouse myeloma cells to spleen cells derived from immunized mammals and, preferably, immunized mice (Köhler 1975, Nature 256, 495, and Galfré 1981, Meth Enzymol 73, 3). Preferably, an immunogenic (poly)peptide comprising the extracellular domain of a B-type plexin, more preferably human plexin-B1, most preferably amino acid residues 20 to 534 of human plexin-B1 shown in SEQ ID NO: 2, or a fragment thereof which is about 5, 6, 7, 8, 9, 10, 11, 12, 15, 20, 25, 30, 40, 50, 75, 100, 150, 200, 300, 400, or even 500 amino acid residues in length is applied to a mammal as described in the following Examples. The said (poly)peptide is, preferably, conjugated to a carrier protein, such as bovine serum albumin, thyroglobulin, and keyhole limpet hemocyanin (KLH). Depending on the host species, various adjuvants can be used to increase the immunological response. Such adjuvants encompass, preferably, Freund's adjuvant, mineral gels, e.g., aluminum hydroxide, and surface active substances, e.g., lysolecithin, pluronic polyols, polyanions, peptides, oil emulsions, keyhole limpet hemocyanin, and dinitrophenol. Monoclonal antibodies which specifically bind to the extracellular domain of the B-type plexin can be subsequently prepared using the well known hybridoma technique, the human B cell hybridoma technique, and the EBV hybridoma technique.

In a preferred embodiment, the present invention provides an antibody or a fragment thereof, which comprises an H (heavy) chain V (variable) region comprising an amino acid sequence shown in SEQ ID NO. 15 and/or a L (light) chain V (variable) region comprising an amino acid sequence shown in SEQ ID NO. 16. Further encompassed by the invention are antibodies or fragments thereof which comprise one, two or three complementarity determining regions (CDRs) of said heavy chain and/or light chain variable region(s). The mentioned sequences correspond to mouse monoclonal antibody #93 as characterized and used in the following Examples. In addition, the present invention provides an antibody or a fragment thereof, which comprises an H (heavy) chain V (variable) region comprising an amino acid sequence shown in SEQ ID NO. 19 and/or a L (light) chain V (variable) region comprising an amino acid sequence shown in SEQ ID NO. 20. Further encompassed by the invention are antibodies which comprise one, two or three complementarity determining regions (CDRs) of said heavy chain and/or light chain variable region(s). Said sequences correspond to mouse monoclonal antibody #538 as characterized and used in the following Examples. As shown therein, both mouse monoclonal antibodies #93 and #538 bind to the extracellular domain of human plexin-B1 or a partial peptide or fragment thereof and inhibit binding of said B-type plexin polypeptide to Erb-B2.

Surprisingly, it has been found that the mouse monoclonal anti-Plexin-B1 antibody #93 (also referred to herein as clone number 93) interferes with the interaction between ErbB-2 and Plexin-B1, but does not inhibit binding of the ligand Sema4D to the receptor Plexin-B1.

More specifically, mouse monoclonal anti-Plexin-B1 antibody (mAb) #93 specifically binds to human Plexin-B1, i.e. amino acid residues 20 to 534 of human plexin-B1 shown in SEQ ID NO: 2 comprising the Semaphorin domain and one PSI domain. #93 shows specific binding in Western blot and immunoblot at a concentration of 10 microgram/ml (strong signal; see column 1 in FIG. 11), and is able to precipitate Plexin-B1 overexpressed in HEK cells (column 2 in FIG. 11) and native Plexin-B1 in MCF-7 cells (column 3 in FIG. 11). Further, #93 blocks Plexin-B1 interaction with ErbB2 in MCF-7, BT-474 and SK-OV-3 cells (column 4 in FIG. 11), without interfering with binding of (the ligand) Sema4D to (the receptor) Plexin-B1 (column 9 in FIG. 11). In addition, #93 blocks RhoA activity, both basal RhoA activity in SK-OV-3 cells (column 5 in FIG. 11) and Sema4D-dependent RhoA activation in MCF-7 cells (column 6 in FIG. 11), due to the inhibition of Plexin-B1/ErbB2 interaction. In contrast, #93 has no effect on R-Ras deactivation via Plexin-B1 after stimulation with Sema4D in MCF-7 cells. #93 binds specifically to Plexin-B1, and exhibits no cross-reactivity to other Plexin-family members (columns 8 and 10 of FIG. 11). Finally, #93 blocks Rho-A mediated basal cell invasivity in the Matrigel invasion assay, both for SK-OV-3 and BT-474 cells, due to the inhibition of plexin-B1/ErbB2 interaction (column 11 of FIG. 11).

Mouse monoclonal anti-Plexin-B1 antibody (mAb) #538 shows similar characteristics as #93, with the only exception, that #538 is not able to recognize human Plexin-B1 in Western blot/immunoblot (column 1 of FIG. 11). As #93, #538 inhibits the interaction of Plexin-B1 and ErbB2.

A detailed characterization of mouse monoclonal anti-Plexin-B1 antibodies #93 and #538 is provided by the following Examples.

In another preferred embodiment, the term "antagonist" as used herein refers to a compound which is capable of binding to the extracellular domain of a B-type plexin polypeptide and of inhibiting or blocking binding of the respective ligand to the receptor B-type plexin polypeptide. Preferably, said compound inhibits or blocks binding of the ligand Sema4D to human plexin-1, e.g., by competitive binding. Preferably, said antagonist is selected from the group consisting of: antibodies, aptameres, peptides, and polypeptides. The structure of the B-type plexins is described elsewhere herein. By conventional binding studies, the person skilled in the art can determine whether an antagonist will bind to the extracellular domain of a B-type plexin. Moreover, by the functional tests described elsewhere herein, it can be determined whether the compound blocks or inhibits binding of the respective ligand to the receptor, i.e. the B-type plexin. Methods for generating antibodies, aptameres, peptides, and polypeptides which bind to the extracellular domain of the B-type plexins are well known in the art.

More specifically, the present invention provides an antibody or a fragment thereof, which comprises an H (heavy) chain V (variable) region comprising an amino acid sequence shown in SEQ ID NO. 13 and/or a L (light) chain V (variable) region comprising an amino acid sequence shown in SEQ ID NO. 14. Further encompassed by the invention are antibodies which comprise one, two or three complementarity determining regions (CDRs) of said heavy chain and/or light chain variable region(s). Said sequences correspond to mouse monoclonal anti-Plexin-B1 antibody #19 as characterized and used in the following Examples. In addition, the present invention provides an antibody or a fragment thereof, which comprises an H (heavy) chain V (variable) region comprising an amino acid sequence shown in SEQ ID NO. 17 and/or a L (light) chain V (variable) region comprising an amino acid sequence shown in SEQ ID NO. 18. Further encompassed by the invention are antibodies which comprise one, two or three complementarity determining regions (CDRs) of said heavy chain and/or light chain variable region(s). Said sequences correspond to mouse monoclonal anti-Plexin-B1 antibody #527 as characterized and used in the following Examples. Mouse monoclonal antibodies #19 and #527 bind to the extracellular domain of human plexin-B1 or a partial peptide or fragment thereof and inhibit binding of the ligand Sema4D to human plexin-B1. Mouse monoclonal anti-Plexin-B1 antibody (mAb) #527 shows similar results as #19, with the only exception, that #527 is not able to recognize human Plexin-B1 in Western blot (column 1 of FIG. 11). FIG. 11 and the following Examples show the specific characteristics of #19 and #527 which both specifically bind to the extracellular domain of human Plexin-B1, i.e. amino acid residues 20 to 534 of human plexin-B1 shown in SEQ ID NO: 2, comprising the Semaphorin domain and one PSI domain.

In an alternative preferred embodiment, the antibody is a chimeric antibody.

Preferably, the chimeric antibody comprises an H (heavy) chain V (variable) region comprising an amino acid sequence shown in SEQ ID NO. 15 and/or a L (light) chain V (variable) region comprising an amino acid sequence shown in SEQ ID NO. 16. Preferably, the chimeric antibody comprises an H (heavy) chain V (variable) region comprising an amino acid sequence shown in SEQ ID NO. 19 and/or a L (light) chain V (variable) region comprising an amino acid sequence shown in SEQ ID NO. 20. Such chimeric antibodies bind to the extracellular domain of human plexin-B1 or a partial peptide or fragment thereof and inhibit binding of said B-type plexin polypeptide to Erb-B2.

Preferably, the chimeric antibody comprises an H (heavy) chain V (variable) region comprising an amino acid sequence shown in SEQ ID NO. 13 and/or a L (light) chain V (variable) region comprising an amino acid sequence shown in SEQ ID NO. 14. Preferably, the chimeric antibody comprises an H (heavy) chain V (variable) region comprising an amino acid sequence shown in SEQ ID NO. 17 and/or a L (light) chain V (variable) region comprising an amino acid sequence shown in SEQ ID NO. 18. Such chimeric antibodies bind to the extracellular domain of human plexin-B1 or a partial peptide or fragment thereof and inhibit binding of the ligand Sema4D to said B-type plexin polypeptide.

Further encompassed by the invention are chimeric antibodies or fragments thereof which comprise one, two or three complementarity determining regions (CDRs) of said heavy chain and/or light chain variable region(s) described herein.

In one embodiment, the chimeric antibody further comprises a human antibody C (constant) region.

In an alternative preferred embodiment, the antibody is a humanized antibody.

Preferably, the humanized antibody comprises an H (heavy) chain V (variable) region comprising an amino acid sequence shown in SEQ ID NO. 15 and/or a L (light) chain V (variable) region comprising an amino acid sequence shown in SEQ ID NO. 16. Preferably, the humanized antibody comprises an H (heavy) chain V (variable) region comprising an amino acid sequence shown in SEQ ID NO. 19 and/or a L (light) chain V (variable) region comprising an amino acid sequence shown in SEQ ID NO. 20. Such humanized antibodies bind to the extracellular domain of human plexin-B1 or a partial peptide or fragment thereof and inhibit binding of said B-type plexin polypeptide to Erb-B2.

Preferably, the humanized antibody comprises an H (heavy) chain V (variable) region comprising an amino acid sequence shown in SEQ ID NO. 13 and/or a L (light) chain V (variable) region comprising an amino acid sequence shown in SEQ ID NO. 14. Preferably, the humanized antibody comprises an H (heavy) chain V (variable) region comprising an amino acid sequence shown in SEQ ID NO. 17 and/or a L (light) chain V (variable) region comprising an amino acid sequence shown in SEQ ID NO. 18. Such humanized antibodies bind to the extracellular domain of human plexin-B1 or a partial peptide or fragment thereof and inhibit binding of the ligand Sema4D to said B-type plexin polypeptide.

In one embodiment, the humanized antibody further comprises a human antibody FR (framework) region and/or a human antibody C region.

Further encompassed by the invention are humanized antibodies or fragments thereof which comprise one, two or three complementarity determining regions (CDRs) of said heavy chain and/or light chain variable region(s) described herein.

In yet an alternative embodiment, the antibody or fragment thereof can be labeled with a radioisotope label or a fluorescent label. Such radio isotope label includes, for example, $^{90}$yttrium ($^{90}$Y), $^{125}$iodine ($^{125}$I) and $^{111}$indium ($^{111}$In). Fluorescent labels include, for instance, fluorescein, rhodamine, or Alexa Fluors.

Antibodies that can be used in the present invention specifically bind to a B-type plexin polypeptide, preferably human plexin-B1, more preferably to the extracellular domain or a fragment thereof. The antibodies (polyclonal antibodies and monoclonal antibodies) of the present invention can be prepared, for example, by the following process.

Initially, an antigen is prepared for the production of an antibody useful in the present invention. B-type plexin polypeptide or its partial peptide can be used as an immunogenic protein. Alternatively, a cell expressing B-type plexin polypeptide or its partial peptide can also be used as an immunogen. The amino acid sequences of B-type plexin polypeptides used as the immunogen in the present invention and the cDNA sequences encoding the proteins are publicly available in GenBank. The B-type plexin polypeptide or its partial peptide for use as the immunogen can be synthetically prepared according to a procedure known in the art such as a solid-phase peptide synthesis process, using the available amino acid sequence information. The partial peptides of B-type plexin polypeptide include, but are not limited to, a peptide containing amino acid residues 20 to 534 of the amino acid sequence shown in SEQ ID NO: 2, which corresponds to a part of the extracellular domain of human plexin-B1; see the following Examples.

The protein or its partial peptide, or the cell expressing them can be prepared by using the sequence information of cDNA encoding B-type plexin polypeptide or its partial peptide according to a known gene recombination procedure. The production of the protein or its partial peptide as well as the cell expressing them according to such a gene recombination procedure will be illustrated below.

A recombinant vector for the production of protein can be obtained by linking the above cDNA sequence to an appropriate vector. A transformant can be obtained by introducing the recombinant vector for the production of protein into a host so that the target B-type plexin polypeptide or its partial peptide can be expressed.

As the vector, a phage or plasmid that is capable of autonomously replicating in a host is used. Examples of a plasmid DNA include pCAGGS, pET28, pGEX4T, pUC118, pUC119, pUC18, pUC19, and other plasmid DNAs derived from *Escherichia coli*; pUB110, pTP5, and other plasmid DNAs derived from *Bacillus subtilis*; and YEp13, YEp24, YCp50 and other plasmid DNAs derived from yeast. Examples of a phage DNA include lambda phages such as λgt11 and λZAP. In addition, animal virus vectors such as retrovirus vector and vaccinia virus vector can be used, and insect virus vectors such as baculovirus vector can also be used.

The DNA encoding the B-type plexin polypeptide or its partial peptide is inserted into the vector, for example, by the following method. In this method, purified DNA is cleaved by an appropriate restriction enzyme and inserted into a restriction enzyme site or a multicloning site of an appropriate vector DNA to ligate into the vector.

In addition to a promoter and the B-type plexin DNA, any of enhancers and other cis elements, splicing signals, poly A addition signals, selective markers, ribosome binding site (RBS), and other elements can be ligated into the recombinant vector for the production of protein for use in mammalian cells, if desired.

For ligating the DNA fragment to the vector fragment, a known DNA ligase can be used. The DNA fragment and the vector fragment are annealed and ligated, thereby producing a recombinant vector for the production of a protein.

The host for use in transformation is not specifically limited as long as it allows the B-type plexin polypeptide or its partial peptide to be expressed therein. Examples of the host include bacteria, for example, *E. coli*, and *Bacillus*; yeast, for example, *Saccharomyces cerevisiae*; animal cells, for example, COS cells, Chinese Hamster Ovary (CHO) cells, and insect cells.

For example, when a bacterium is used as the host, the recombinant vector for the protein production should preferably be capable of autonomously replicating in the host bacterium and comprise a promoter, a ribosome binding site, the B-type plexin DNA, and a transcription termination sequence. The recombinant vector may further comprise a gene for regulating the promoter. An example of *Escherichia coli* includes *Escherichia coli* BRL, and an example of *Bacillus* is *Bacillus subtilis*. Any promoter that can be expressed in the host such as *Escherichia coli* can be used herein.

The recombinant vector can be introduced into the host bacterium by any procedures known in the art. Such procedures include, for example, a method using calcium ions and an electroporation. When yeast cell, an animal cell, or an insect cell is used as the host, a transformant can be produced according to a known procedure in the art, and then the B-type plexin polypeptide or its partial peptide can be produced in the host (transformant).

The B-type plexin polypeptide or its partial peptide for use as the immunogen in the present invention can be obtained from a culture of the above-generated transformant. The "culture" refers to any of culture supernatant, cultured cells, cultured microorganisms, and homogenates thereof. The transformant is cultured in a culture medium by a conventional process of culturing a host.

The culture medium for culturing the transformant obtained by using *Escherichia coli*, yeast, or other microorganisms as the host can be either a natural medium or a synthetic medium, as long as it comprises a carbon source, nitrogen source, inorganic salts, and other components utilizable by the microorganism and enables the transformant to grow efficiently.

The transformant is generally cultured by shaking culture or aeration culture with stirring under aerobic conditions at 25° C. to 37° C. for 3 to 6 hours. During culturing, pH is held at a level near neutrality by adjustment with, for example, an inorganic or organic acid, and an alkaline solution. During culturing, antibodies such as ampicillin or tetracycline may be added to the medium according to the selective marker inserted into the recombinant expression vector, if necessary.

After culturing, when the B-type plexin polypeptide or its partial peptide is produced within the microorganism or cell, the protein or its partial peptide is extracted by homogenizing the microorganism or cell. When the B-type plexin polypeptide or its partial peptide is secreted from the microorganism or cell, the culture medium is used as is, or debris of the microorganism or cell is removed from the culture medium, for example, by centrifugation. Thereafter, the B-type plexin polypeptide or its partial peptide can be isolated from the culture and purified by a conventional biochemical method for the isolation and purification of proteins, such as ammonium sulfate precipitation, gel chromatography, ion-exchange chromatography, and affinity chromatography, either individually or in combination.

Whether or not the B-type plexin polypeptide or its partial peptide has been obtained can be confirmed, for example, by SDS polyacrylamide gel electrophoresis.

Next, the obtained B-type plexin polypeptide protein or its partial peptide, or the transformant is dissolved in a buffer to prepare an immunogen. Where necessary, an adjuvant can be added thereto for effective immunization. Such adjuvants include, for example, commercially available Freund's complete adjuvant and Freund's incomplete adjuvant. Any of these adjuvants can be used alone or in combination.

The immunogen so prepared is administered to a mammal such as a rabbit, rat, or mouse. The immunization is performed mainly by intravenous, subcutaneous, or intraperitoneal injection.

The interval of immunization is not specifically limited and the mammal is immunized one to 3 times at intervals ranging from several days to weeks. Antibody-producing cells are collected 1 to 7 days after the last immunization. Examples of the antibody-producing cells include spleen cells, lymph node cells, and peripheral blood cells.

To obtain a hybridoma, an antibody-producing cell and a myeloma cell are fused. As the myeloma cell to be fused with the antibody-producing cell, a generally available established cell line can be used. Preferably, the cell line used should have drug selectivity and properties such that it cannot survive in a HAT selective medium (containing hypoxanthine, aminopterin, and thymidine) in unfused form and can survive only when fused with an antibody-producing cell. Possible myeloma cells include, for example, mouse myeloma cell lines such as P3X63-Ag.8.U1 (P3U1), and NS-I.

Next, the myeloma cell and the antibody-producing cell are fused. For the fusion, these cells are mixed, preferably at the ratio of the antibody-producing cell to the myeloma cell of 5:1, in a culture medium for animal cells which does not contain serum, such as DMEM and RPMI-1640 media, and fused in the presence of a cell fusion-promoting agent such as polyethylene glycol (PEG). The cell fusion may also be carried out by using a commercially available cell-fusing device using electroporation.

Then, the hybridoma is picked up from the cells after above fusion treatment. For example, a cell suspension is appropriately diluted with, for example, the RPMI-1640 medium containing fetal bovine serum and then plated onto a microtiter plate. A selective medium is added to each well, and the cells are cultured with appropriately replacing the selective medium. As a result, the cells that grow about 30 days after the start of culturing in the selective medium can be obtained as the hybridoma.

The culture supernatant of the growing hybridoma is then screened for the presence of an antibody that reacts with the B-type plexin polypeptide or its partial peptide. The screening of hybridoma can be performed according to a conventional procedure, for example, using enzyme-linked immunosorbent assay (ELISA), enzyme immunoassay (EIA) or radioimmunoassay (MA). The fused cells are cloned by the limiting dilution to establish a hybridoma, which produces the monoclonal antibody of interest.

The monoclonal antibody can be collected from the established hybridoma, for example, by a conventional cell culture method or by producing the ascites. If necessary, the antibody can be purified in the above-described antibody collecting method according to a known procedure such as ammonium sulfate precipitation, ion-exchange chromatography, gel filtration, affinity chromatography, or a combination thereof.

The globulin type of the monoclonal antibodies useful in the present invention is not specifically limited, as long as they are capable of specifically binding to the B-type plexin polypeptide and can be any of IgG, IgM, IgA, IgE, and IgD. Among them, IgG is preferred.

In the present invention, murine monoclonal antibodies #19, #93, #527, and #538 have been successfully established and preferably used, as shown in the following Examples.

In the present invention, a recombinant-type monoclonal antibody may also be used, which can be produced by cloning an antibody gene from the hybridoma, integrating the antibody gene into a suitable vector, introducing the vector into a host, and producing the antibody from the host according to a conventional genetic recombination technique (see, for example, Vandamme, A. M. et al., Eur. J. Biochem. (1990) 192: 767-75).

In the present invention, an artificially modified recombinant antibody may also be used, including a chimeric antibody and a humanized antibody. These modified antibodies can be prepared by any known method described in the art (see, e.g., US 2009/0093002 or US2011/0206700). A chimeric antibody is a molecule in which different portions are derived from different animal species, such as those having a variable region derived from a murine monoclonal antibody (mAb) and a human immunoglobulin constant region.

A chimeric antibody according to the present invention can be prepared by ligating the DNA encoding the antibody V (variable)—region to DNA encoding a human antibody C (constant)—region, integrating the ligation product into an expression vector, and introducing the resultant recombinant expression vector into a host to produce the chimeric antibody.

A humanized antibody is also referred to as "reshaped human antibody", in which the complementarity determining regions (CDRs) of an antibody of a non-human mammal (e.g., a mouse monoclonal antibody of the invention) are grafted to those of a human antibody. The general genetic recombination procedure for producing such humanized antibody is also known (for example, EP 125 023; WO 96/02576).

Specifically, a DNA sequence in which CDRs of a mouse monoclonal antibody of the invention are ligated through framework regions (FRs) is designed, and synthesized by a PCR method using several oligonucleotides as primers which were designed to have regions overlapping to the terminal regions of the CDRs and the FRs. The resultant DNA is ligated to DNA encoding the human antibody C-region, and the ligation product is integrated into an expression vector. The resultant recombinant expression vector is introduced into a host, thereby producing the humanized antibody (for example, WO 96/02576).

The FRs ligated through the CDRs are selected so that the CDRs can form a functional antigen binding site. If necessary, an amino acid(s) in the FRs of the antibody V-region may be replaced so that the CDRs of the reshaped human antibody can form an appropriate antigen binding site (Sato, K. et al., Cancer Res. (1993) 53: 851-6).

The chimeric antibody is composed of V-regions derived from a non-human mammal antibody and C-regions derived from a human antibody. The humanized antibody is composed of CDRs derived from a non-human mammal antibody and FRs and C-regions derived from a human antibody. The humanized antibody may be useful for clinical use, because the antigenicity of the antibody against a human body is reduced.

A specific example of a chimeric antibody or a humanized antibody used in the present invention is an antibody in which the CDRs are derived from the mouse monoclonal antibodies of the invention.

"Aptamers" as used herein are, preferably, oligonucleotides or peptide molecules that bind to a specific target molecule (Ellington 1990, Nature 346 (6287): 818-22). Bock 1992, Nature 355 (6360): 564-6). Oligonucleotide aptamers are engineered through repeated rounds of selection or the so called systematic evolution of ligands by exponential enrichment (SELEX technology). Peptide aptamers are designed to interfere with protein interactions inside cells. They usually comprise of a variable peptide loop attached at both ends to a protein scaffold. This double structural constraint shall increase the binding affinity of the peptide aptamer into the nanomolar range. Said variable peptide loop length is, preferably, composed of ten to twenty amino acids, and the scaffold may be any protein having improved solubility and compacity properties, such as thioredoxin-A. Peptide aptamer selection can be made using different systems including, e.g., the yeast two-hybrid system (see e.g., Hoppe-Seyler 2000, J Mol Med. 78 (8): 426-30).

Polypeptides or peptides which bind to the extracellular domain of B-type plexins, preferably, encompass peptides and polypeptides which are derived from ligands or other binding proteins, the B-type plexin itself or ErbB-2. More preferably, a polypeptide to be used as antagonist is the polypeptide of the present invention described elsewhere herein.

The term "B-type plexin" as used herein refers to plexins of the B-type, i.e. plexin B1, plexin B2 and plexin B3. In general, plexins are a family of transmembrane receptors for semaphorins and have been initially characterized in the context of axon guidance in the developing nervous system (Tamagnone 1999, Cell 1999, 99:71-80). Plexin-B1, -B2 and -B3 have been shown to stably interact with ErbB-2 (Swiercz 2004, J Cell Biol 165:869-880). This interaction is critical for activation of the small GTPase RhoA by semaphorin ligands of Plexin-B1 and, thus, for signaling. The amino acid and nucleic acid sequences of plexin B1, B2 and B3 have been described in the art.

Plexin B1 is a 300 kDa member of the B subfamily, Plexin family of Semaphorin receptors. Mature human Plexin B1 is a 2116 amino acid (aa) type I transmembrane (TM) glycoprotein that contains a 1471 aa extracellular domain (ECD) and a 612 aa cytoplasmic region. The ECD contains one Semaphorin (Sema) domain, three PSI domains, and three IPT repeats. The ECD is cleaved into two subunits, a 200 kDa α-chain (aa 20-1305) and a 100 kDa TM β-chain. The subunits are nondisulfide-linked and generate a high-affinity receptor. Plexin B1 is a receptor for Semaphorin 4D/CD100. It forms a receptor complex with Neuropilins, MET, and EGF-R2 (ErbB-2). Multiple splice variants are known.

Preferably, the B-type plexin referred to herein is human plexin-B1 having an amino acid sequence as shown in SEQ ID NO: 2 or being encoded by a nucleic acid sequence as shown in SEQ ID NO: 1. Moreover, the term encompasses variants of said B-type plexins and, in particular, the aforementioned human plexin-B1. Such variants have at least the same essential biological and immunological properties as the specific B-type plexin polypeptide. Variants are deemed to share the same essential biological and immunological properties if they are detectable by the same specific assays referred to in this specification, e.g., by ELISA assays using polyclonal or monoclonal antibodies specifically recognizing the said B-type plexin polypeptides. A preferred assay is described in the accompanying Examples. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 91%, 92%, 93%, 94%, 95%, 96%, 97%, 98%, or 99% identical with the amino sequence of the specific B-type plexin polypeptides. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Preferably, the sequence identity is compared over the entire length of the aligned sequences. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Moreover, the variants referred to herein include fragments of the specific B-type plexin polypeptides or the aforementioned types of variants as long as these fragments have the essential immunological and biological properties as referred to above. Such fragments may be, e.g., degradation products or splice variants of the B-type plexin polypeptides. Further included are variants which differ due to posttranslational modifications such as phosphorylation or myristylation.

The term "ErbB-2" refers to "Epidermal growth factor Receptor 2" and is a member of the epidermal growth factor receptor family. It has also been designated as CD340, HER2/neu or p185. The nucleic acid and amino acid sequences for ErbB-2 are well known in the art for various organisms and have been described in, e.g., Bargmann 1986, Nature 319: 226-230. In addition to the B-type plexins referred to in accordance with the present invention, ErbB-2 has been reported to interact with beta-catenin, Glycoprotein 130, PLCG1, Erbin, MUC1, Grb2, cytosolic heat shock protein 90 kDa alpha, DLG4, PIK3R2, PICK1, beta 4-integrin and SHC1. ErbB-2 is a cell membrane surface-bound receptor tyrosine kinase and is normally involved in the signal transduction pathways leading to cell growth and differentiation. It is thought to be an orphan receptor, with none of the EGF family of ligands able to activate it. However, ErbB receptors, preferably, form homo- and heterodimers upon ligand binding. The human HER2 gene encoding the ErbB-2 receptor is a proto-oncogene located at the long arm of human chromosome 17(17q21-q22). The term "Erb-B2" as used herein, preferably, refers to human ErbB-2 as well as variants thereof. Variants of the human erb-B2 are those having an amino acid sequence which differs due to at least one amino acid substitution, deletion and/or addition wherein the amino acid sequence of the variant is still, preferably, at least 50%, 60%, 70%, 80%, 85%, 90%, 91%, 92%, 93%, 94%, 95%, 96%, 97%, 98%, or 99% identical with the (entire) amino sequence of the human Erb-B2 polypeptide and still have the same biological and/or immunological properties, in particular, are still capable of interacting with a B-type plexin. How such degree of identity can be determined is described elsewhere herein in connection with the B-type plexins.

The term "medicament" as used herein refers, in one aspect, to a pharmaceutical composition containing the antagonist referred to above as pharmaceutical active compound, wherein the pharmaceutical composition may be used for human or non-human therapy of various diseases or disorders in a therapeutically effective dose. The antagonist, preferably, can be present in liquid or lyophilized form. The medicament is, preferably, for topical or systemic administration. Conventionally a medicament will be administered orally, intravenously, intramuscular or subcutaneously. However, depending on the nature and the mode of action of a compound, the medicament may be administered by other routes as well. The antagonist is the active ingredient of the composition, and is, preferably, administered in conventional dosage forms prepared by combining the drug with standard pharmaceutical carriers according to conventional procedures. These procedures may involve mixing, granulating, and compression, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables. A carrier must be acceptable in the sense of being compatible with the other ingredients of the formulation and being not deleterious to the recipient thereof. The pharmaceutical carrier employed may include a solid, a gel, or a liquid. Examples for solid carriers are lactose, terra alba, sucrose, talc, gelatine, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa. A diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like. A therapeutically effective dose refers to an amount of the compound to be used in medicament of the present invention which prevents, ameliorates or treats the symptoms accompanying a disease or condition referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. The medicament referred to herein is administered at least once in order to treat or ameliorate or prevent a disease or condition recited in this specification. However, the said medicament may be administered more than one time. Specific medicaments are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent. The resulting formulations are to be adapted to the mode of administration. Dosage recommendations shall be indicated in the prescribers or users instructions in order to anticipate dose adjustments depending on the considered recipient. The medicament according to the present invention may in a further aspect of the invention comprise drugs in addition to the antagonist of the present invention which are added to the medicament during its formulation. Details on such drugs are to be found elsewhere herein. Finally, it is to be understood that the formulation of a medicament takes place under GMP standardized conditions or the like in order to ensure quality, pharmaceutical security, and effectiveness of the medicament.

In a preferred embodiment of the antagonist of the invention, said antagonist is for use as a medicament for treating metastasizing cancer.

The term "cancer" as used herein refers to any malignant neoplasm. The malignant neoplasms are diseases resulting from the undesired growth, the invasion, and under certain conditions metastasis of impaired cells in a subject. The cells giving rise to cancer are genetically impaired and have usually lost their ability to control cell division, cell migration behavior, differentiation status and/or cell death machinery. Most cancers form a tumor but some hematopoietic cancers, such as leukemia, do not. The cancer in accordance with the present invention shall comprise cancer cells expressing a Erb-B2 polypeptide and a B-type plexin polypeptide as specified elsewhere herein. Preferably, cancer as used herein is metastasizing cancer, and, more preferably, said metastasizing cancer is selected from the group consisting of: breast cancer, ovarian cancer, stomach cancer, and uterine cancer. Symptoms and staging systems for the different cancers are well known in the art and described in standard text books of pathology. Cancer as used herein encompasses any stage, grade, morphological feature, invasiveness, aggressiveness or malignancy of the cancer or the tissue or organ affected thereby.

A subject referred to in accordance with the present invention encompasses animals, preferably mammals, and, more preferably, humans. Preferably, the antagonist of the present invention will be applied for subjects suspected to either suffer from cancer in light of clinically apparent symptoms or subjects suspected to suffer from cancer due to a potential increased predisposition.

In a preferred embodiment of the antagonist of the invention, said antagonist is to be used in said medicament in combination with a compound which is cyto-toxic, which inhibits cell proliferation or differentiation of cancer cells, which induces apoptosis of cancer cells and/or which prevents tumor angiogenesis. Preferably, said compound is selected from the group consisting of: trastuzumab, bevacizumab, tamoxifen, 5-fluorouracil, methotrexate, gemcitabine, Ara-C (Cytarabine), CCNU (Chloroethylcyclohexylnotrisourea), hydroxyurea, adriamycin, mitomycin C, mitoxantrone, doxorubicin, epirubicin, cisplatin, carboplatin, cyclophosphamide, ifosfamide, paclitaxel, docetaxel, vincristine, etoposide, irinotecan, and topotecan.

The present invention, thus, also contemplates a method for treating metastasizing cancer in a subject suffering therefrom comprising the steps of administering to a subject suffering from said metastasizing cancer the aforementioned antagonist in a therapeutically effective amount. Preferably, the antagonist is administered in combination with one of the drugs referred to before.

It has been found in previous studies described in the art that ErbB-2, a metastasis-promoting receptor tyrosine kinase, is overexpressed in about 30% of all breast cancers. However, the signaling events downstream of ErbB-2 which drive cancer cell invasion and metastasis remained incompletely understood. Here the inventors show that overexpression of ErbB-2 leads to activation of the semaphorin receptor Plexin-B1. Plexin-B1 was required for ErbB-2-dependent activation of the pro-metastatic small GTPases RhoA and RhoC and promoted invasive behavior of human breast cancer cells. In a mouse model of ErbB-2-overexpressing breast cancer, ablation of the gene encoding Plexin-B1 strongly reduced the occurrence of metastases, and in human patients with ErbB-2-overexpressing breast cancer low levels of Plexin-B1 expression significantly correlated with good prognosis. Plexin-B1 therefore represents a new therapeutic target in ErbB-2-positive cancers, particularly in ErbB-2-positive breast cancers. Thanks to the findings underlying the present invention, it is possible to prevent metastasis of cancer, and, in particular, breast cancer. Moreover, based on the amount of B-type plexins present on cancer cells, the metastasizing potential can be assessed and a prognosis can be established.

The explanations and definitions of the terms made above apply for the following embodiments mutatis mutandis.

The present invention also refers to the use of a B-type plexin or an antibody specifically binding to a B-type plexin for diagnosing the metastasizing potential of cancer in a sample of a subject.

The amount of a B-type plexin and, preferably, human plexin B1 can be determined in a sample of a subject suspected to suffer from metastasizing cancer (i.e. a cancer which has the potential to metastasize) by techniques well known in the art. Depending on the nature of the sample, the amount may be determined by ELISA based techniques for quantifying the amount of a polypeptide or by quantification of the amount of specifically-bound antibodies in immunehistochemistry of tissue biopsy samples. Moreover, the amount of a B-type plexin may also be determined in accordance with the use of the present invention by measures aiming to detect the amount of transcripts of the B-type plexin gene. Such techniques encompass hybridization techniques such as Northern Blots or PCR-based determination techniques.

In accordance with the aforementioned use of the present invention, it will be understood that the amount of a B-type plexin determined in a sample of a test subject should be compared to a reference amount which indicates whether the test subject suffers from metastasizing cancer, or not. A suitable reference amount may be derived from a subject known to suffer from metastasizing caner. In such a case an amount of the determined B-type plexin in the test sample which is identical or increased with respect to the reference amount in the test sample is indicative for a subject suffering from metastasizing cancer. A test amount which is decreased with respect to the reference amount shall be indicative for a non-metastasizing cancer. Alternatively, a suitable reference amount may be derived from a subject known not to suffer from metastasizing caner. In such a case an amount of the determined B-type plexin in the test sample which is identical or decreased with respect to the reference amount in the test sample is indicative for a subject having non-metastasizing cancer while an increased amount is indicative for a subject suffering from metastasizing cancer.

Accordingly, the present invention also contemplates a method for diagnosing whether a cancer in a subject has metastasizing potential, or not, comprising the steps of (a) determining the amount of a B-type plexin and, preferably, human plexin B1, in a sample of a subject suspected to suffer from metastasizing cancer and comparing the determined amount to a reference amount whereby it is diagnosed whether a cancer has metastasizing potential, or not. For determining the amount of a B-type plexin in a sample of a subject, for example, the monoclonal antibodies of the invention can be used.

The present invention contemplates a method for identifying an antagonist which prevents the interaction of a B-type plexin with ErbB-2 comprising the steps of:
   a) contacting a compound suspected to be an antagonist which prevents the interaction of a B-type plexin with ErbB-2 with a cell comprising the B-type plexin and Erb-B2 under conditions which allow for prevention of the interaction of the B-type plexin and Erb-B2; and
   b) determining whether the compound is capable of preventing the interaction of said B-type plexin and Erb-B2, whereby the compound is identified as an antagonist which prevents the interaction of the B-type plexin with ErbB-2, if the interaction has been prevented.

The term "contacting" as used herein refers to bringing the compound suspected to be an antagonist into physical contact with a cell comprising the B-type plexin and Erb-B2. The compound shall be brought into contact for a time and under conditions sufficient to allow for interaction of the compound with its target in the cell so that the interaction of the B-type plexin and the ErbB-2 can be prevented. Suitable conditions and a suitable time can be selected by the skilled artisan dependent on the chemical nature of the antagonist. It will be understood that an antagonist which directly prevents interaction by binding to, e.g., the B-type plexin may prevent the interaction much faster than an antagonist who indirectly acts via inhibition of transcription of the B-type plexin gene or translation of its transcripts in the cell.

Determining whether the compound is capable of preventing the interaction of said B-type plexin and Erb-B2 can be done by determining a suitable readout which physiologically occurs in the cell as a response upon binding between the B-type plexin to the ErbB-2. Suitable readouts are described elsewhere herein and encompass, e.g., measuring tyrosine phosphorylation of the B-type plexin or RhoA and/or C activity as described in the accompanying Examples, below. Preferably, the interaction is also determined by determining cell mobility and/or invasion properties. In order to identify an antagonist, the readout of a cell which has been contacted to the compound suspected to be the antagonist should be compared to a cell which has not been contacted to the said compound. A prevention of the interaction can be determined by a reduction of the measured readout.

It will be understood that in the aforementioned method of the present invention, the cell is, preferably, treated in order to stimulate the interaction between the B-type plexin and the ErbB-2. The interaction can be, preferably, stimulated by semaphorin. Alternatively, the interaction may be stimulated by overexpressing ErbB-2 in the cell or by expressing a constitutively active mutein of ErbB-2. Details are described in the accompanying Examples.

Compounds which can be used in the method of the present invention for identifying antagonists are those which are referred to as potential antagonists elsewhere in this specification, in particular, siRNA, micro RNA, antisense RNA, morpholino oligonucleotides, ribozymes, triple helix forming agents, antibodies, aptameres, peptides and polypeptides or small molecules.

Analogously, the invention contemplates for a method for identifying an antagonist which prevents the interaction of a B-type plexin with its ligand, for example, the interaction of plexin-B1 with Sema4D.

Also encompassed by the present invention is a polynucleotide encoding a B-type plexin polypeptide which lacks a functional intracellular domain.

A B-type plexin which lacks a functional intracellular domain can be generated by introducing a deletion of one or more amino acids of the intracellular domain or by mutating one or more amino acids of the intracellular domain of the B-type plexin. Suitable B-type plexin muteins encoded by the polynucleotide of the present invention can be tested by the method of the present invention for antagonistic activity. The structures of the B-type plexins have been described elsewhere herein. Most preferably, the polynucleotide of the invention encodes a plexin B1 which lacks the intracellular domain and amino acids of the transmembrane domain, i.e. the amino acids corresponding to amino acids 1512 to 2135 of the human plexin shown in SEQ ID NO: 2.

The term "polynucleotide" as used herein refers to single- or double-stranded DNA molecules as well as to RNA molecules. Encompassed by the said term is genomic DNA, cDNA, hnRNA, mRNA as well as all naturally occurring or artificially modified derivatives of such molecular species. The polynucleotide may be in an aspect a linear or circular molecule. Moreover, in addition to the nucleic acid sequences encoding the aforementioned B-type plexin mutant polypeptide, a polynucleotide of the present invention may comprise additional sequences required for proper transcription and/or translation such as 5'- or 3'-UTR sequences.

Moreover, the present invention relates to a vector comprising the polynucleotide of the present invention. Preferably, the said vector is an expression vector.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotide of the present invention, in an aspect, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. Moreover, in an aspect of the invention, the polynucleotide is operatively linked to expression control sequences allowing expression in prokaryotic or eukaryotic host cells or isolated fractions thereof in the said vector. Expression of the polynucleotide comprises transcription of the polynucleotide into a translatable mRNA. Regulatory elements ensuring expression in host cells are well known in the art. In an aspect, they comprise regulatory sequences ensuring initiation of transcription and/or poly-A signals ensuring termination of transcription and stabilization of the transcript. Additional regulatory elements may include transcriptional as well as translational enhancers.

Possible regulatory elements permitting expression in prokaryotic host cells comprise, e.g., the lac-, trp- or tac-promoter in E. coli, and examples for regulatory elements permitting expression in eukaryotic host cells are the AOX1- or the GAL1-promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen) or baculovirus-derived vectors. Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotide or vector of the invention into targeted cell population. Methods which are well known to those skilled in the art can be used to construct recombinant viral vectors; see, for example, the techniques described in Sambrook, "Molecular Cloning A Laboratory Manual", Cold Spring Harbor Laboratory (1989) N.Y. and Ausubel, Current Protocols in Molecular Biology, Green Publishing Associates and Wiley Interscience, N.Y. (1994).

The present invention contemplates a host cell comprising the polypeptide, the polynucleotide, or the vector of the present invention.

The term "host cell" as used herein encompasses prokaryotic and eukaryotic host cells. Preferably, the host cell is a bacterial cell, an animal host cell or a fungal host cell. Preferably, the said bacterial host cell is an E. coli host cell. An animal host cell, preferably, is a cell of an animal cell line suitable for production of proteins or a fungal host cell such as a yeast host cell.

The present invention also relates to a polypeptide encoded by the polynucleotide of the present invention.

Such a polypeptide can be used as an antagonist according to the present invention as set forth elsewhere herein in detail.

All references cited in this specification are herewith incorporated by reference with respect to their entire disclosure content and the disclosure content specifically mentioned in this specification.

FIGURES

FIG. 1: Overexpression of wildtype ErbB-2 or constitutively-active ErbB-2 results in phosphorylation and activation of Plexin-B1. (A) HEK293 cells were transfected with VSV-Plexin-B1 and constitutively-active ErbB-2 (ErbB-2 VE) or wildtype ErbB-2 (ErbB-2 WT). After incubation without (−) or with (+) 150 nM Sema4D for 20 min, VSV-Plexin-B1 was immunoprecipitated (IP) using an anti-VSV-antibody and precipitates were immunoblotted (IB) using anti-phosphotyrosine (pTyr) or anti-VSV antibodies. (B-E) HEK293 cells were transfected with VSV-Plexin-B1 as well as MYC-RhoA and FLAG-PDZ-RhoGEF (B), HA-RhoB and FLAG-PDZ-RhoGEF (C), HA-RhoC and FLAG-PDZ-RhoGEF (D) or HA-R-Ras and Rnd1 (E). Where indicated, cells were additionally transfected with constitutively-active ErbB-2 (ErbB-2 VE), wildtype ErbB-2 (ErbB-2 WT), or a Plexin-B1 deletion construct which lacks the intracellular domain (P1xB1ΔC). After incubation without or with 150 nM Sema4D for 20 min, the indicated active Rho isoforms or R-Ras were precipitated (pulldown) as described in the Examples, and precipitates were immunoblotted (IB) using antibodies directed against the tags of the Rho proteins or R-Ras.

Figure 2:
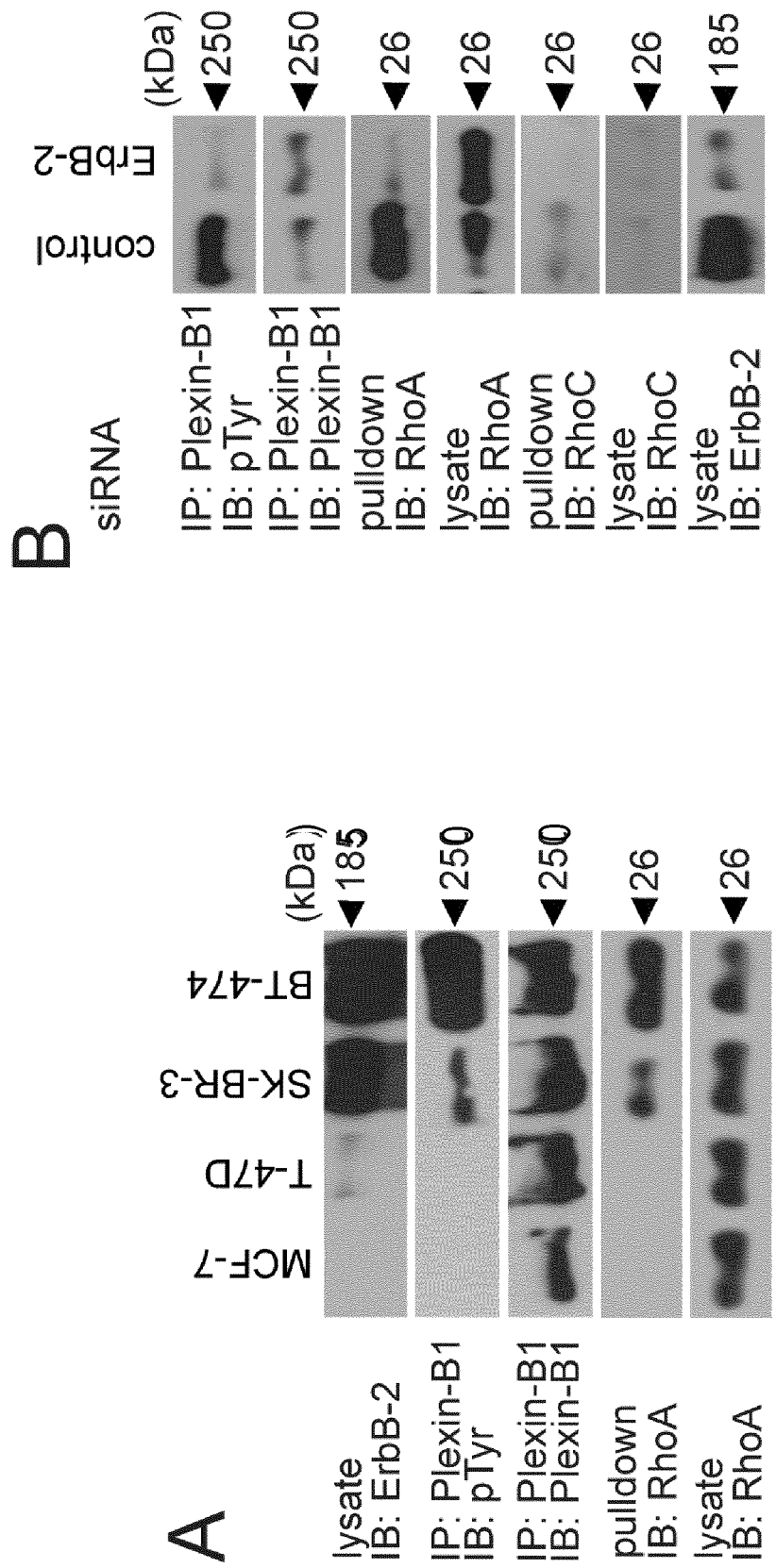
Figure 2:
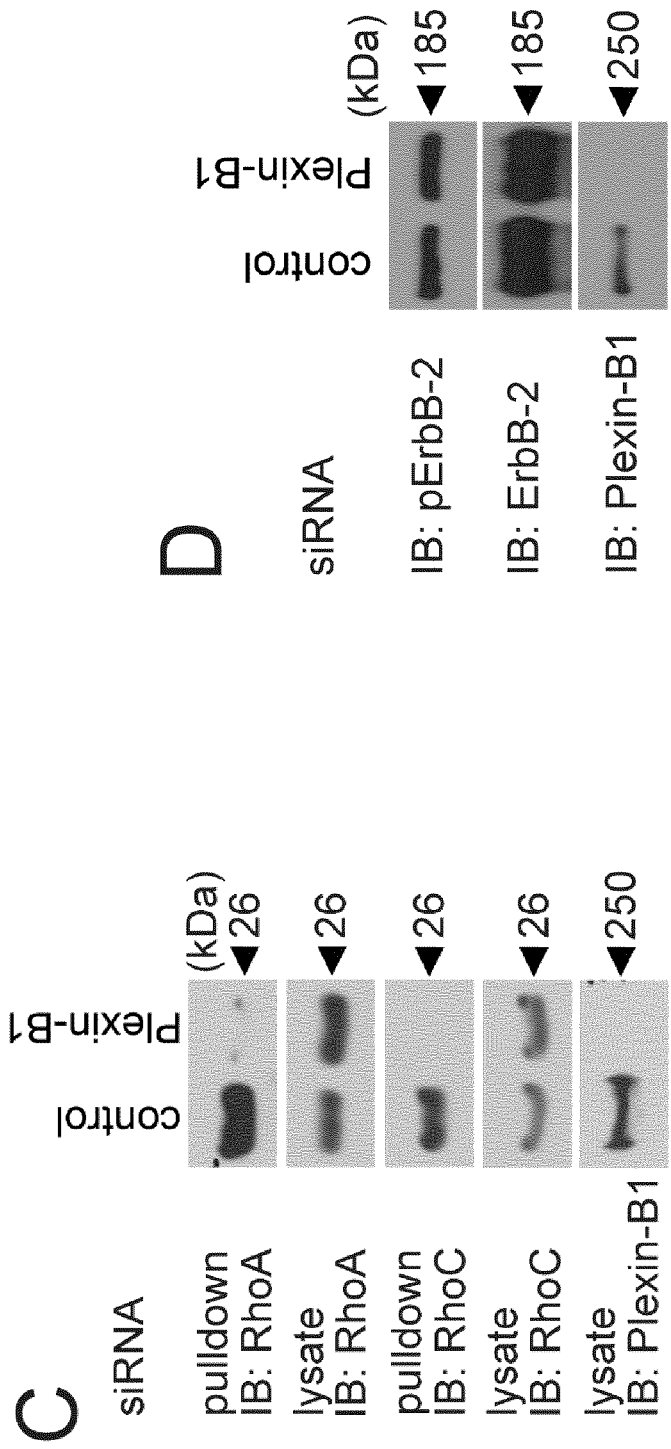
Figure 2:
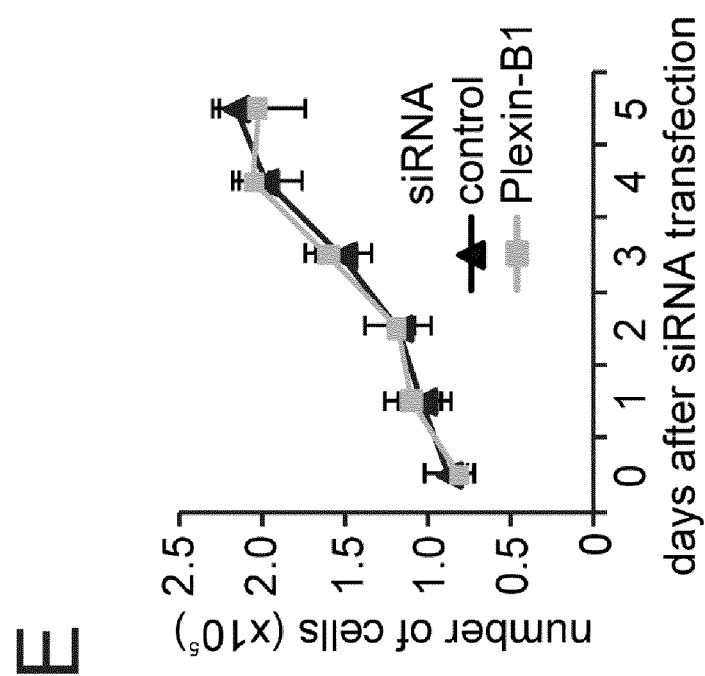
Figure 2:
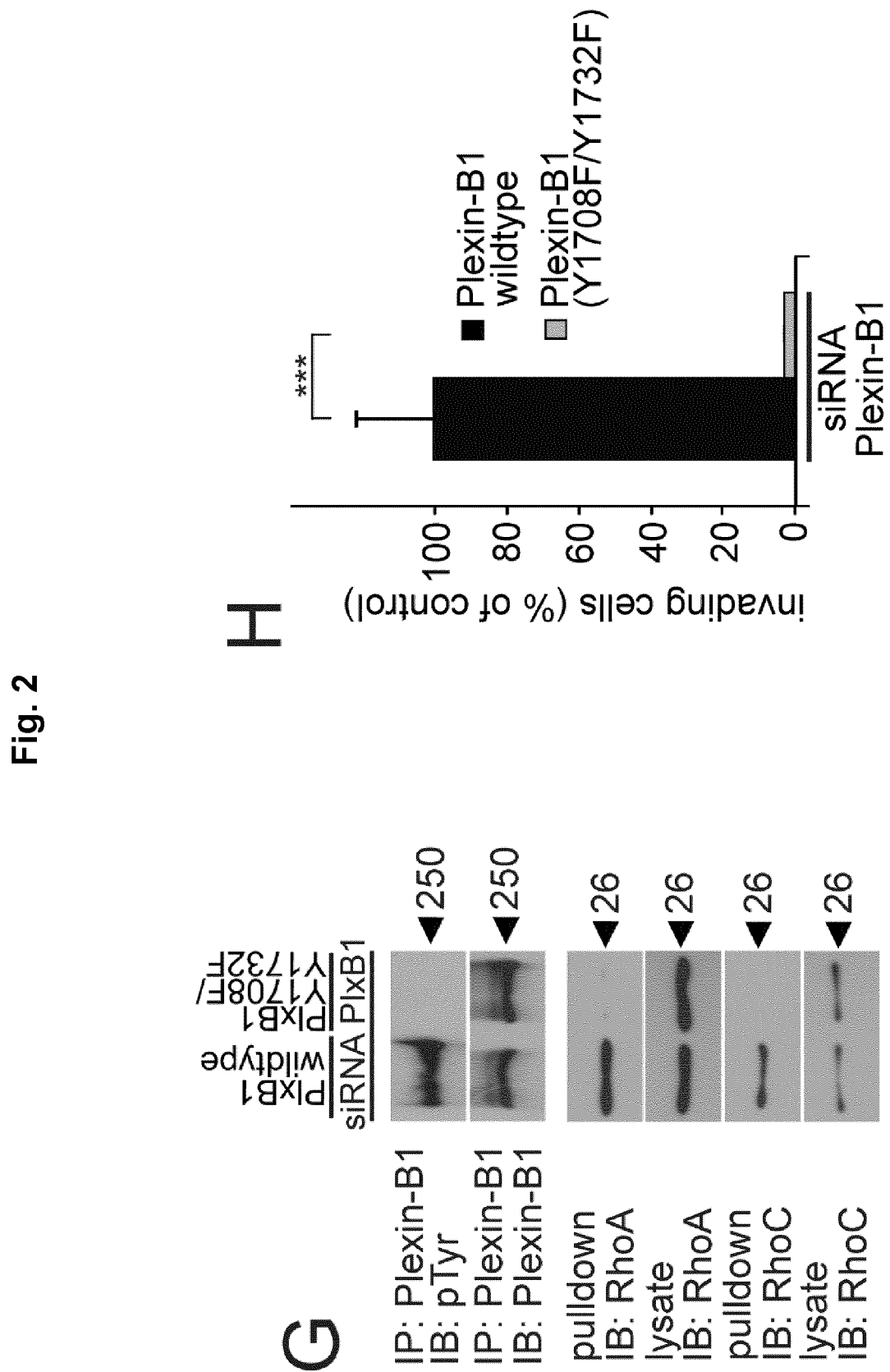
Figure 2:
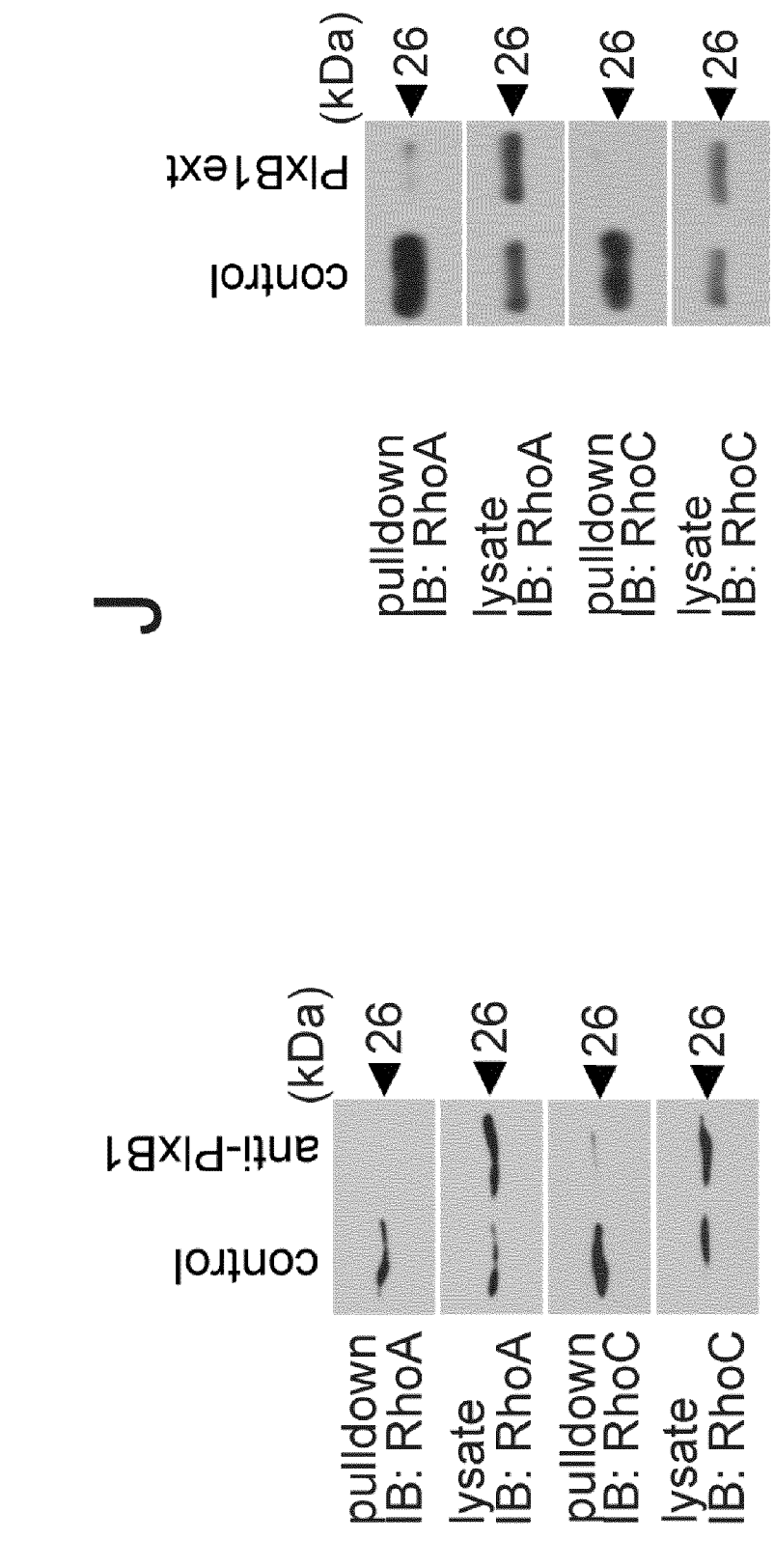
Figure 2:
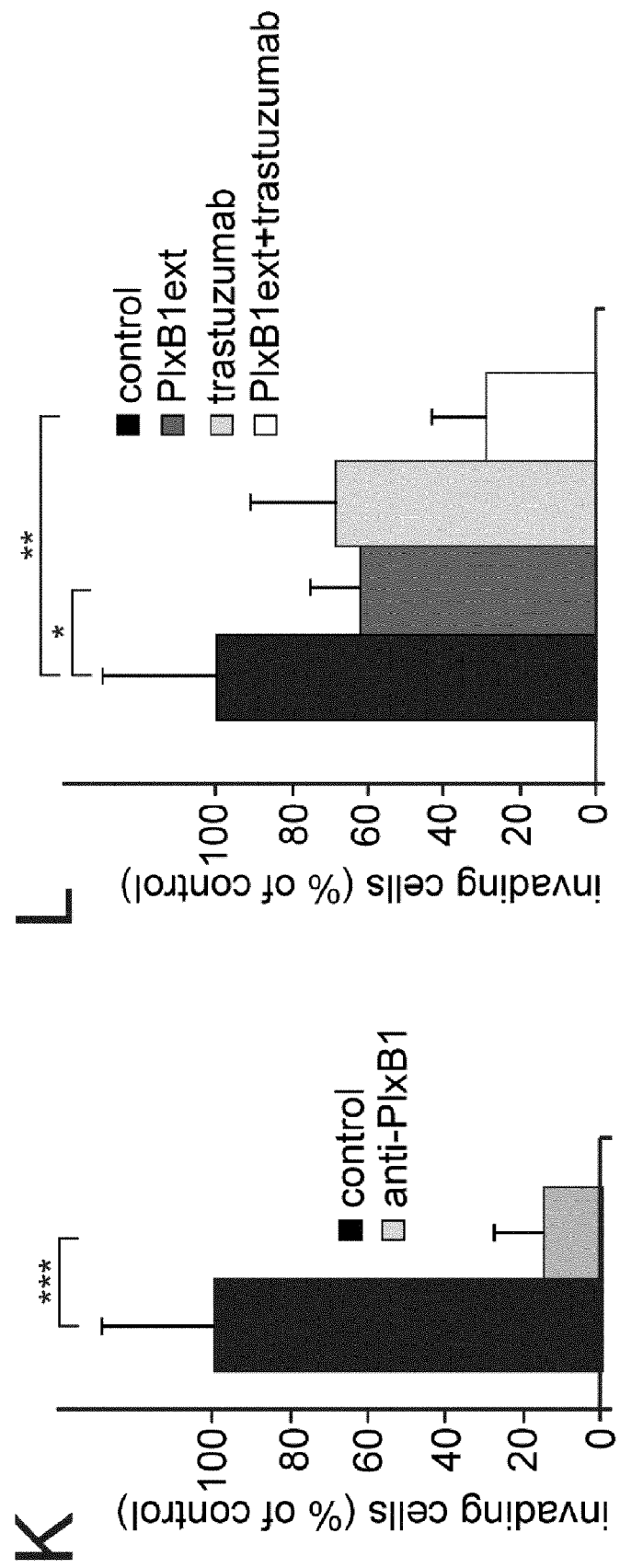

FIG. 2: Plexin-B1 promotes invasion of ErbB-2-overexpressing human breast cancer cells. (A) Human breast cancer cell lines MCF-7, T-47D, SK-BR-3, BT-474 or (B) BT-474 cells transfected with control siRNA or siRNA against ErbB-2 were lysed, Plexin-B1 was immunoprecipitated (IP) and precipitates were immunoblotted (IB) using anti-phospho-tyrosine (pTyr) or anti-Plexin-B1 antibodies. In a parallel experiment, levels of active RhoA/RhoC were determined. (C-F) BT-474 cells were transfected with control or Plexin-B1 siRNA. (C) The amount of Plexin-B1 and active RhoA/RhoC was determined. (D) Cell lysates were probed with an anti-phospho-ErbB-2[Y1248]-antibody. (E) Numbers of BT-474 cells were counted on 5 consecutive days. (F) Cells were seeded onto Matrigel-coated filters and invading cells were counted as described in the Examples. (G, H) BT-474 cells stably expressing siRNA-insensitive wildtype Plexin-B1 or siRNA-insensitive mutant Plexin-B1 (Y1708F/Y1732F) were transfected with Plexin-B1 siRNA to knockdown endogenous Plexin-B1. (G) Plexin-B1 was immunoprecipitated, and precipitates were immunoblotted using anti-Plexin-B1 and anti-phospho-tyrosine (pTyr) antibodies. In addition, levels of active RhoA/RhoC were determined. (H) In parallel, cells were seeded onto Matrigel-coated filters and invading cells were counted. (I, J) BT-474 cells were incubated (I) without or with a mouse monoclonal anti-Plexin-B1 antibody (anti-P1xB1; clone #93, 1.8 ng/µl) or (J) without or with 150 nM P1xB1ext (i.e. the soluble extracellular domain of Plexin-B1) and the amounts of active RhoA/RhoC were determined. (K, L) BT-474 cells were seeded onto Matrigel-coated filters in (K) the absence or presence of a mouse monoclonal anti-Plexin-B1 antibody (anti-P1xB1; clone #93, 1.8 ng/µl) or (L) the presence of 150 nM P1xB1 ext, 2 µg/ml trastuzumab or both and invading cells were counted. Data are presented as mean±S.D.

Figure 3:
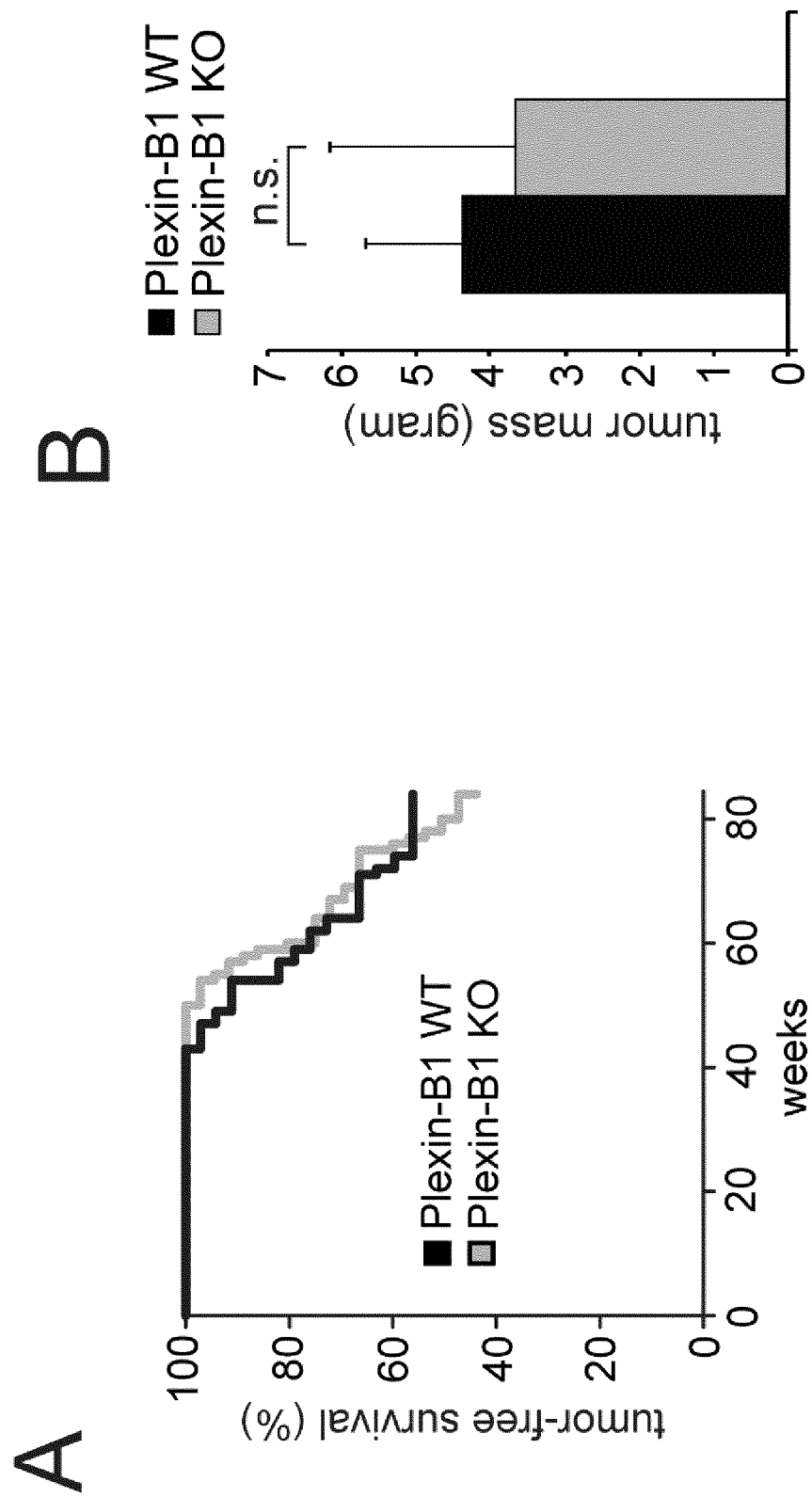
Figure 3:
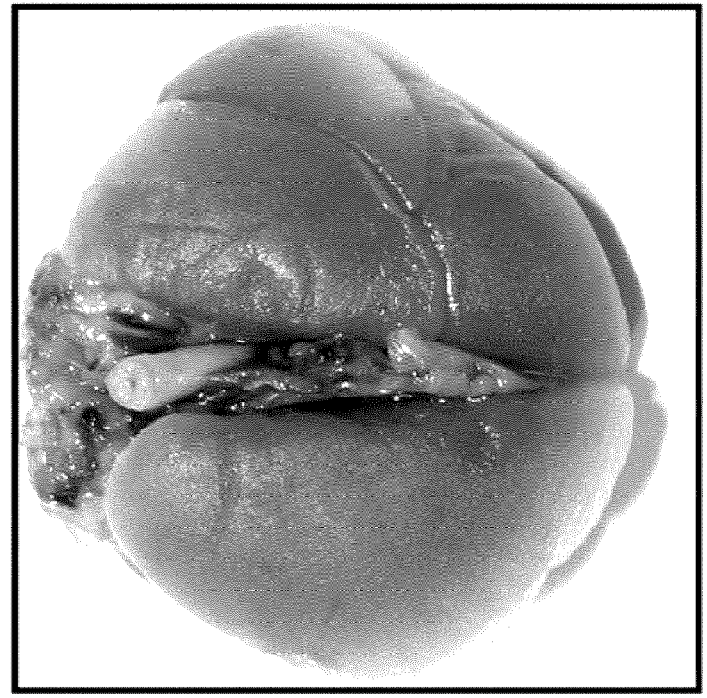
Figure 3:
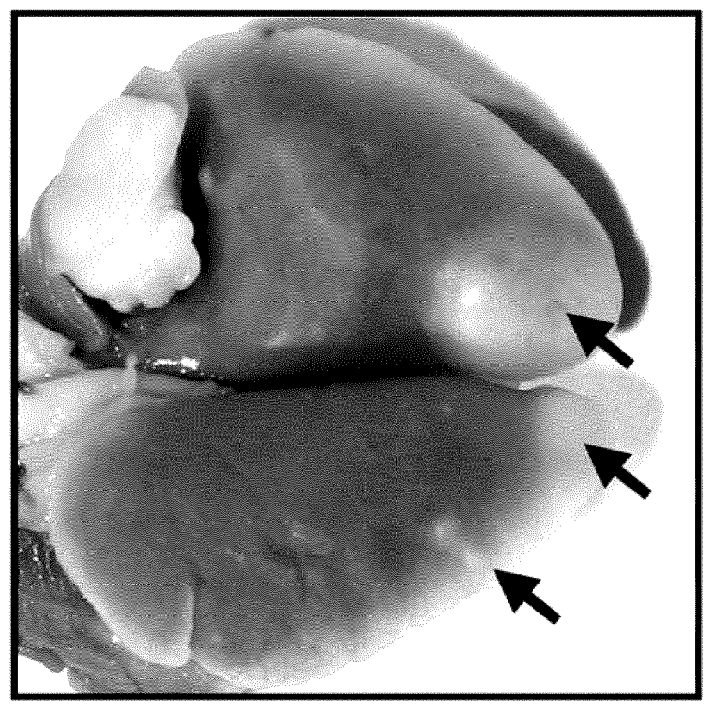
Figure 3:
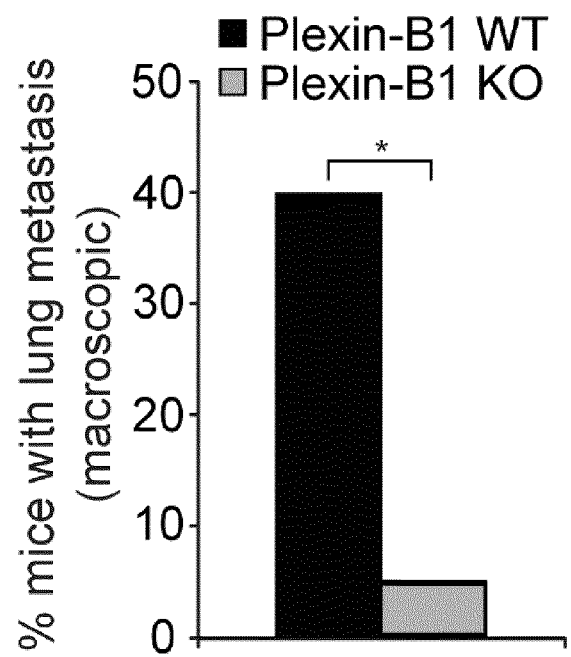
Figure 3:
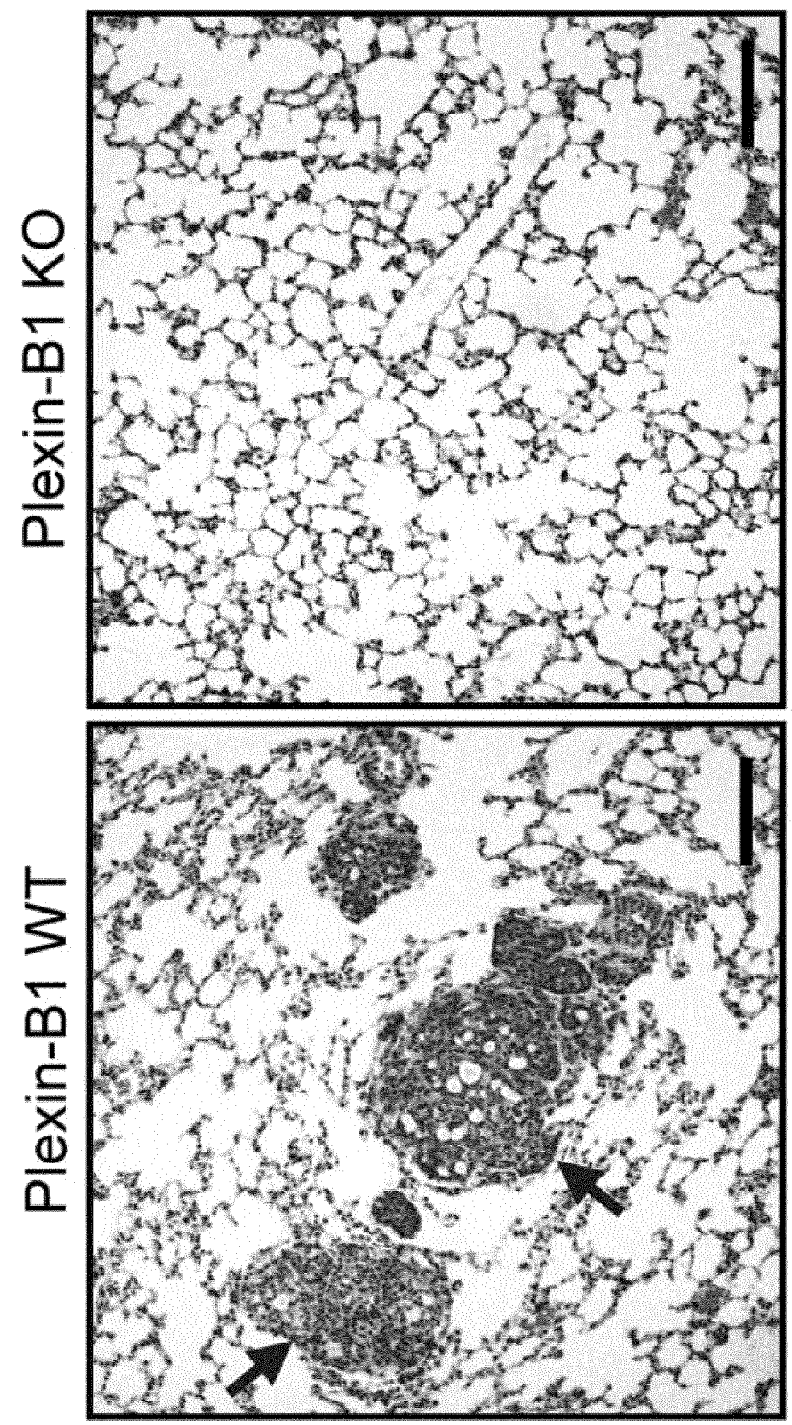
Figure 3:
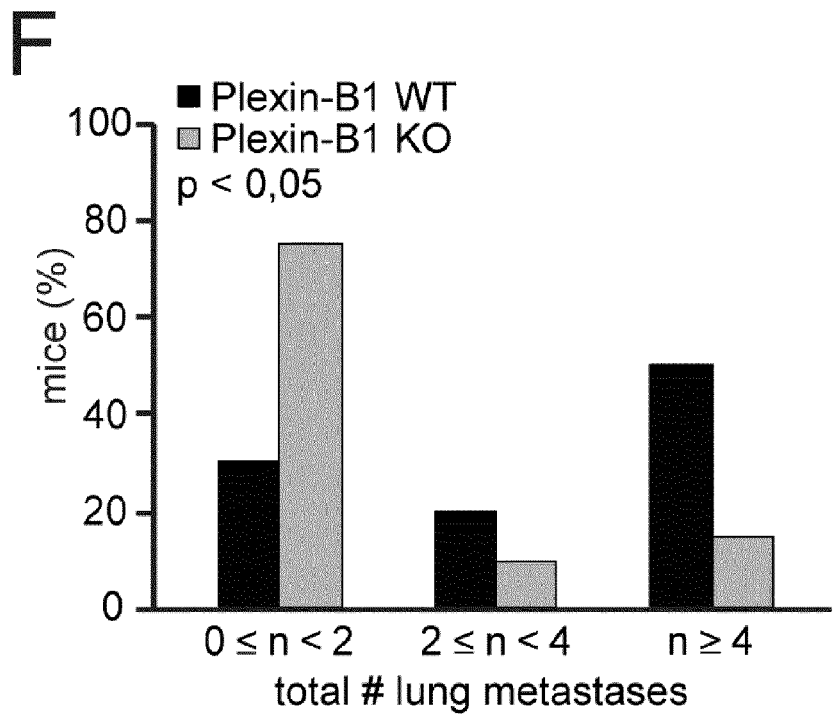
Figure 3:
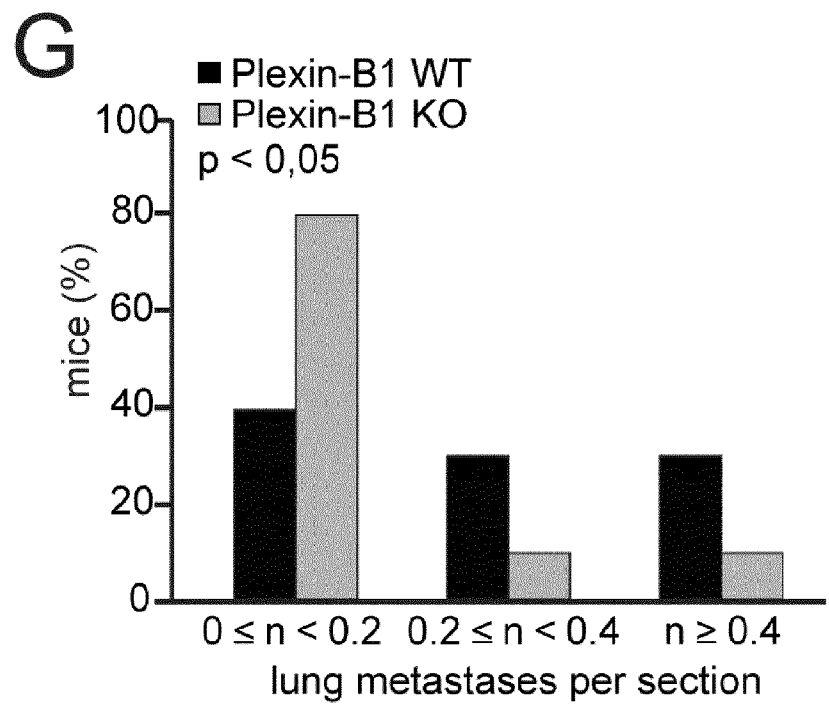

FIG. 3: Plexin-B1 promotes metastasis in a mouse model of ErbB-2-overexpressing breast cancer. (A) MMTVneu; p1xnb1$^{+/+}$ mice (WT) and MMTVneu;p1xnb1$^{-/-}$ mice (KO) were examined weekly for the appearance of mammary tumors. Shown is the percentage of tumor-free survival plotted against time. WT, n=37; KO, n=40. (B) 8.5 weeks after the first appearance of a palpable tumor, mice were sacrificed, and tumors were excised and weighed. Data are presented as mean±S.D. (C) Macroscopic images of the lungs of tumor-bearing MMTVneu;p1xnb1$^{+/+}$ mice (WT) and MMTVneu; p1xnb1$^{-/-}$ mice (KO). Metastases are indicated by arrows. (D) Quantification of the results in (C). (E) Microscopic images of H&E stained histological sections of tumor-bearing mice. Metastases are indicated by arrows. (F-G) Lung sections of tumor-bearing mice were microscopically analyzed, and the number of metastases per lung (F) and the number of metastases per histological section (G) were counted. Statistical significances were determined by log-rank test (A), t-test (B,F,G) and Fisher's exact test (D); *, p≤0.05; n.s., not significant. Scale bars in (E) represent 100 µm.

Figure 4:
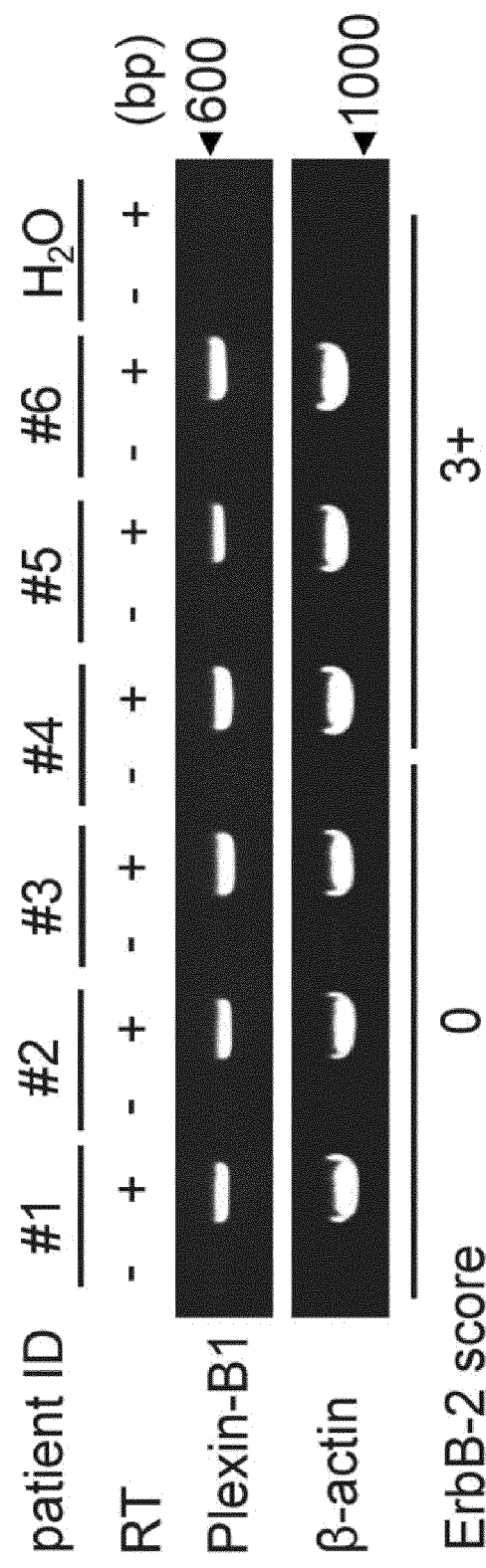
Figure 4:
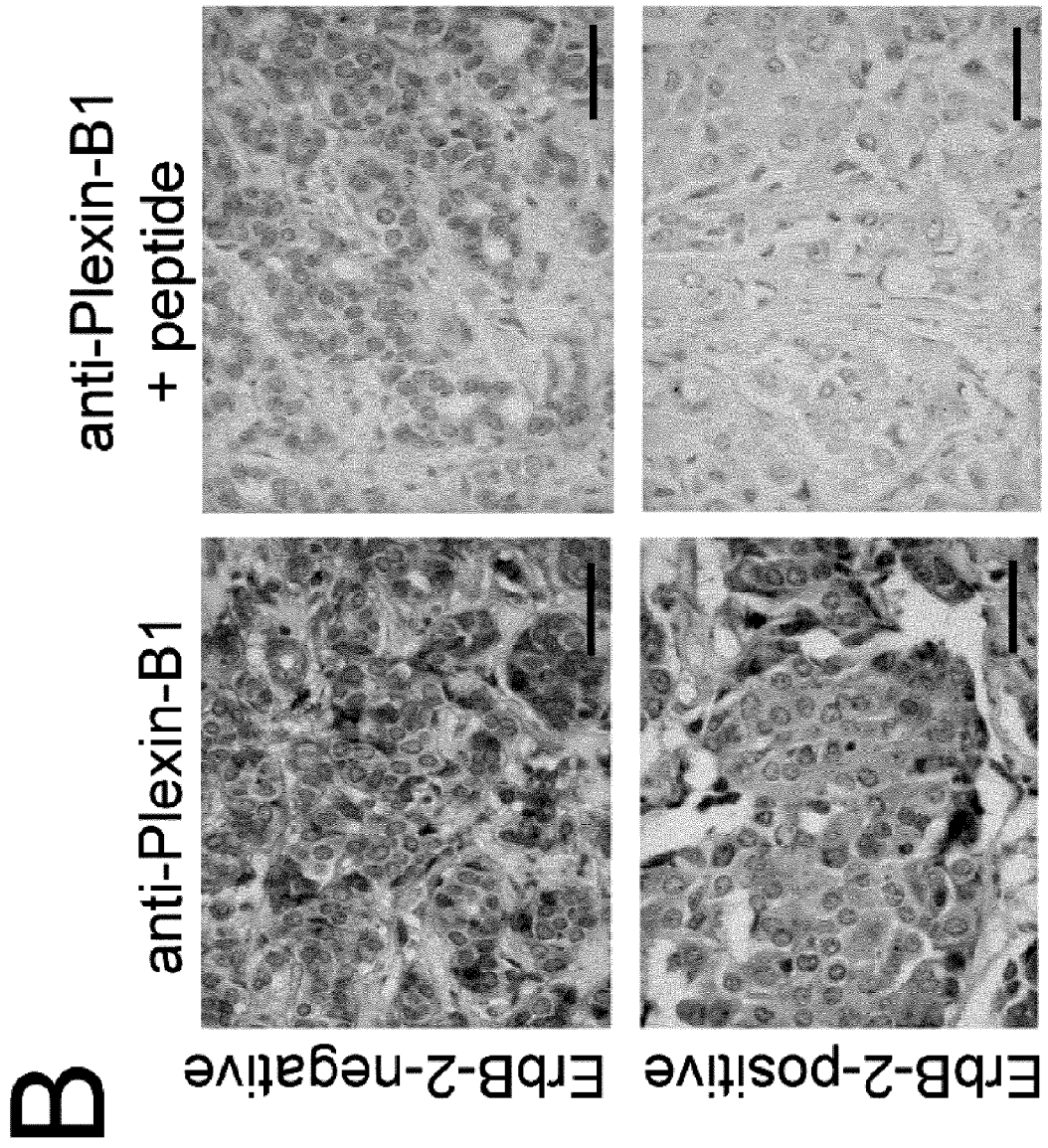
Figure 4:
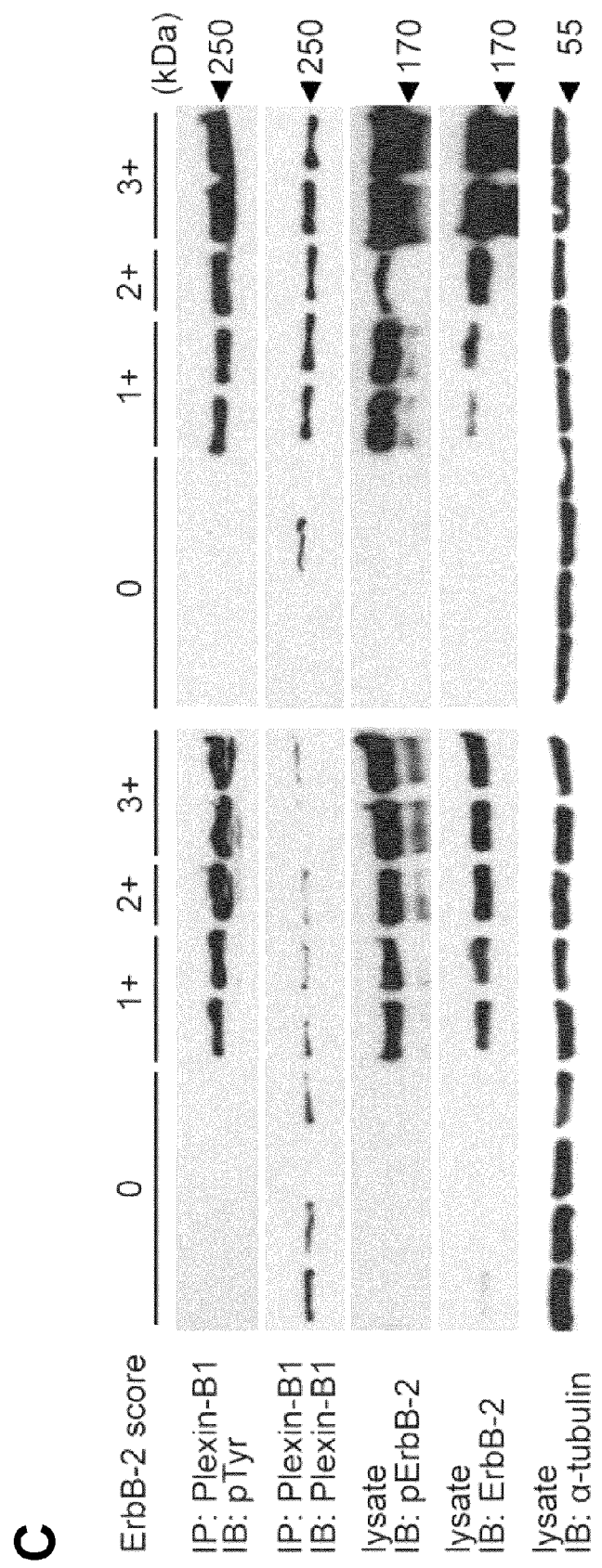
Figure 4:
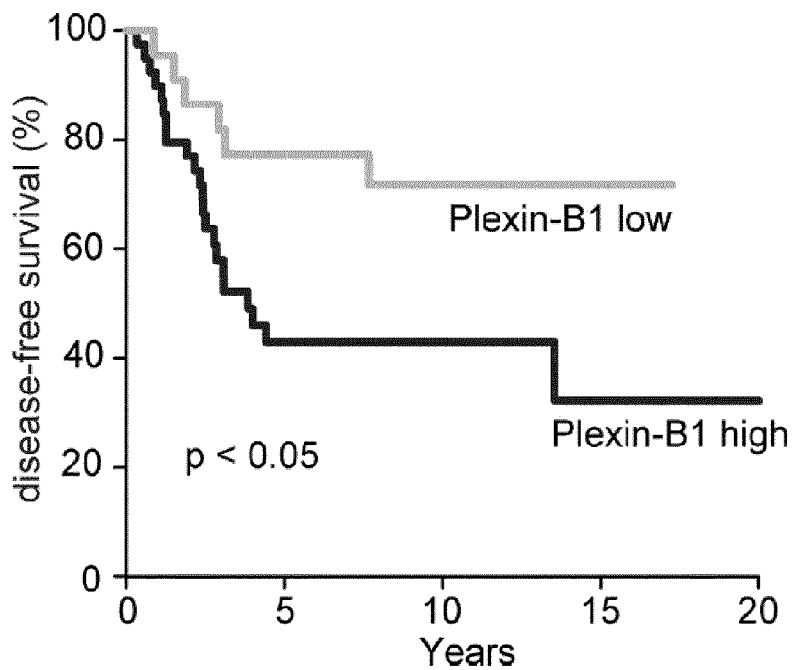
Figure 4:
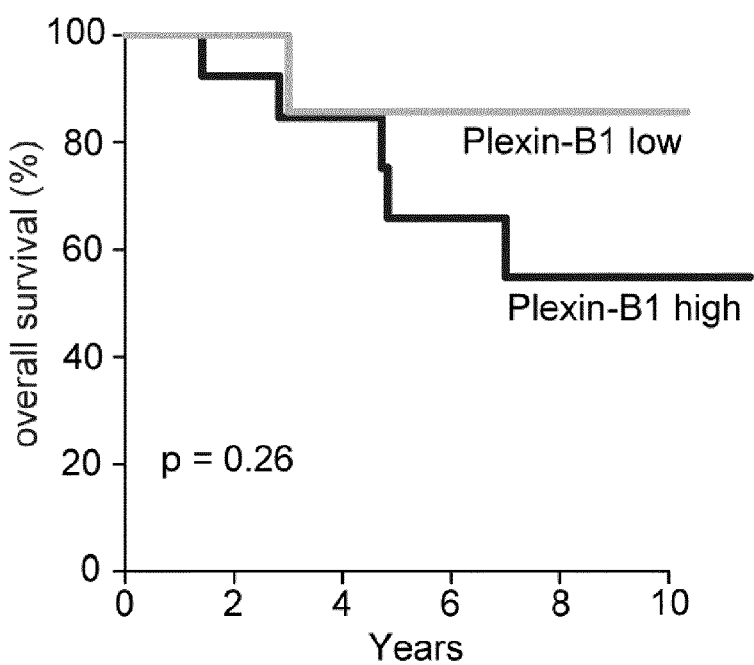
Figure 4:
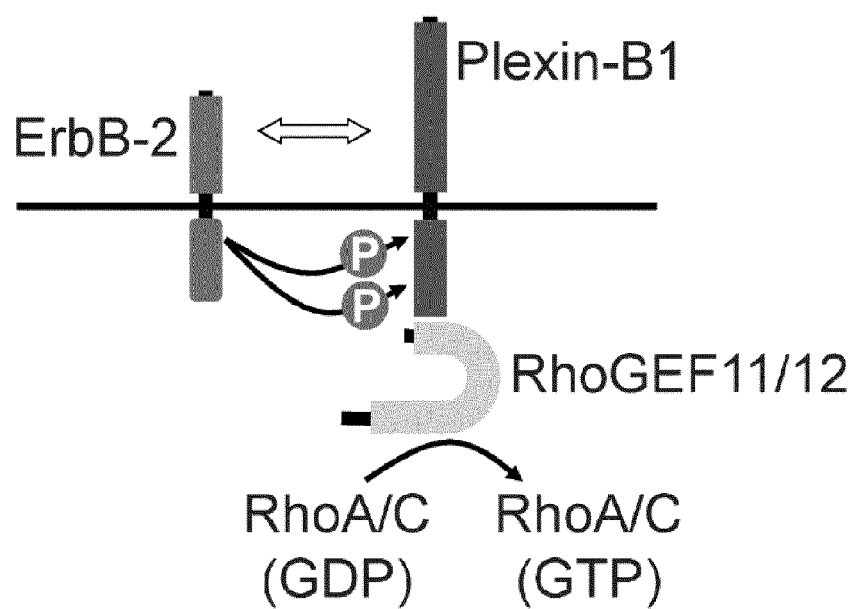

FIG. 4: Plexin-B1 is activated in ErbB-2-positive human breast cancer, and its expression level correlates with prognosis of patients. (A) RNA of tumor specimens from breast cancer patients without detectable ErbB-2 expression (ErbB-2 score 0) or with ErbB-2 overexpression (ErbB-2 score 3+) was isolated and reverse transcribed (RT, reverse transcriptase). PCR analysis was performed using primers specific for Plexin-B1. (B) Immunohistochemical staining of human breast cancer tissues shows that Plexin-B1 protein is expressed in cancer cells. The staining can be blocked by preincubation of the anti-Plexin-B1 antibody (R&D Systems) with the peptide used for immunization. (C) Breast cancer tissues from 18 different patients without detectable ErbB-2 expression (ErbB-2 score 0) or different levels of ErbB-2 expression (ErbB-2 score 1+ to 3+) were lysed. Plexin-B1 was immunoprecipitated (IP), and precipitates were immunoblotted using anti-phospho-tyrosine (pTyr) or anti-Plexin-B1 antibodies. Lysates were probed for ErbB-2, phospho-ErbB-2[Y1248], and α-tubulin. (D) Kaplan-Meier graph representing the disease-free survival of patients with ErbB-2-overexpressing breast cancer. Black, high Plexin-B1 expression (Plexin-B1 high; n=39); grey, low Plexin-B1 expression (Plexin-B1 low; n=22). (E) Kaplan-Meier graph representing the overall survival of patients with ErbB-2-overexpressing breast cancer. Black, high Plexin-B1 expression (Plexin-B1 high; n=13); grey, low Plexin-B1 expression (Plexin-B1 low; n=7). Scale bars in (B) represent 50 µm. (F) Schematic illustration of the ErbB-2/Plexin-B1 signaling pathway. Overexpression of the receptor tyrosine kinase ErbB-2 results in phosphorylation of Plexin-B1 at two specific tyrosine residues. This phosphorylation of Plexin-B1 promotes the activation of RhoA and RhoC via RhoGEF 11 (PDZ-RhoGEF) and RhoGEF 12 (LARG) which stably interact with the C-Terminus of Plexin-B1.

Figure 5:
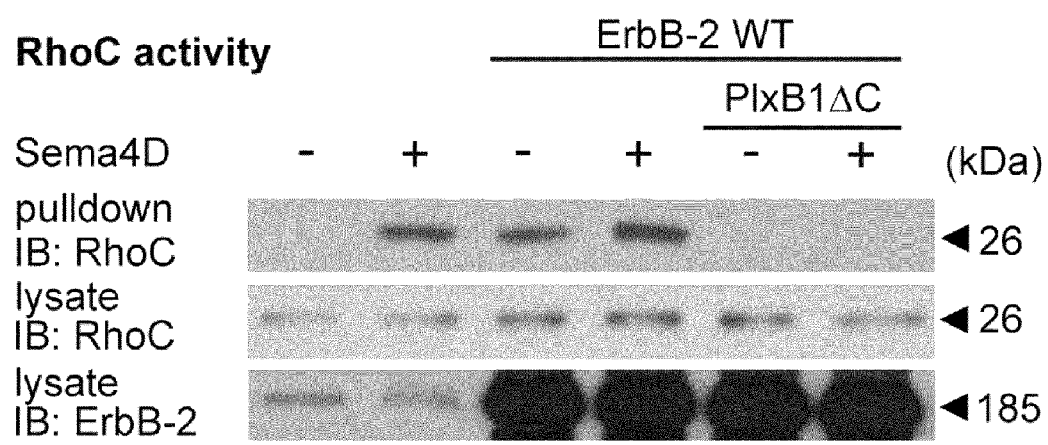

FIG. 5: Activation of RhoC downstream of ErbB-2 is mediated by Plexin-B1. HEK293 cells were transfected with VSV-Plexin-B1 as well as HA-RhoC and FLAG-PDZ-RhoGEF. Where indicated, cells were additionally transfected with wildtype ErbB-2 (ErbB-2 WT), or a Plexin-B1 deletion construct which lacks the intracellular domain (P1xB1ΔC). After incubation without or with 150 nM Sema4D for 20 min, active RhoC was precipitated (pulldown) and precipitates were immunoblotted (IB) using an anti-HA-antibody.

Figure 6:
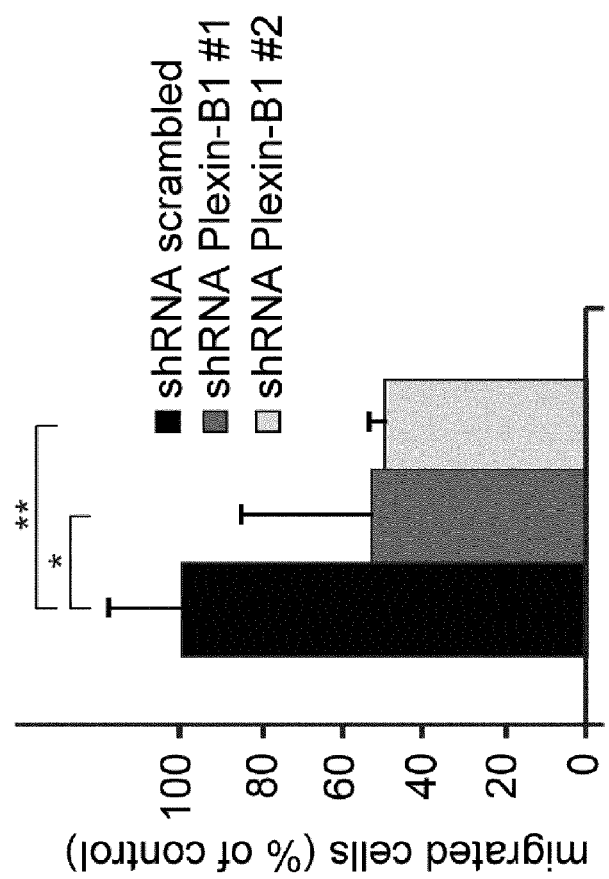
Figure 6:
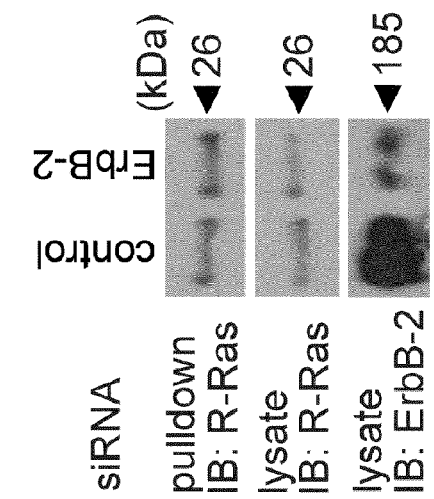
Figure 6:
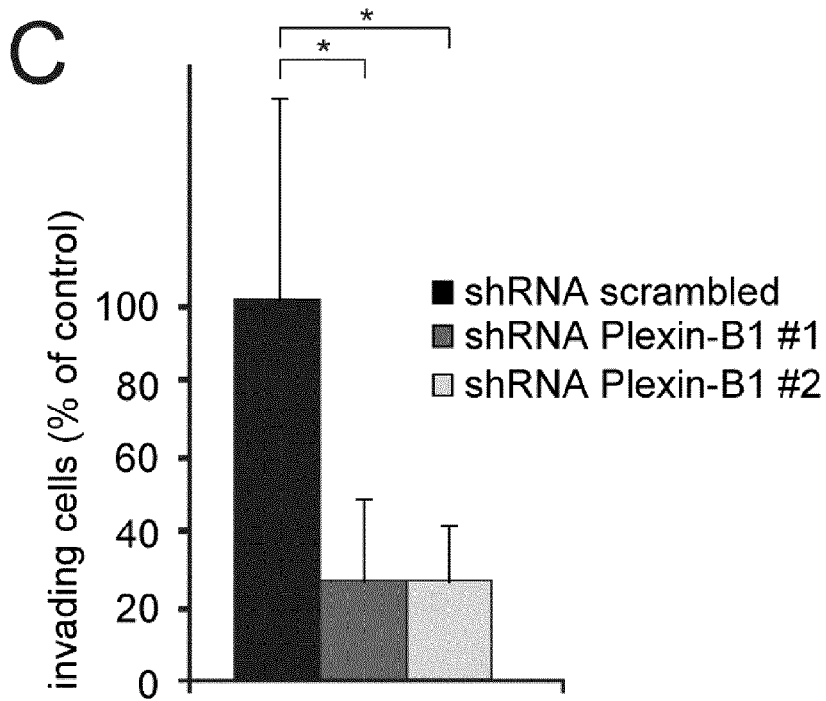
Figure 6:
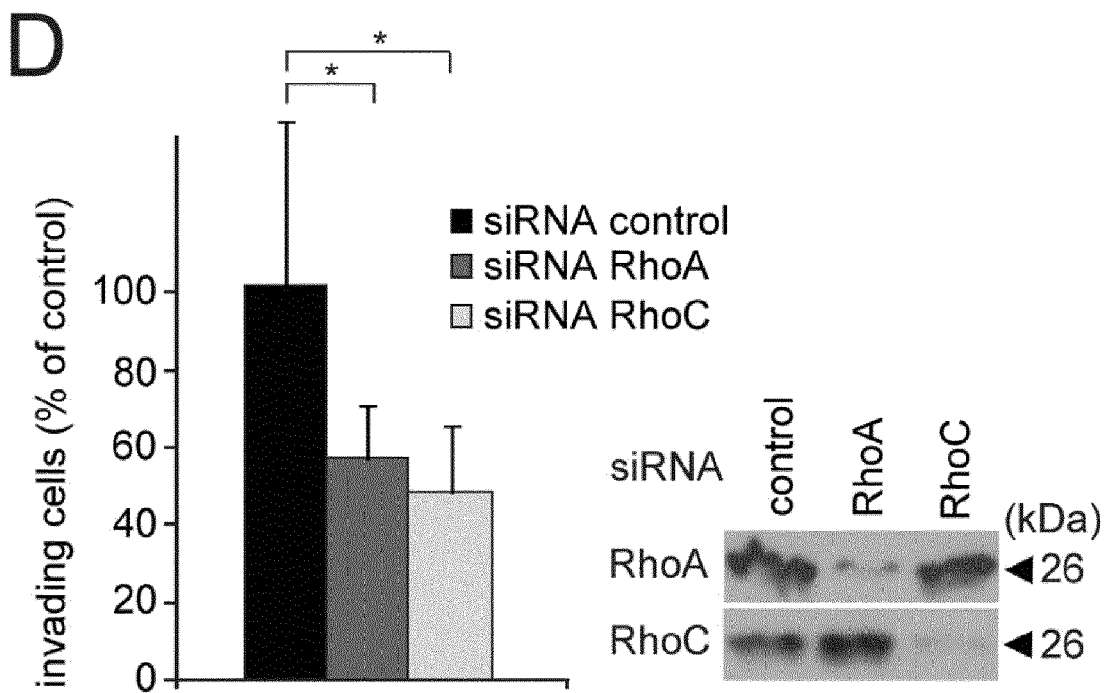
Figure 6:
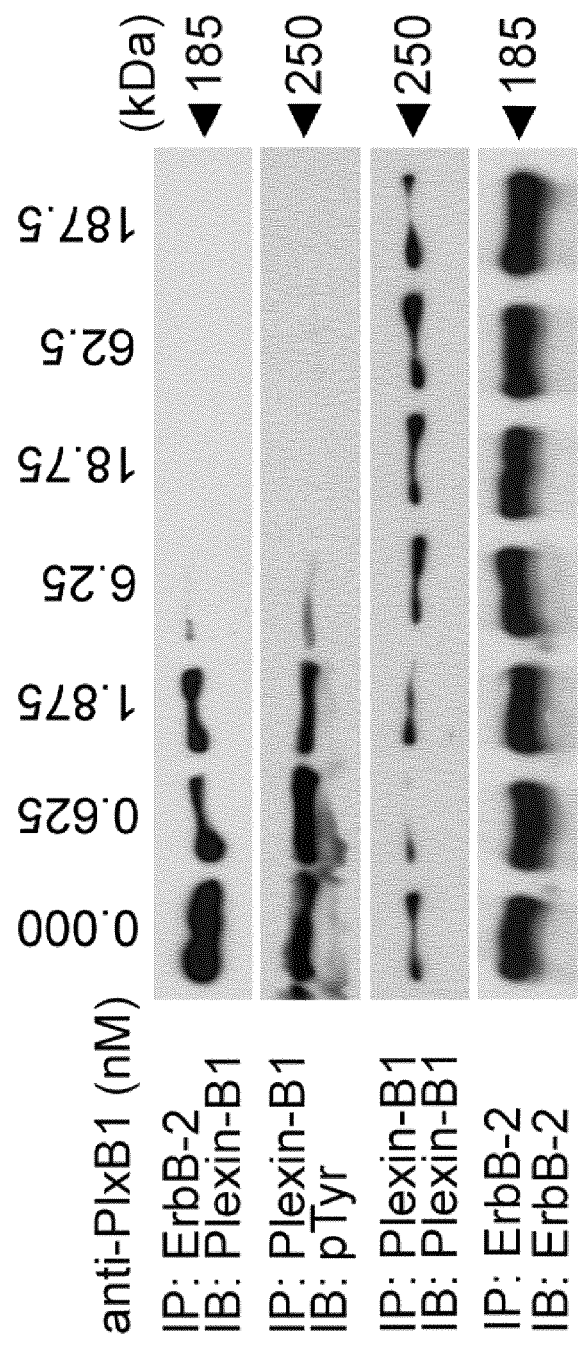
Figure 6:
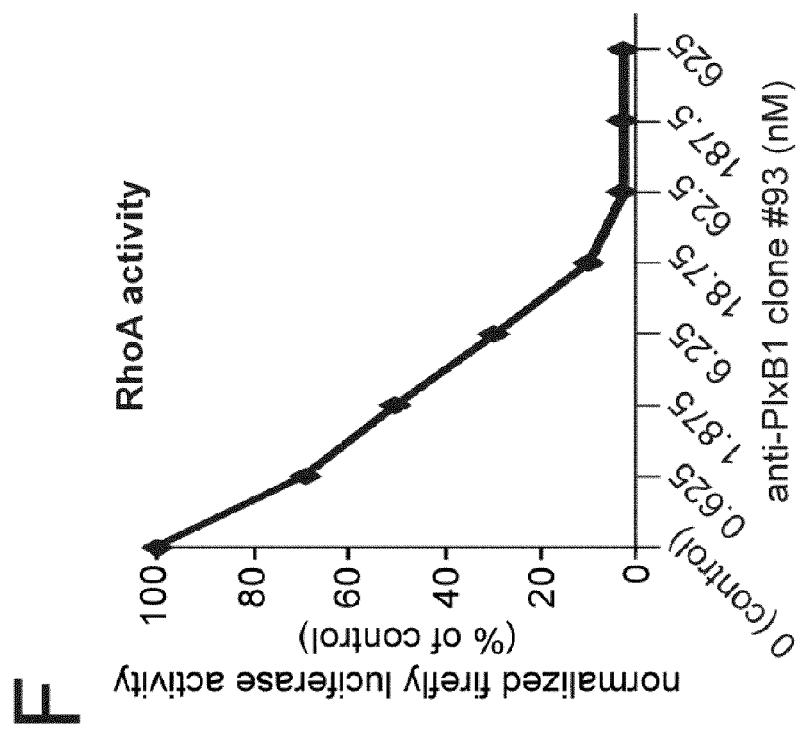
Figure 6:
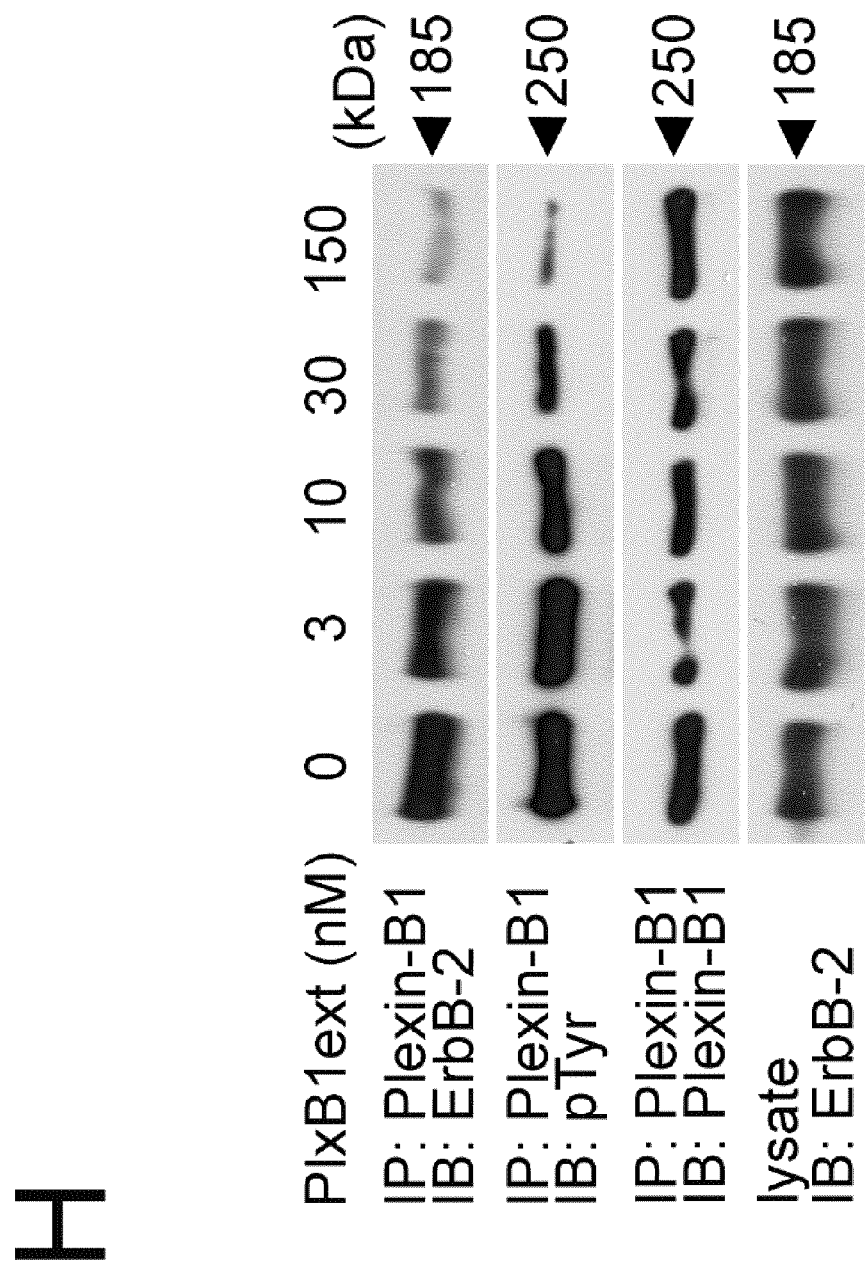

FIG. 6: (A) Knockdown of ErbB-2 does not affect active R-Ras levels. BT-474 cells were transfected with control or ErbB-2 siRNA. 48 h later, cells were lysed, active R-Ras was immunoprecipitated (pulldown) and precipitates were immunoblotted using an anti-R-Ras antibody. (B-C) Stable knockdown of Plexin-B1 impairs migration and invasion of BT-474 cells. Using a lentiviral system, BT-474 cells were stably transfected with control shRNA or shRNAs directed against Plexin-B1. (B) 24 h after seeding onto non-coated filters or (C) 48 h after seeding onto Matrigel-coated filters, cells on the upper side of the filters were removed and cells on the bottom side of the filter were counted as described in the Examples. (D) SiRNA-mediated knockdown of RhoA or RhoC reduces invasiveness of BT-474 cells. BT-474 cells transfected with control, RhoA or RhoC siRNA were seeded onto Matrigel-coated filters. 48 h later, non-invading cells were removed and invading cells were counted. (E-H) The mouse monoclonal anti-Plexin-B1 antibody (clone #93) interferes with the interaction between ErbB-2 and Plexin-B1, but does not inhibit binding of Sema4D to Plexin-B1. Uncoupling of ErbB-2 and Plexin-B1 by the mouse monoclonal anti-Plexin-B1 antibody (clone #93) or the soluble extracellular domain of Plexin-B1 (P1xB1 ext) reduces tyrosine phosphorylation of Plexin-B1. (E) BT-474 cells were incubated with the indicated concentrations of a mouse monoclonal anti-Plexin-B1 antibody (anti-P1xB1; clone #93) for 60 min. Thereafter, cells were lysed, ErbB-2 was immunoprecipitated using an anti-ErbB-2 antibody (IP) and Plexin-B1 was immunoprecipitated using an anti-Plexin-B1 antibody (R&D Systems; IP). Precipitates were immunoblotted (IB) with antibodies directed against Plexin-B1 (R&D Systems), phospho-tyrosine (pTyr), or ErbB-2. (F) HEK293 cells were transfected with 3DA.Luc and plasmids encoding Plexin-B1 and PDZ-RhoGEF. 3DA.Luc represents a reporter plasmid expressing firefly luciferase under the control of a mutant serum response element (SRE) which is activated downstream of active RhoA. After incubation with the indicated concentrations of the mouse monoclonal anti-Plexin-B1 antibody (clone #93) for 60 min, cells were treated with 150 nM Sema4D for 4 h and firefly luciferase activity corresponding to RhoA activity was determined as described in Example 1. (G) MCF-7 cells expressing endogenous Plexin-B1 were incubated with the indicated concentrations of the mouse monoclonal anti-Plexin-B1 antibody (clone #93) for 1 hour. After washing with PBS, cells were treated with myc-Sema4D for 30 min. After removal of unbound myc-Sema4D by washing, cells were incubated with an HRP-conjugated anti-myc antibody for 30 min, washed, and HRP-activity was determined as described in the Examples. (H) BT-474 cells were incubated with the indicated concentrations of the soluble extracellular domain of Plexin-B1 (P1xB1ext) for 45 min. Thereafter, cells were lysed, Plexin-B1 was immunoprecipitated using an anti-Plexin-B1 antibody (R&D Systems; IP) and precipitates were immunoblotted (IB) with antibodies directed against Plexin-B1 (R&D Systems), phospho-tyrosine (pTyr), or ErbB-2.

Figure 7:
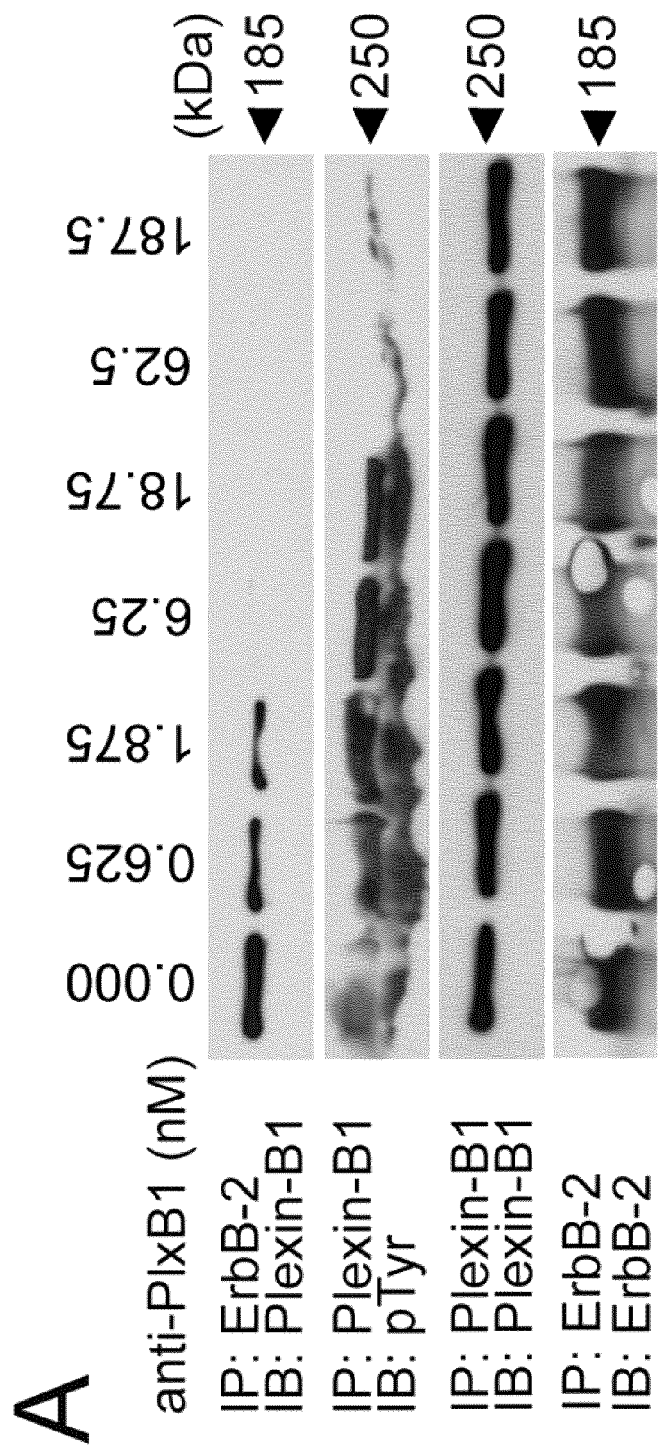
Figure 7:
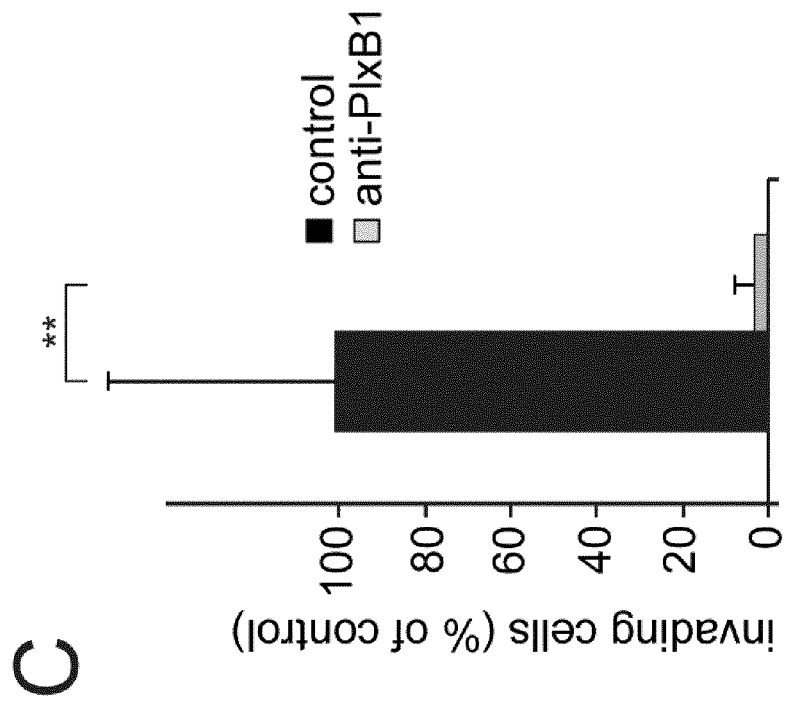
Figure 7:
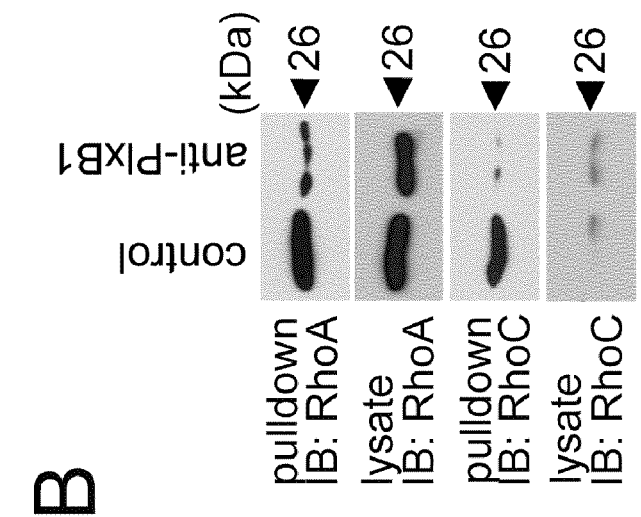

FIG. 7: Plexin-B1 promotes invasion of ErbB-2-overexpressing human ovarian cancer cells. (A) SK-OV-3 cells were incubated with the indicated concentrations of a mouse monoclonal anti-Plexin-B1 antibody (anti-P1xB1; clone #93) for 60 min. After cell lysis ErbB-2 was immunoprecipitated using an anti-ErbB-2 antibody (IP) and Plexin-B1 was immunoprecipitated using an anti-Plexin-B1 antibody (R&D Systems; IP). Precipitates were immunoblotted (IB) with antibodies directed against phospho-tyrosine (pTyr), ErbB-2 or Plexin-B1. (B) SK-OV-3 cells were incubated without or with a mouse monoclonal anti-Plexin-B1 antibody (anti-P1xB1; clone #93, 1.8 ng/µl) for 60 min. Thereafter, cells were lysed and the amounts of active RhoA and RhoC were determined as described (pulldown). (C) SK-OV-3 cells were seeded onto Matrigel-coated filters in the absence or presence of a mouse monoclonal anti-Plexin-B1 antibody (anti-P1xB1; clone #93, 1.8 ng/µl). 16 h later, non-invading cells were removed, and invading cells were counted. Data are presented as mean±S.D. with statistical significances determined by t-test; **, $p \leq 0.01$.

Figure 8:
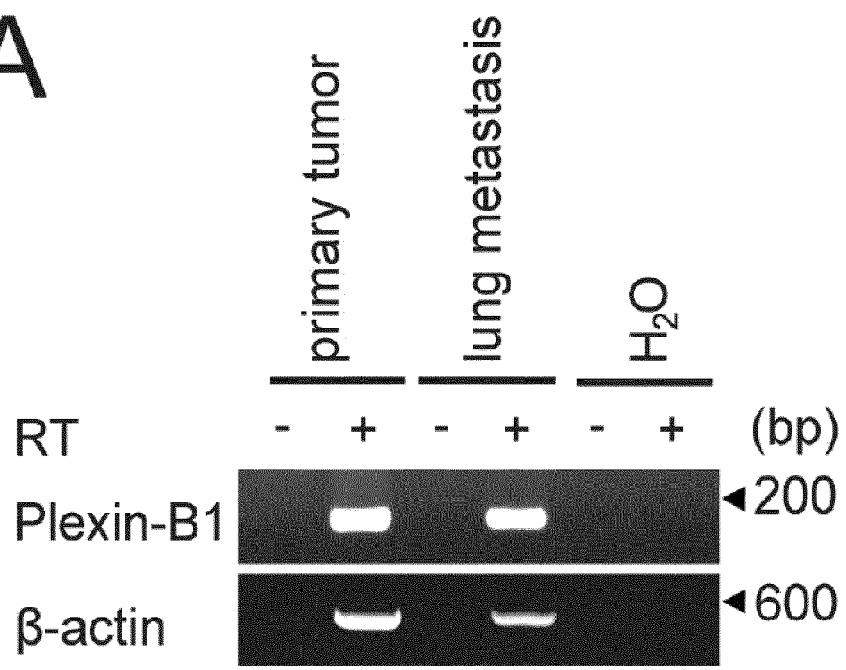
Figure 8:
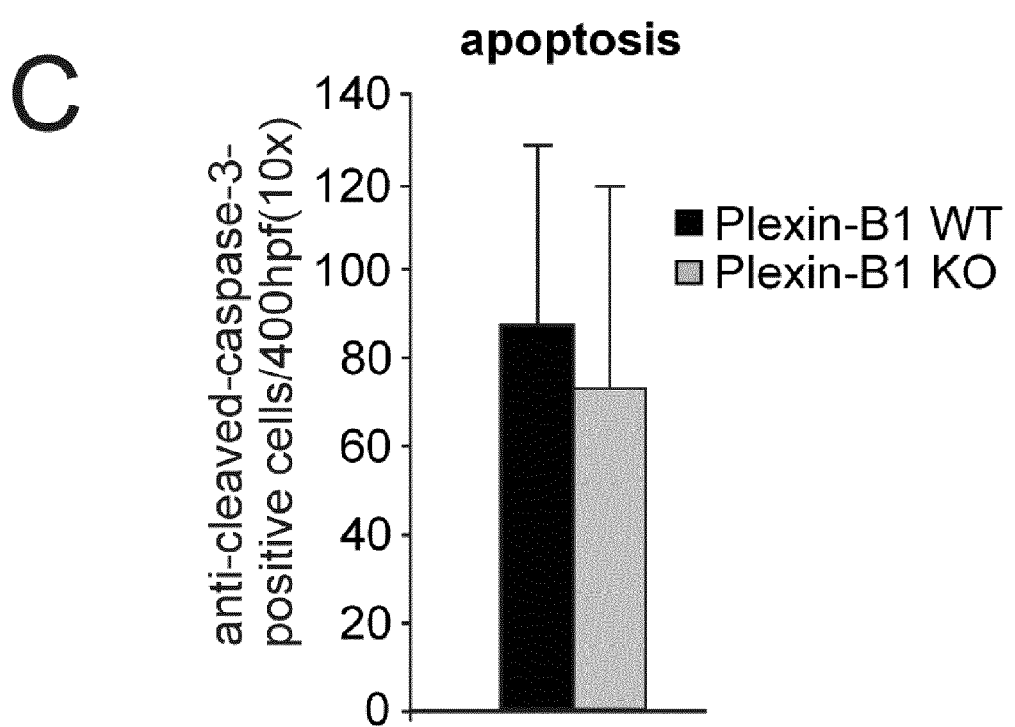
Figure 8:
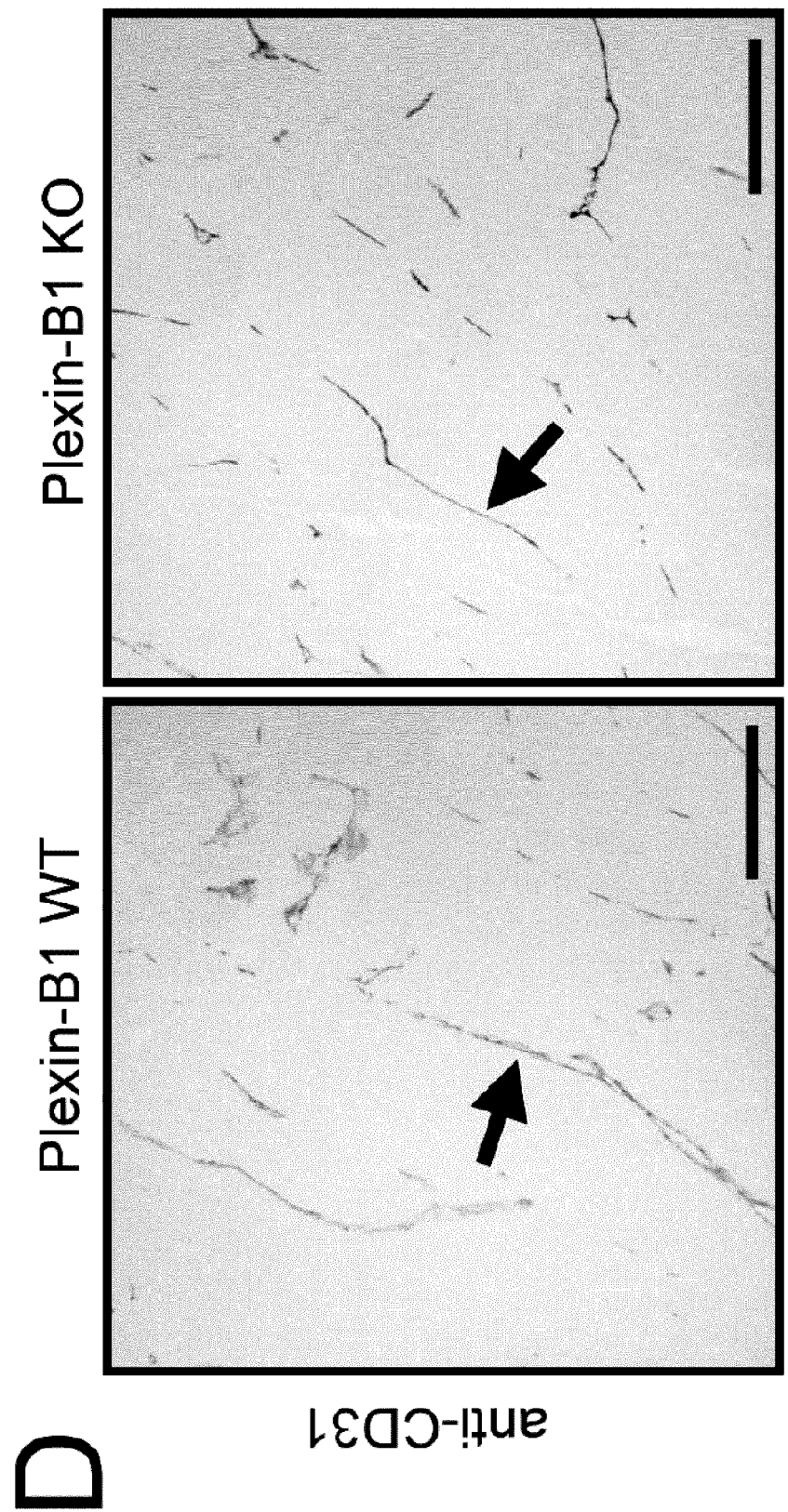
Figure 8:
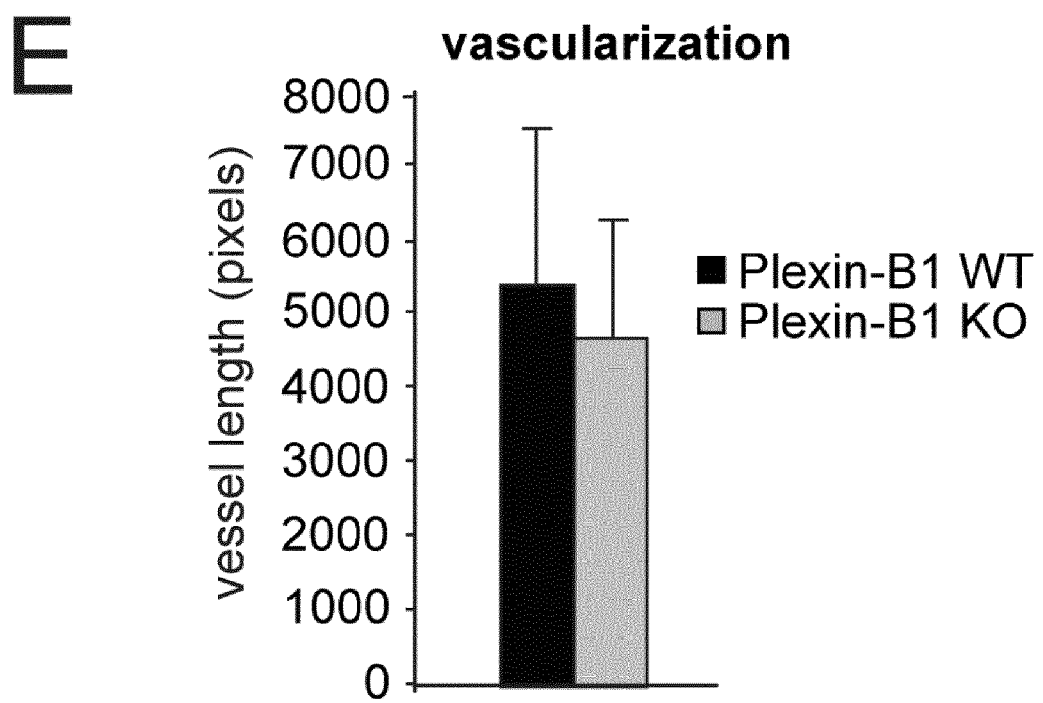
Figure 8:
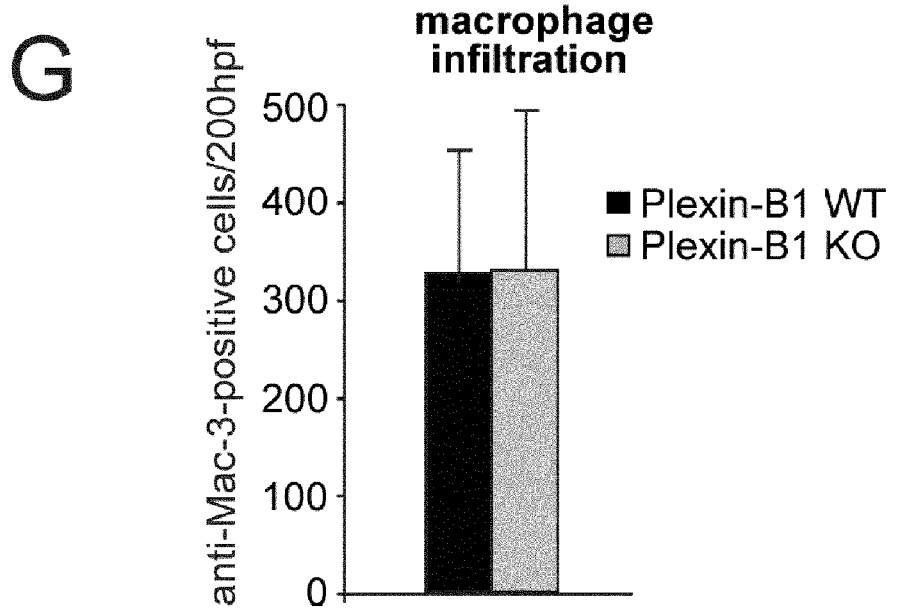
Figure 8:
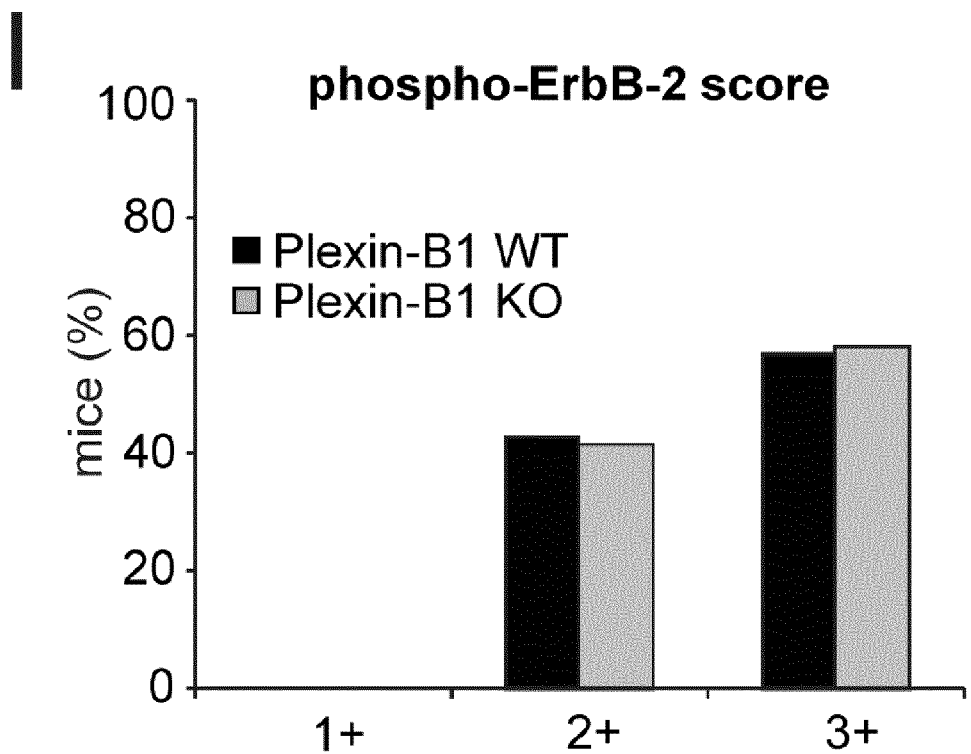
Figure 8:
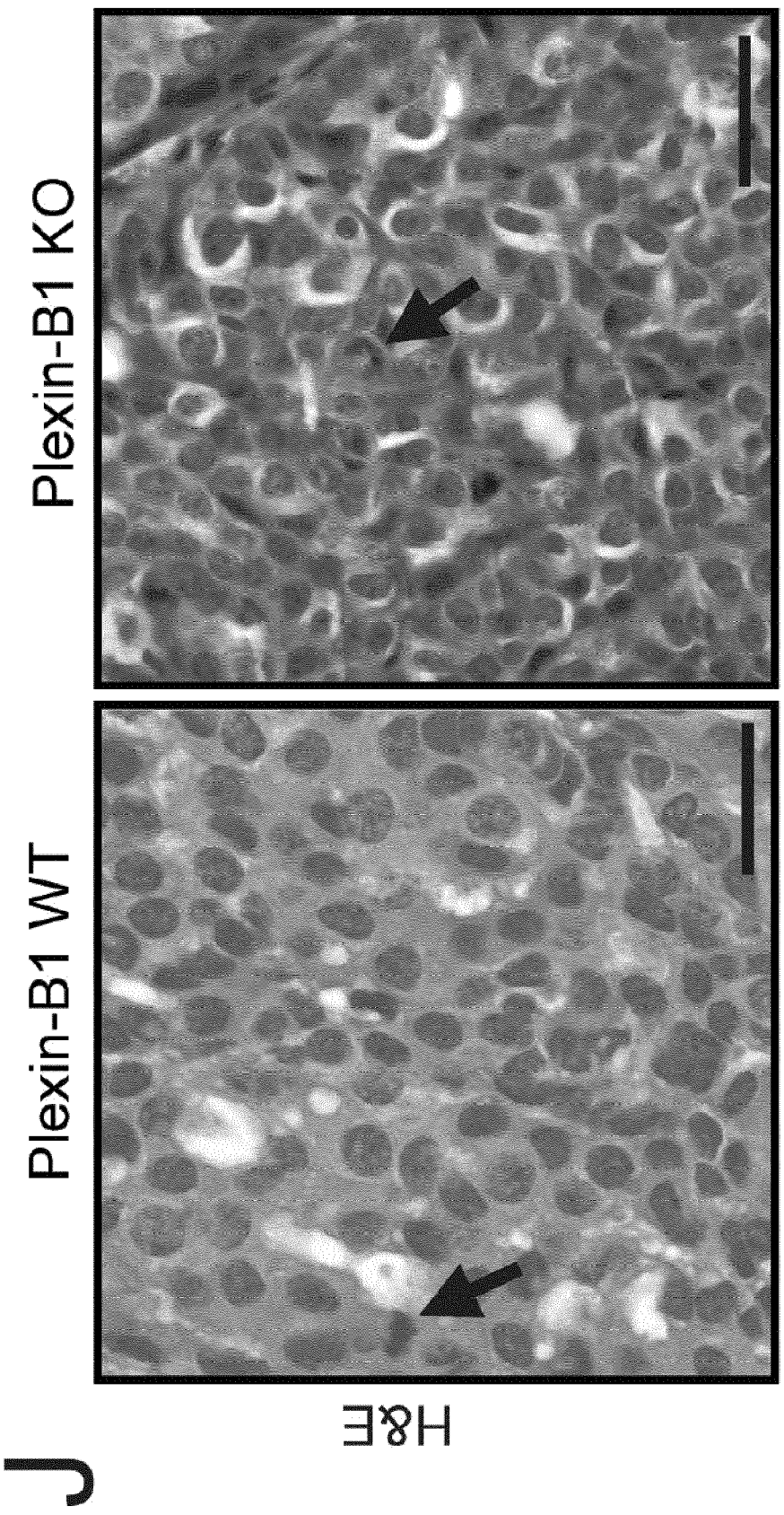
Figure 8:
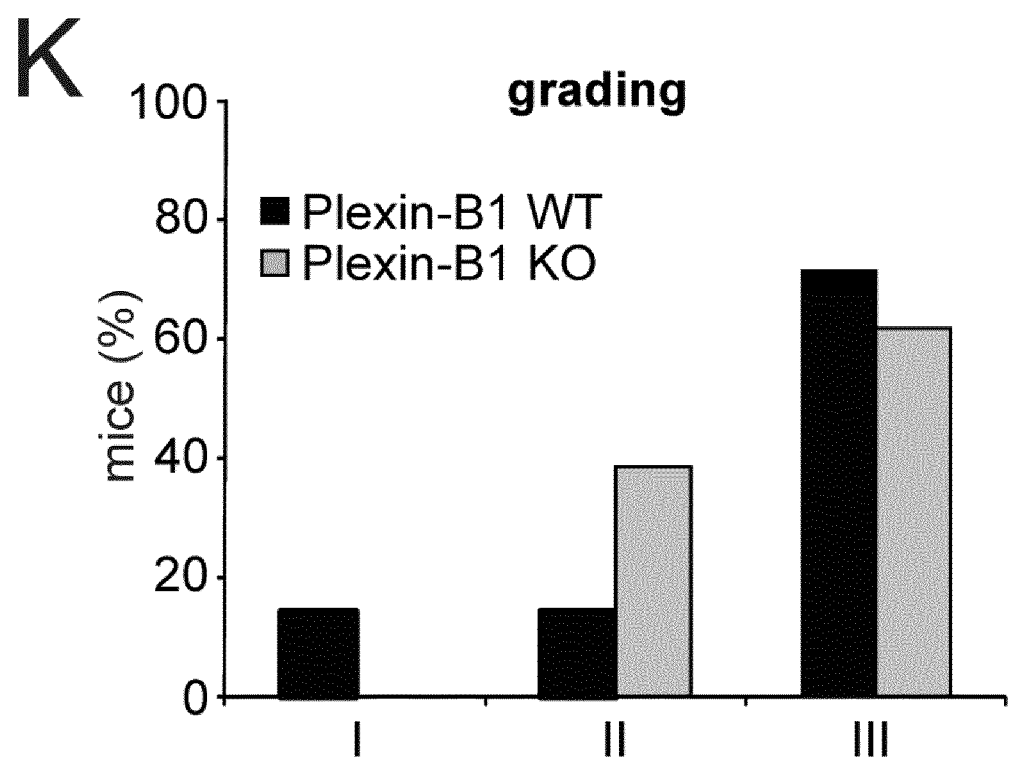
Figure 8:
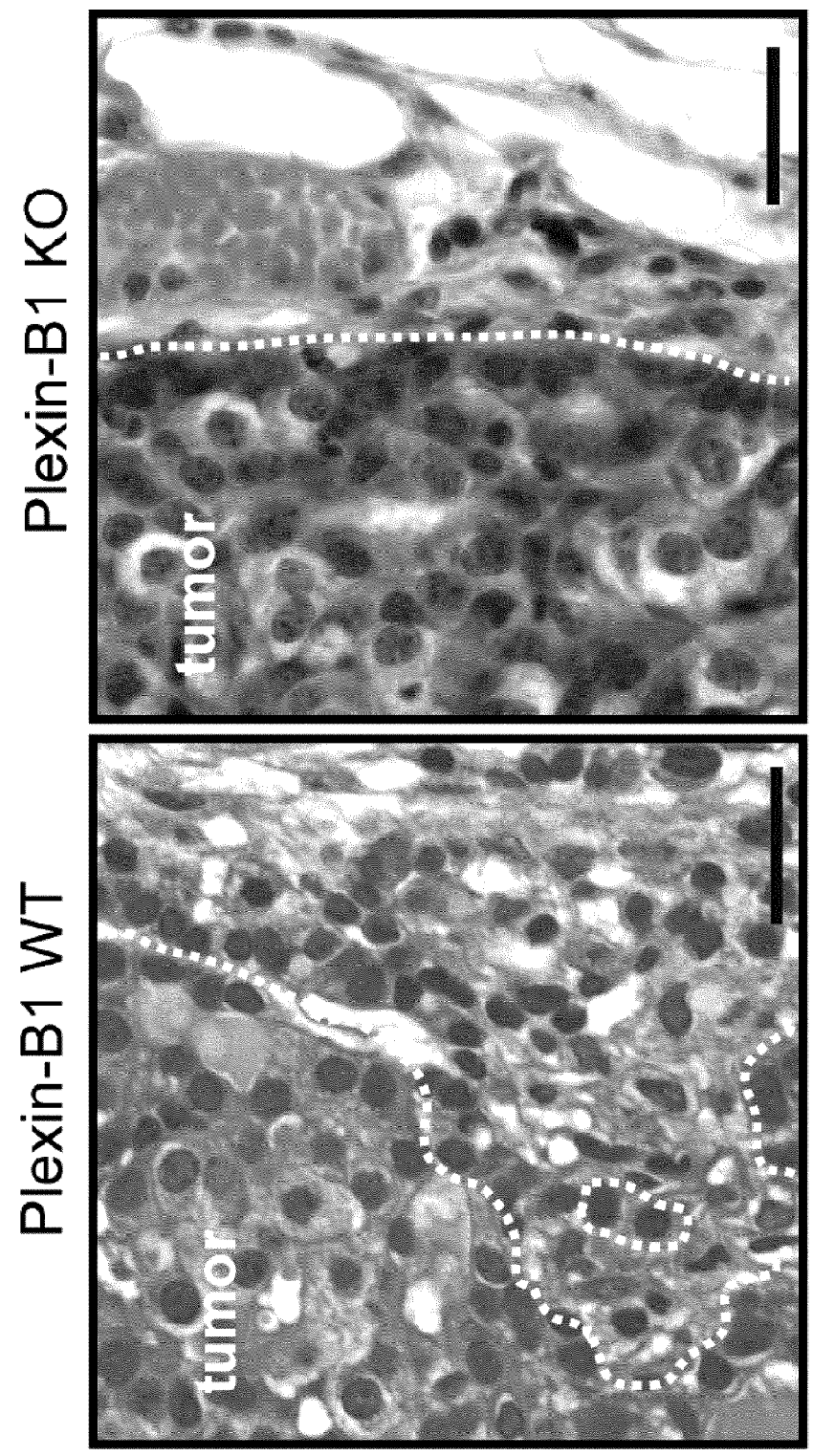
Figure 8:
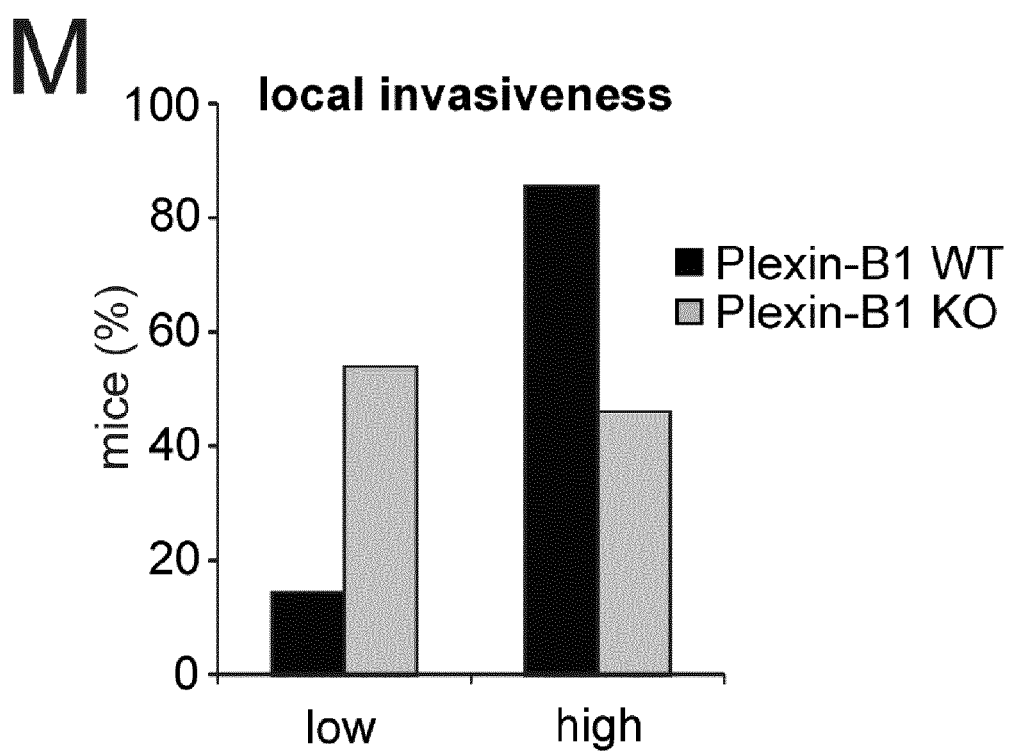

FIG. 8: Analysis of MMTVneu primary tumors. (A) RNA from primary tumor and lung metastasis was isolated and reverse transcribed (RT, reverse transcriptase). PCR analysis was carried out using primers specific for Plexin-B1. Primers for beta-actin were used as control. (B,C) Apoptosis, (D,E) vascularization, (F,G) macrophage infiltration, (H,I) phospho-ErbB-2 score, (J,K) grading and (L,M) local invasiveness (Plexin-B1 WT, n=7; Plexin-B1 KO, n=13) of MMTV-neu primary tumors. Representative pictures are shown in (B,D,F,H,J,L), quantifications of the results are provided in (C,E,G,I,K,M). Arrows point to (B) apoptotic cells positive for cleaved-caspase-3 (blue), (D) CD-31-positive blood vessels (red), (F) Mac-3-positive macrophages (red), (J) mitotic figures. The invasion front is marked by white dashed lines in (L). Scale bars represent 200 µm in (D), 40 µm in (H), 20 µm in (B,F,J,L).

Figure 9:
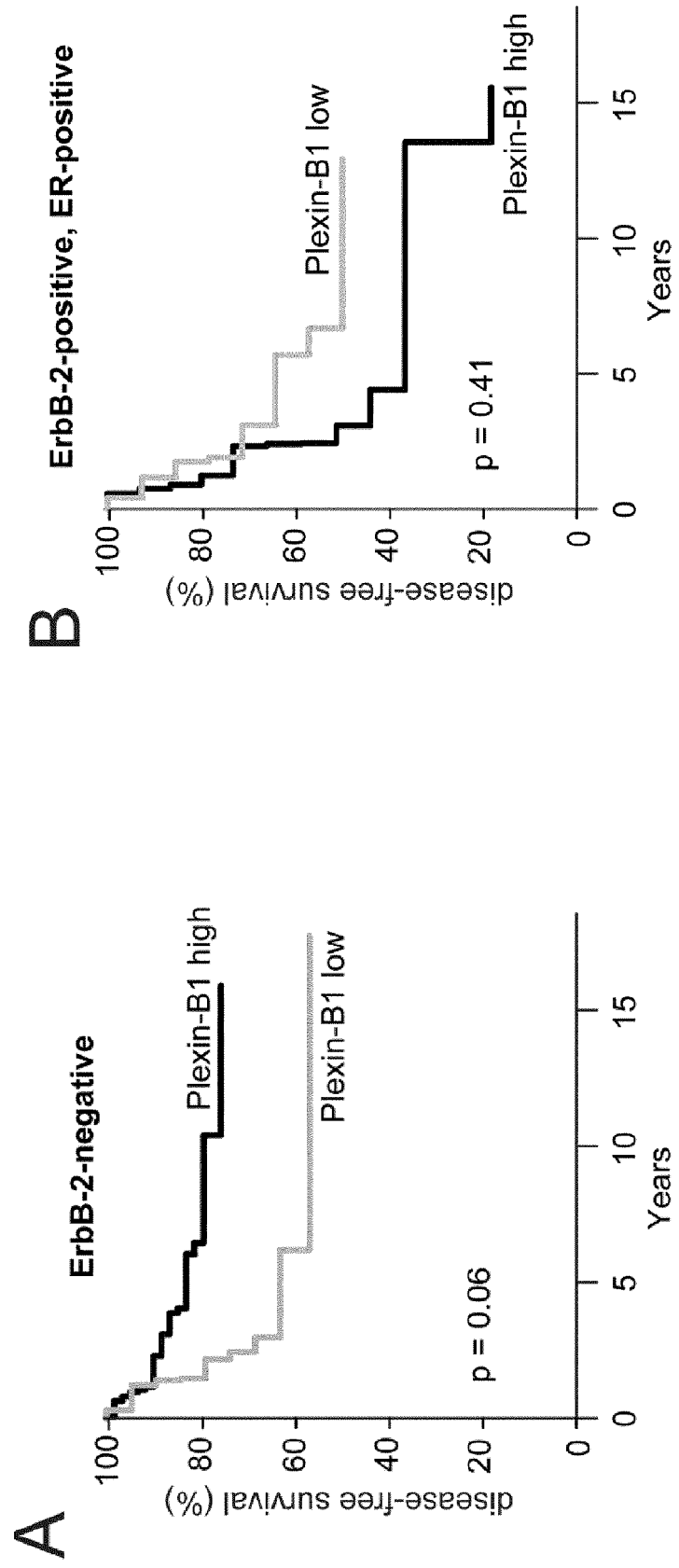
Figure 9:
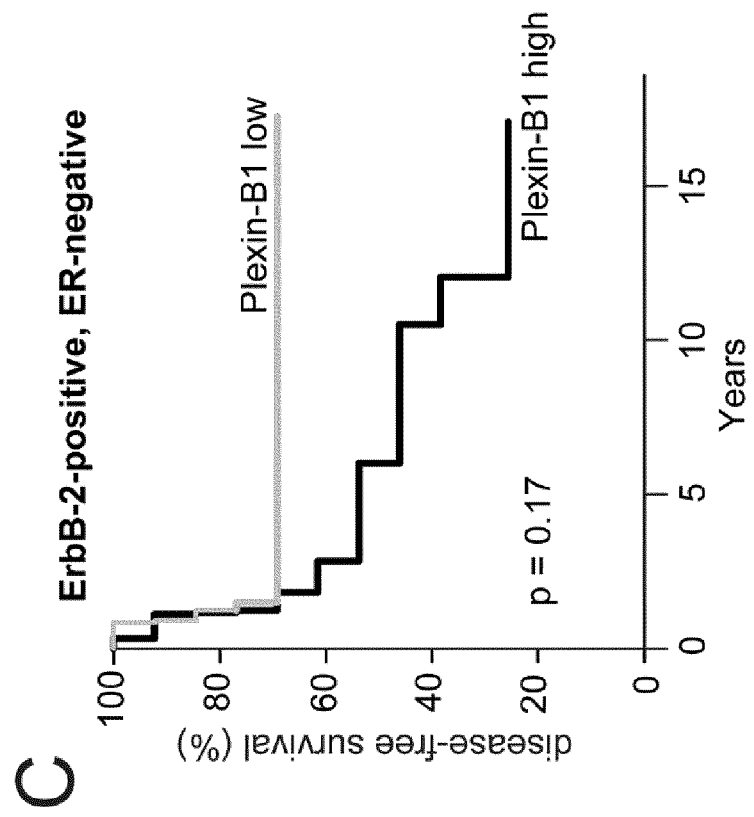

FIG. 9: Kaplan-Meier graphs representing the disease-free survival of patients with (A) ErbB-2-negative breast cancer (Plexin-B1 high: n=62, Plexin-B1 low: n=19), (B) ErbB-2-positive, ER-positive breast cancer (Plexin-B1 high: n=15, Plexin-B1 low: n=15), (C) ErbB-2-positive, ER-negative breast cancer (Plexin-B1 high: n=14, Plexin-B1 low: n=14). Black, high Plexin-B1 expression (Plexin-B1 high); grey, low Plexin-B1 expression (Plexin-B1 low). Statistical significances were tested by log-rank-test.

FIG. 10: Characteristics of breast cancer patients of whom (A) frozen breast cancer tissue was obtained for RT-PCR, (B) paraffin-embedded breast cancer tissue was obtained for immunohistochemistry, (C) frozen breast cancer tissue was obtained for immunoprecipitation and Western Blot.

FIG. 11: Characteristics of mouse monoclonal anti-Plexin-B1 antibodies (mAb) #19, #93, #527, #538, #635 and #830. Column #1: Ability of the respective mAb to recognize plexin-B1 protein in Western blot/immunoblot at the concentration 10 µg/ml), (+) means that there is some reactivity at the expected molecular weight, (++) means strong signal. Westerns with mAb #19 and #93 were repeated, and the specificity was confirmed using cells depleted of plexin-B1 by the means of RNAi. Column #2: Ability of the respective mAb to precipitate VSV-tagged, plexin-B1 overexpressed (OE) in HEK cells. Column #3: Ability of the respective mAb to precipitate native plexin-B1 from MCF-7 cells. Column #4: Ability of the respective mAb to co-immunoprecipitate plexin-B1/ErbB2 complex. Immunoprecipitations were performed in MCF-7, BT-474 and SK-OV-3 cell lines, all lines express plexin-B1 and different levels of ErbB2. (−) means that the addition of antibody blocks plexin-B1/ErbB2 interaction, (NA)—not applicable—since the antibody is not able to immunoprecipitate the native plexin-B1. Column #5: SK-OV-3 cells show basal higher RhoA activity, that is dependent on the overexpression of ErbB2 resulting in plexin-B1 phosphorylation and subsequent RhoA activation, (blocks) means ability of the respective mAb to decrease basal RhoA activity, based on the experiments described in column #4, the effect is because of the inhibition of plexin-B1/ErbB2 interaction. Column #6: MCF-7 cells express normal levels of plexin-B1 and ErbB2; the inventors have previously shown that stimulation with plexin-B1 ligand—Sema4D results in activation of ErbB-2, subsequent phosphorylation of plexin-B1 and RhoA activation. (blocks) means that the observed effect is due to an inhibition of plexin-B1/ErbB2 interaction (mAb #93 and #538) or because of competitive inhibition of binding of ligand Sema4D to receptor plexin-B1 (Antibodies #19 and #527). Column #7: R-Ras deactivation via plexin-B1 is independent of interaction with ErbB2, but dependent on stimulation with the ligand Sema4D, (blocks) means preincubation with antibody results in inability of plexin-B1 to deactivate R-Ras after stimulation with Sema4D, most probably due to competition between antibody and Sema4D. Column #8: Ability of the respective mAb to bind to the surface of cells expressing plexin-B1 and its homologue plexin-B2 (SKOV), and to cells depleted of plexin-B1 (SKOV sh), (no) shows lack of binding to the surface of cells depleted of plexin-B1, therefore indicating specificity of antibody to plexin-B1. Column #9: Ability of the respective mAb to block Sema4D binding to plexin-B1, experiments were performed in MCF-7 cells expressing native plexin-B and preincubated with anti-plexin-B1 monoclonal antibody. Column #10: Testing for crossreactivity of the respective mAb for other plexin-family members (plexin-A1-4, B1-3, C1 and D1). (No)—no crossreactivity observed. Column #11: Ability of the respective mAb to block RhoA-mediated basal cell invasivity—same mechanism as in column #5 (measured in the Matrigel invasion assay). (Yes)-antibody blocks invasion of SK-OV-3 and BT-474 cells. In summary: The inventors were able to show that mouse monoclonal anti-plexin-B1 antibodies #93 and #538 block plexin-B1/ErbB-2 interaction, whereas antibodies #19 and #527 block competitively ligand (sema4D)-receptor (plexin-B1) binding. Antibody #630 shows a weak reactivity in a Western blot. Antibody #830 is unspecific. Both #635 and #830 show no inhibitory effects on known, plexin-B1 mediated signaling pathways/cellular effects. Majority of tests were performed in a dose dependent manner. All tests were reproduced in at least two independent experiments.

All references cited in this specification are herewith incorporated by reference with respect to their entire disclosure content and the disclosure content specifically mentioned in this specification.

EXAMPLES

The following Examples shall merely illustrate the invention. They shall not be construed, whatsoever, to limit the scope of the invention.

Example 1

Methods 1.1 Antibodies. The following antibodies were used: rabbit polyclonal anti-cleaved-caspase-3 (Cell Signaling), rabbit polyclonal anti-CD31 (Abcam), mouse monoclonal anti-ErbB-2 (clone E2-4001, Invitrogen), rabbit polyclonal anti-phospho-ErbB-2[Y1248] (Cell Signaling), rabbit polyclonal anti-phospho-ErbB-2[Y1248] (Sigma-Aldrich), rat monoclonal anti-Mac-3 (clone M3/84, BD Pharmingen), goat polyclonal anti-Plexin-B1 (R&D systems), mouse monoclonal anti-Plexin-B1 (clone 439512, R&D Systems), rabbit monoclonal anti-RhoA (clone 67B9, Cell Signaling), rabbit polyclonal anti-RhoB (Cell Signaling), rabbit monoclonal anti-RhoC (clone D40E4, Cell Signaling), mouse monoclonal anti-alpha-tubulin (Sigma), goat polyclonal anti-VSV (Thermo), mouse monoclonal anti-phosphotyrosine (clone 4G10, Upstate Biotechnology), mouse monoclonal anti-FLAG (clone M2, Sigma), rabbit polyclonal anti-MYC (Sigma), mouse monoclonal anti-HA (clone HA-7, Sigma), trastuzumab (Genentech).

1.2 Plasmids. Eukaryotic expression plasmids carrying the human cDNAs of ErbB-2, FLAG-PDZ-RhoGEF, MYC-RhoA, HA-R-Ras and Rnd1 were described previously (18). Human VSV-plexin-B1 was kindly provided by L. Tamagnone (University of Torino, Torino, Italy). HA-RhoB and HA-RhoC were obtained from D. Brandt (University of Marburg, Marburg, Germany). Human ErbB-2 V664E was kindly provided by Axel Ullrich (Max-Planck-Institute for Biochemistry, Martinsried, Germany). Human VSV-Plexin-B1ΔC (P1xB1ΔC) lacking amino acids 1514-2135 of SEQ ID NO: 2 was generated by PCR and cloned into pcDNA3.

1.3 RNA extraction and RT-PCR. RNA extraction was performed using an RNeasy Kit (Qiagen) according to the manufacturer's instructions. RT-PCR was done using standard reagents and protocols (Fermentas). The following primers were used to analyze mRNA expression in human tissues: Plexin-B1 (p1xnb1): 5'-CAGCCACCACTTCGT-GAGTGCC-3' (sense) (SEQ ID NO: 6) and 5'-GGTGACT-GCCACAGCTGTTAGCTG-3' (antisense) (SEQ ID NO: 5); beta-actin: 5'-ATGGATGATGATATCGCCGCG-3' (sense) (SEQ ID NO: 7) and 5'-GAAGCATTTGCGGTGGACGAT-3' (antisense) (SEQ ID NO: 8). The following primers were used to analyze mRNA expression in mouse tissues: Plexin-B1 (p1xnb1): 5'-GGTGGAAAGGTACTATGCAGACAT-CAG-3' (sense) (SEQ ID NO: 9) and 5'-CCTCCTC-CAGGGCAGTGATGATC-3' (antisense) (SEQ ID NO: 10); beta-actin: 5'-GGTGTGATGGTGGGAATGGGTCAG-3' (sense) (SEQ ID NO: 11) and 5'-GAGGAAGAGGATGCG-GCAGTGG-3' (antisense) (SEQ ID NO: 12). All primers were intron-spanning.

1.4 Small interfering RNAs. The sequence of the siRNA used to knockdown plexin-B1 expression was ACCACGGU-CACCCGGAUUC (SEQ ID NO: 3) (IBA, Goettingen, Germany). The control siRNA and the siRNA directed against ErbB-2 were purchased from Qiagen.

1.5 Cell culture and Transfection. MCF-7 and BT-474 cells were obtained from the German Collection of Microorganisms and Cell Cultures (DSMZ, Braunschweig, Germany). T-47D and SK-BR-3 were obtained from the American Type Culture Collection (ATCC, Manassas, USA). SK-OV-3 cells were obtained from Cell Lines Service (CLS, Germany). All cell lines were cultured according to DSMZ, ATCC and CLS protocols, respectively. BT-474 cells were transfected with small interfering RNAs (siRNAs) using Lipofectamine RNAiMAX (Invitrogen) according to the manufacturer's instructions. Protein interaction studies and Rho pulldown assays were performed 48 hours after siRNA transfection. HEK 293 cells were transfected with cDNA plasmids using the calcium phosphate method.

1.6 Retroviral infections. In order to obtain siRNA-insensitive Plexin-B1, silent mutations were introduced at positions 3855 (C→T) and 3858 (G→A) of the coding region of the cDNAs encoding wild-type and mutated (Y1708F/Y1732F) Plexin-B1. The resulting sequences were subcloned into the retroviral vector pLNCX2 (Clontech). Selection and retroviral transfection were carried out as described before (18).

1.7 Lentiviral infections. To generate BT-474 cells with a stable knockdown of Plexin-B1, the inventors used the Mission shRNA system (Sigma-Aldrich) according to the manufacturer's instructions. Briefly, cells were infected with lentiviruses encoding shRNAs and a puromycin resistance. After selection, successful knockdown was verified by Western blotting.

1.8 Western blotting and Immunoprecipitation. Western blotting was performed according to standard laboratory protocols. Immunoprecipitations were carried out in ice-cold radioimmunoprecipitation buffer (150 mM NaCl, 50 mM Tris pH 7.4, 5 mM EDTA pH 8.0, 1% Triton X-100, 0.1% SDS, 0.5% sodium deoxycholate, protease inhibitors and 2 mM $Na_3VO_4$).

1.9 Production and Purification of recombinant peptides and proteins. Recombinant human soluble Sema4D (residues 1-657 of the amino acid sequence shown in Q92854) was purified from Chinese hamster ovary cells as described previously (18). An N-terminally His-tagged recombinant peptide, comprising the amino acids 35 to 150 of human Plexin-B1 (SEQ ID NO. 2) was expressed in *E.coli* and purified by metal-ion affinity chromatography using nickel agarose (GenScript, USA). This peptide corresponds to the peptide employed by R&D Systems, USA, for the immunization of goats to raise an anti-Plexin-B1 antibody used in this study. To produce the extracellular domain of human Plexin-B1, it has been first tried to use the complete extracellular domain (ECD) from amino acid residue 20 to 1491 of human Plexin-B1 shown in SEQ ID NO. 2. However, this recombinant protein was not producible in soluble form. Therefore, recombinant producibility and solubility of the following truncated recombinant forms of the ECD of human Plexin-B1 have been tested, with the following results:

a) amino acid residue 20 to 1298 of SEQ ID NO. 2 (comprising the Semaphorin domain, three PSI domains, and three IPT repeats): not soluble;

b) amino acid residue 20 to 1160 of SEQ ID NO. 2 (comprising the Semaphorin domain, three PSI domains, and one IPT repeat): not soluble;

c) amino acid residue 20 to 1068 of SEQ ID NO. 2 (comprising the Semaphorin domain and three PSI domains): not soluble;

d) amino acid residue 20 to 678 of SEQ ID NO. 2 (comprising the Semaphorin domain and two PSI domains): good producibility, bad solubility;

e) amino acid residue 20 to 543 of SEQ ID NO. 2 (comprising the Semaphorin domain and one PSI domain): good producibility, good solubility;

f) amino acid residue 20 to 473 of SEQ ID NO. 2 (comprising only the Semaphorin domain): good producibility, bad solubility.

Therefore, the cDNA sequence encoding the amino acids 20-534 of human Plexin-B-1 (SEQ ID NO. 2) has been cloned into the pSecTag2Hygro(A) vector. The domain was purified from the supernatant of transfected HEK293 cells by metal-ion affinity chromatography using cobalt agarose (Thermo) followed by gel fitration chromatography using a Superdex 200 10/300 GL column (Amersham).

1.10 Production of anti-Plexin-B1 antibodies. Monoclonal antibodies against the purified extracellular domain of human Plexin-B1 (amino acids 20-534 of SEQ ID NO. 2; see Example 1.9) were raised in mice according to the method described by Köhler and Milstein (47). In total, 1236 hybridoma supernatants have been tested by ELISA. 163 hybridoma supernatants showed positive signals, i.e. binding to the recombinant protein used for immunization. These supernatants have further been tested as regards their ability to recognize recombinant human Plexin-B1 protein in Western blot, capability of inhibition of binding of Sema4D ligand to native human Plexin-B1 (receptor), capability of inhibition of Sema4D-induced activation of RhoA which is a down-stream effector of Plexin-B1, and binding to Plexin-B1 expressing cells. Four of these hybridoma supernatants, i.e. #93, #538, #19 and #527 were positive in one or more of said tests, as shown in more detail in FIG. 11. Antibodies were purified from the supernatant of hybridomas by protein A/G sepharose affinity columns.

Mouse monoclonal anti-plexin-B1 antibody #93 (or clone #93) comprises an H (heavy) chain V (variable) region comprising an amino acid sequence shown in SEQ ID NO. 15 and a L (light) chain V (variable) region comprising an amino acid sequence shown in SEQ ID NO. 16. Mouse monoclonal anti-plexin-B1 antibody #538 comprises an H (heavy) chain V (variable) region comprising an amino acid sequence shown in SEQ ID NO. 19 and a L (light) chain V (variable) region comprising an amino acid sequence shown in SEQ ID NO. 20. Both of these mouse monoclonal antibodies bind to amino acids 20-534 of the extracellular domain of human plexin-B1 (SEQ ID NO. 2), or a partial peptide or fragment thereof, and inhibit binding of human plexin-B1 to Erb-B2. Unexpectedly, it has been found that the mouse monoclonal anti-Plexin-B1 antibody #93 interferes with the interaction between ErbB-2 and Plexin-B1, but does not inhibit binding of the ligand Sema4D to the receptor Plexin-B1.

Mouse monoclonal anti-plexin-B1 antibody #19 comprises an H (heavy) chain V (variable) region comprising an amino acid sequence shown in SEQ ID NO. 13 and a L (light) chain V (variable) region comprising an amino acid sequence shown in SEQ ID NO. 14. Mouse monoclonal anti-plexin-B1 antibody #527 comprises an H (heavy) chain V (variable) region comprising an amino acid sequence shown in SEQ ID NO. 17 and a L (light) chain V (variable) region comprising an amino acid sequence shown in SEQ ID NO. 18. These mouse monoclonal antibodies bind to amino acids 20-534 of the extracellular domain of human plexin-B1 (SEQ ID NO. 2), or a partial peptide or fragment thereof, and inhibit binding of the ligand Sema4D to human plexin-B1.

1.11 Determination of activated Rho and Ras. The amounts of activated cellular RhoA, RhoB, RhoC and R-Ras were determined by precipitation with a fusion protein consisting of GST and the Rho-binding domain of Rhotekin (GST-RBD) or the Ras-binding domain of Raf1 (GST-Raf1) as described previously (18). All Rho pulldown experiments were carried out after overnight starvation in medium containing 0.5% FBS. Cells were incubated with Sema4D for 20 min, with the recombinant extracellular part of Plexin-B1 or Trastuzumab for 45 min, or with a mouse monoclonal anti-Plexin-B1 antibody (anti-P1xB1; clone #93, 1.8 ng/µl) for 60 min prior to cell lysis.

1.12 Proliferation, migration and invasion assays. For proliferation assays, cells were seeded in 24-well-plates and transfected with siRNA. Cells were then counted using a Neubauer chamber on 5 consecutive days (3 wells per data point). In parallel, siRNA knockdown efficiency was monitored by Western Blotting. For migration assays, $5\times10^4$ BT-474 cells stably expressing control shRNA or shRNA directed against Plexin-B1, were serum-starved overnight, seeded on ThinCert filter insets with 8.0 µm pore size in 24-well-plates (Greiner bio-one) and allowed to migrate against 20% serum. 24 h later, non-migrated cells on the upper surface of the filter were removed with a cotton-swab, migrated cells were stained with toluidine blue and counted. For invasion assays, cells were serum-starved 24 h after siRNA transfection. 48h after siRNA transfection, $1\times10^5$ BT-474 cells were seeded into Growth Factor Reduced Matrigel Invasion Chambers with 8.0 µm pore size (BD Biosciences). BT-474 cells were allowed to invade against 20% serum for 48 h. After removal of non-invading cells on the upper surface of the filter with a cotton-swab, invading cells were stained with toluidine blue and counted. SiRNA knockdown efficiency was routinely assessed by Western Blotting. In invasion assays using SK-OV-3 cells, $2.5\times10^4$ serum-starved cells invaded against 10% serum for 16 h.

1.13 SRE reporter gene assays. Using the calcium phosphate method, HEK293 cells were transfected with 3DA.Luc, a reporter plasmid expressing firefly luciferase under the control of a mutant serum response element (SRE.L) which lacks a ternary complex factor binding site (48), together with plasmids encoding Plexin-B1 and PDZ-RhoGEF. 36 hours after transfection, cells were serum-starved for 12 hours, and the activity of firefly luciferase was measured using the One-Glo Kit (Promega) according to the manufacturer's instructions. The obtained values were normalized to cell number as determined by CellTiter Fluo kit (Promega).

1.14 Sema4D binding assay. MCF-7 cells were treated without or with the mouse monoclonal anti-Plexin-B1 antibody (clone #93). After one hour cells were washed with PBS and incubated with myc-Sema4D for 30 min. Unbound Sema4D was removed by washing with PBS, and bound Sema4D was detected using an HRP-conjugated anti-myc antibody. HRP activity was measured using OPD chromogenic substrate (Dako) according to the manufacturer's protocol.

1.15 Genetically-altered mice. MMTVneu mice (5) were purchased from The Jackson Laboratory (Stock number 002376). Plexin-B1 knockout mice (p1xnb1$^{-/-}$) were generated as described previously (31). Female animals from p1xnb1$^{+/-}$×MMTVneu;p1xnb1$^{+/-}$ crosses were kept as virgins for the entire period of the study. The inventors monitored mice for tumors by palpation weekly. Mice were sacrificed 8.5 weeks after the first appearance of a palpable tumor. Tumors were excised and weighed. Pictures of the lungs were taken after fixation in 4% PFA overnight (4° C.) and dehydration in ethanol. Lungs were then further processed for histology and sectioned on a microtome (section thickness 5 µm). Sections were stained with H&E and analyzed for the presence of metastases. The distance between the analyzed sections was 50 µm.

1.16 Histology and immunohistochemistry. The grading of MMTVneu primary tumors was scored on H&E-stained sections. For every tumor analyzed, a sub-score of 1, 2 or 3 was assigned to each of the following parameters: tubule formation (1=>75%, 2=10-75%, 3=≤10%), nuclear pleomorphism (1=uniform, 2=moderate variation in shape and size, 332 marked variation) and mitotic count (1=0-9/10 hpf, 2=10-19/10 hpf, 3=≥20/10 hpf). The sub-scores were added up to yield a total score. A total score of 3-5 corresponds to grade 1, a total score of 6-7 corresponds to grade 2 and a total score of 8-9 corresponds to grade 3. The local invasiveness of the primary mouse tumors was assessed on H&E-stained sections on the basis of their infiltration into the surrounding connective tissue. Each tumor was judged to be of "low" or "high" invasiveness, with "low" invasiveness being defined as a tumor that does not show any single cell infiltrations into the surrounding tissue and "high" invasiveness being defined as a tumor with single cell infiltrations into the surrounding tissue. Immunohistochemistry was carried out on paraffin-embedded sections using standard reagents and protocols (Vector Laboratories). The phospho-ErbB-2 score was analyzed analogously to the well-established ErbB-2 score: The score 0 stands for absence of significant circumferential membranous staining, whereas scores 1+, 2+ and 3+ correspond to a positive circumferential membranous staining for phospho-ErbB-2[Y1248] (1+: weak staining of ≥1% or moderate staining of <10% of tumor cells; 2+: moderate staining of >10% or strong staining of <30% of tumor cells; 3+ strong staining of >30% of tumor cells). To test for the specificity of the goat polyclonal anti-Plexin-B1 antibody (R&D Systems), the antibody was preincubated with the peptide used for immunization at a mass ratio of 1:5 for 1 h at room temperature prior to application to the tissue slides.

1.17 Analysis of vascularization, macrophage infiltration and apoptosis. For the analysis of vascularization, tumor sections were stained for CD31 and imaged (3 randomly chosen fields per tumor, 100× magnification). Quantification was performed by computer-assisted digital image analysis as described (49). Macrophages were stained on tumor sections by an anti-Mac-3-antibody and macrophage numbers were counted by computer-assisted digital image analysis in 3 randomly chosen fields per tumor (200× magnification). For the analysis of apoptosis, sections were stained for cleaved-caspase-3 and positive cells were counted in 10 randomly selected fields per tumor (400× magnification).

1.18 Patients. Frozen and paraffin-embedded breast cancer tissues were provided by the tissue bank of the National Centre for Tumor Diseases (NCT Heidelberg, Germany) (FIG. 10). The ErbB-2 score was determined by immunohistochemistry using an anti-ErbB-2 antibody (Dako, clone A0485). The ErbB-2 score 0 stands for the absence of staining, whereas ErbB-2 scores 1+, 2+ and 3+ correspond to a positive staining for ErbB-2 (1+: weak staining of 10% of tumor cells; 2+: moderate staining of 10-30% of tumor cells; 3+ strong staining of >30% of tumor cells).

1.19 Microarray analysis. The following datasets of human breast cancer patients were downloaded from the Gene Expression Omnibus (GEO) repository http://www.ncbi.nlm.nih.gov/geo/: GSE1456, GSE2034, GSE3494, GSE4922, GSE5327, GSE7390, GSE11121, GSE12093. All datasets were filtered for platform HG-U133a CEL files. The whole batch consisted of 1548 arrays and was preprocessed by the Affymetrix power tools (normalization method RMA). The HG-U133A annotation file was downloaded from http://www.affymetrix.com. The ERBB2 probeset ID 216836_s_at was used to group the arrays into ErbB-2-overexpressing and ErbB-2-non-overexpressing tumors. The inventors identified 200 arrays as ErbB-2-overexpressing and 1348 as ErbB-2-non-overexpressing tumors. Previous studies have shown that ErbB-2 mRNA expression levels correlate with protein expression levels as determined by immunohistochemistry (50). Within the group of arrays with ErbB-2 overexpression two subgroups were defined on the basis of Plexin-B1 expression levels (215807_s_at probeset): One subgroup comprised the 60 arrays with the lowest Plexin-B1 expression, the other subgroup comprised the 60 arrays with the highest Plexin-B1 expression. The 60 arrays with low Plexin-B1 expression were mapped to the available 22 clinical datasets and the 60 arrays with high Plexin-B1 expression were mapped to the available 39 clinical datasets. Analogously, within the group of arrays without ErbB-2 overexpression two subgroups were defined on the basis of Plexin-B1 expression levels: One subgroup comprised the 100 arrays with the lowest Plexin-B1 expression, the other subgroup comprised the 100 arrays with the highest Plexin-B1 expression. The 100 arrays with low Plexin-B1 expression were mapped to the available 19 clinical datasets and the 100 arrays with high Plexin-B1 expression were mapped to the available 62 clinical datasets. As the different arrays provided different clinical end points, the inventors combined RFS (relapse-free survival), DMFS (distant metastasis-free survival) and DFS (disease-free survival) to yield one united clinical endpoint designated disease-free survival. Using survival in years and survival event data the inventors performed a survival analysis. Since the inventors had sufficient events in both groups, they assumed to have a chi$^2$ distribution with one degree of freedom. By plotting Kaplan-Meier curves using Rfunctions (Surv and survfit), the inventors were able to demonstrate varying survival lines. As the lines did not cross each other, the inventors assumed the event rates to be proportional to the Cox model. Therefore, the inventors chose the log-rank test (higher power than Wilcoxon by these findings) to compare the survival curves. Log-rank test was performed by the R survdiff function. For the analysis of overall survival, the inventors took identical array groups as mentioned above (ErbB-2 overexpression, 60 arrays with lowest Plexin-B1 expression, 60 arrays with highest Plexin-B1 expression) and mapped these groups to available disease-specific survival (DSS) data from the GEO datasets. The inventors were able to map seven arrays of the group with low Plexin-B1 expression and 13 arrays of the group with high Plexin-B1 expression to DSS values. Kaplan-Meier curves were plotted by R functions as described above. Within the group of 200 arrays with ErbB-2 overexpression, data on estrogen receptor (ER) status was available for 77 arrays. Of those, 29 arrays were ER-negative (28 with clinical outcome data) and 48 arrays were ER-positive (31 with clinical outcome data). Arrays with clinical outcome data available were sorted for Plexin-B1 expression and Kaplan-Meier curves were plotted by R functions as described above.

1.20 Statistical analysis. The statistical significance was evaluated by two-tailed t-test (FIG. 2E, FIG. 2F, FIG. 2H, FIG. 2K, FIG. 2L, FIG. 3B, FIG. 3F, FIG. 3G, FIG. 6B-D, FIG. 7C), Fisher's exact test (FIG. 3D) and log-rank test (FIG. 3A, FIG. 4D, FIG. 4E, FIG. 9A-C). A P value less than 0.05 was considered significant. * indicates a level of significance<0.05,  indicate a level of significance<0.01, * indicate a level of significance<0.001.

1.21 Study approval. All procedures of animal care and use in this study were approved by the local animal ethics committee (Regierungspräsidium Karlsruhe, Germany). Frozen and paraffin-embedded breast cancer tissues were provided by the tissue bank of the National Centre for Tumor Diseases (NCT Heidelberg, Germany) in accordance with the regulations of the tissue bank and the approval of the ethics committee of the University of Heidelberg. Patients provided informed consent to the use of tissue.

Example 2

Results 2.1 Overexpression of ErbB-2 results in activation of Plexin-B1 and Rho GTPases. To test whether overexpression of ErbB-2 is sufficient to phosphorylate and activate Plexin-B1 the inventors overexpressed wild-type or constitutively active ErbB-2 in HEK293 cells. This resulted in tyrosine phosphorylation of Plexin-B1 (FIG. 1A) as well as in activation of RhoA (FIG. 1B) and RhoC (FIG. 1D), but not of RhoB (FIG. 1C) independently of a Plexin-B1 ligand. Expression of a Plexin-B1 mutant which lacks the intracellular domain blocked RhoA and RhoC activation, indicating that Plexin-B1 signaling is indeed required for RhoA and RhoC activation downstream of ErbB-2 (FIG. 1B, FIG. 5). In addition to its ability to mediate Rho signaling, Plexin-B1 has been shown to be a GTPase-activating protein (GAP) for R-Ras (29). Consistent with earlier studies which showed that R-RasGAP activity is independent of Plexin-B1 phosphorylation by ErbB-2 (18), overexpression of wildtype or constitutively-active ErbB-2 did not affect the R-RasGAP activity of Plexin-B1 (FIG. 1E). These data show that overexpression of ErbB-2 results in activation of Plexin-B1 and Rho signaling.

2.2 In human breast cancer cells, ErbB-2 promotes invasiveness through Plexin-B1 and RhoA/RhoC. To investigate the role of ErbB-2/Plexin-B1 signaling in cancer cells, the inventors compared several human breast cancer cell lines with respect to Plexin-B1 and RhoA activity. Basal Plexin-B1 phosphorylation and RhoA activity were detectable only in cancer cell lines overexpressing ErbB-2 consistent with the notion that this pathway is active in breast cancer cells with high levels but not with low levels of ErbB-2 expression (FIG. 2A). In line with this, knockdown of ErbB-2 in BT-474 cells, which endogenously express high levels of ErbB-2, resulted in a marked reduction of Plexin-B1 tyrosine phosphorylation and RhoA/RhoC activity (FIG. 2B). While loss of Plexin-B1 expression in ErbB-2-overexpressing BT-474 cells did not affect ErbB-2 tyrosine phosphorylation, it resulted in a strong inhibition of RhoA and RhoC activity (FIGS. 2C and 2D). Active RhoB which is known for its tumor suppressor function (30) could not be detected in BT-474 cells (data not shown). Thus, Plexin-B1 links ErbB-2 overexpression to the activation of RhoA and RhoC. In light of the pro-invasive cellular effects of RhoA and RhoC, the inventors tested whether ErbB-2 promotes tumor cell invasion by activation of RhoA and RhoC through the phosphorylation and activation of Plexin-B1. Knockdown of Plexin-B1 had no effect on the proliferation of ErbB-2-overexpressing BT-474 cells (FIG. 2E), but strongly reduced their migratory and invasive capacity (FIG. 2F, FIGS. 6B and 6C). To test whether Plexin-B1 phosphorylation by ErbB-2 was required for cancer cell invasiveness, the inventors expressed siRNA-resistant versions of wildtype Plexin-B1 and of a Plexin-B1(Y1708F/1732F) mutant which is not phosphorylated by ErbB-2 (18). After siRNA-mediated knockdown of endogenous Plexin-B1, cells expressing phosphorylation site-deficient Plexin-B1 had strongly reduced levels of active RhoA/RhoC and invaded dramatically less than cells expressing wildtype Plexin-B1 (FIGS. 2G and 2H). Consistent with their well-established role in cancer cell invasion, knockdown of RhoA or RhoC impaired the invasive capacity of BT-474 cells (FIG. 6D).

To further analyze the significance of the ErbB-2/Plexin-B1 receptor complex in breast cancer cells, the inventors raised mouse monoclonal anti-Plexin-B1 antibodies, and purified the extracellular domain of Plexin-B1 (P1xB1 ext). Both P1xB1 ext as well as a particular anti-Plexin-B1 antibody (clone #93) efficiently inhibited the interaction between ErbB-2 and Plexin-B1 (FIG. 6E-H). Uncoupling of ErbB-2 and Plexin-B1 by the anti-Plexin-B1 antibody or by P1xB1ext in BT-474 cells strongly reduced tyrosine phosphorylation of Plexin-B1 (FIGS. 6E and 6H), inhibited RhoA and RhoC activity (FIGS. 2I and 2J, FIG. 6F) and decreased invasion of tumor cells (FIGS. 2K and 2L). The therapeutic anti-ErbB-2 antibody trastuzumab which did not affect the interaction between ErbB-2 and Plexin-B1 (data not shown) inhibited tumor cell invasion to a comparable degree as P1xB1 ext (FIG. 2L), and the inhibitory effects of P1xB1ext and trastuzumab on tumor cell invasion were additive (FIG. 2L). In an ErbB-2-overexpressing ovarian cancer cell line, SK-OV-3, uncoupling of ErbB-2 and Plexin-B1 by the anti-Plexin-B1 antibody #93 inhibited tyrosine phosphorylation of Plexin-B1, RhoA and RhoC activity, and invasion of tumor cells (FIG. 7). Together, these data show that Plexin-B1 is required for the invasive capacity of ErbB-2-overexpressing breast and ovarian cancer cells in vitro.

2.3 In mice with ErbB-2-overexpressing breast cancer, ablation of the Plexin-B1 gene reduces metastasis. To test whether Plexin-B1 mediates ErbB-2-dependent metastasis also in vivo, the inventors employed transgenic MMTVneu mice which overexpress wild-type ErbB-2 in their mammary glands and develop metastasizing breast cancer (5). Both primary tumors as well as lung metastases of MMTVneu mice expressed Plexin-B1 (FIG. 8A). MMTVneu mice were crossed with Plexin-B1-deficient mice, which are viable and fertile, show normal lactation and are devoid of any obvious defects (31-32). The inventors found that Plexin-B1 had no effect on tumor-free survival or the size of the primary tumor (FIGS. 3A and 3B, FIGS. 8B and 8C). Examination of the histology of the primary tumors did not reveal any impact of Plexin-B1 ablation on vascularization or immune cell infiltration (FIG. 8D-G). Consistent with the notion that Plexin-B1 signals downstream of ErbB-2, loss of Plexin-B1 expression did not affect ErbB-2 tyrosine phosphorylation of cancer cells (FIGS. 8H and 8I). While grading of the primary tumors was comparable between the groups (FIGS. 8J and 8K), Plexin-B1-deficient tumors showed a trend towards a reduced local invasiveness (FIGS. 8L and 8M). Examination of the lungs revealed a striking reduction in macroscopically visible metastases (FIGS. 3C and 3D). A histological analysis confirmed a strong decrease in the number of metastases in the lung (FIG. 3E-3G). These results indicate that Plexin-B1 has no effect on tumorigenesis or tumor growth but is required for metastasis of ErbB-2-dependent breast cancers in vivo.

2.4 Plexin-B1 is activated in human ErbB-2-overexpressing breast cancer, and its expression correlates with prognosis. To determine whether ErbB-2/Plexin-B1 signalling also plays a role in human breast cancer, the inventors studied the expression of Plexin-B1 in human breast cancer tissue (FIGS. 10A and 10B). Plexin-B1 mRNA and protein were detectable in all breast cancer tissues analyzed independently of their ErbB-2 score (FIGS. 4A and 4B). In samples from patients with ErbB-2-overexpressing breast cancer (FIG. 10C) the inventors found Plexin-B1 to be tyrosine phosphorylated whereas no tyrosine phosphorylation of Plexin-B1 could be detected in ErbB-2-negative breast cancers (FIG. 4C). This indicated that ErbB-2 phosphorylates and activates Plexin-B1 also in human breast cancer tissue.

In microarray datasets of human breast cancer tissues, no correlation between Plexin-B1 and ErbB-2 expression levels was found (data not shown). Among patients with ErbB-2-negative breast cancer, low expression levels of Plexin-B1 showed a trend towards shorter disease-free survival compared to high Plexin-B1 expression levels (FIG. 9A), thereby confirming previous studies (33). In striking contrast, among patients with ErbB-2-overexpressing breast cancer, low expression levels of Plexin-B1 significantly correlated with longer disease-free survival compared to high Plexin-B1 expression levels (FIG. 4D). Data on overall survival were available only for a small number of patients; however, there was a statistically non-significant trend towards higher overall survival in patients with low Plexin-B1 expression (FIG. 4E). In subsets of ErbB-2-positive breast cancers stratified according to estrogen receptor status, Plexin-B1 expression levels did not significantly correlate with prognosis (FIG. 9B-C).

Example 3

Summary

ErbB-2, a metastasis-promoting receptor tyrosine kinase, is overexpressed in about 30% of all breast cancers. The signaling events downstream of ErbB-2 which drive cancer cell invasion and metastasis remain incompletely understood. Here the inventors show that overexpression of ErbB-2 leads to activation of the semaphorin receptor Plexin-B1. Plexin-B1 was required for ErbB-2-dependent activation of the prometastatic small GTPases RhoA and RhoC and promoted invasive behavior of human breast cancer cells. In a mouse model of ErbB-2-overexpressing breast cancer, ablation of the gene encoding Plexin-B1 strongly reduced the occurrence of metastases, and in human patients with ErbB-2-overexpressing breast cancer low levels of Plexin-B1 expression significantly correlated with good prognosis. Plexin-B1 therefore represents a new therapeutic target in ErbB-2-positive cancers, particularly in ErbB-2-positive breast cancers.

Example 4

Discussion

Given that metastasis rather than local growth is the major prognostic factor in breast cancer, the elucidation of molecular mechanisms underlying metastasis is of crucial importance. Rho GTPases are key regulators of cell migration, and Rho signaling promotes cancer cell invasion and metastasis (23-28). The fact that Plexin-B1 can interact with ErbB-2 and also with RhoGEF proteins to regulate RhoA prompted the inventors to test whether Plexin-B1 could act downstream of ErbB-2 and link ErbB-2 overexpression to the activation of Rho GTPases. In human breast cancer cells overexpressing ErbB-2, Plexin-B1 was tyrosine phosphorylated, and this tyrosine phosphorylation of Plexin-B1 as well as RhoA/RhoC activity was blocked by siRNA-mediated knockdown of ErbB-2. While knockdown of Plexin-B1 expression did not affect ErbB-2 tyrosine phosphorylation, it inhibited RhoA and RhoC activity as well as cancer cell invasiveness. Replacement of the endogenous Plexin-B1 protein by a mutant form of Plexin-B1 that lacks the tyrosine residues phosphorylated by ErbB-2 also strongly decreased RhoA/RhoC activity and the invasive capacity of cancer cells. Furthermore, interference with the interaction between ErbB-2 and Plexin-B1 by an anti-Plexin-B1 antibody or the recombinant extracellular domain of Plexin-B1 (P1xB1ext) reduced RhoA/RhoC activity and cancer cell invasion. Based on these in vitro findings the inventors conclude that overexpression of ErbB-2 results in phosphorylation and activation of Plexin-B1. This leads to activation of RhoGEF11/12 proteins (20-22) and RhoA/RhoC as well as to increased cancer cell invasiveness (FIG. 4F).

Similar to the cancer cell lines in vitro the inventors found that Plexin-B1 was also tyrosine phosphorylated in human breast cancer tissue overexpressing ErbB-2. In mice with ErbB-2-positive breast cancer, lack of Plexin-B1 strongly reduced metastasis and in humans with ErbB-2-positive breast cancer, low levels of Plexin-B1 expression correlated with good prognosis. Interestingly, both knockdown of Plexin-B1 in vitro as well as the knockout of Plexin-B1 in vivo did not affect the proliferation of ErbB-2-overexpressing cancer cells. The analysis of the histology of primary tumors in mice revealed no difference between Plexin-B1 knockout and control animals with respect to vascularization or immune cell infiltration. This is in line with previous findings in xenograft cancer models (34) and argues against a major role of Plexin-B1 in cells of the tumor microenvironment. Consistent with the in vitro findings, Plexin-B1 ablation did not affect ErbB-2 tyrosine phosphorylation, thereby indicating that ErbB-2 is upstream of Plexin-B1. Interestingly, Plexin-B1-deficient primary tumors showed a trend towards a reduction of local invasiveness, which could at least partially account for the lower rate of metastasis in these animals. The inventors therefore conclude that Plexin-B1 is a critical downstream mediator of ErbB-2-dependent cancer cell invasion and metastasis in breast cancer. It has recently been shown that Plexin-B1 is also expressed in ovarian cancer and that knockdown of Plexin-B1 strongly inhibits the invasiveness of the ErbB-2-overexpressing ovarian cancer cell line SK-OV-3, whereas proliferation remains unchanged (35). Consistent with this, the inventors' data show that in these cells inhibition of the interaction between ErbB-2 and Plexin-B1 by an anti-Plexin-B1 antibody strongly reduces RhoA/RhoC activity and cancer cell invasion. Therefore, it is likely that the metastasis-promoting role of Plexin-B1 is not restricted to ErbB-2-positive breast cancer but also extends to other ErbB-2-overexpressing cancers.

Conflicting data have been reported regarding the correlation of Plexin-B1 expression levels and cancer progression. While some studies have shown a downregulation of Plexin-B1 expression in melanoma and renal carcinoma as well as a correlation between low Plexin-B1 expression levels and poor prognosis in breast carcinoma (33, 36-37), others have found higher Plexin-B1 expression levels in cancer tissues as compared to normal control tissues (35, 38). In microarray analyses the inventors stratified the data according to expression of ErbB-2. In patients with ErbB-2-negative breast cancer, the inventors observed a trend towards a worse prognosis when Plexin-B1 was expressed at low levels (FIG. 9A). In striking contrast, when analyzing data from patients with ErbB-2-positive breast cancer, low levels of Plexin-B1 expression significantly correlated with good prognosis. It has previously been shown that Plexin-B1 activation can induce both anti- and pro-migratory effects depending on its association with different co-receptors (17, 39-40). Thus, it is likely that the function of Plexin-B1 is context-dependent and that Plexin-B1 may have different effects when co-expressed with particular sets of signaling partners in certain cancer types (41).

For patients with ErbB-2-overexpressing breast cancer, an anti-ErbB-2 antibody, trastuzumab, is approved to reduce the risk of cancer recurrence and metastasis. Trastuzumab treatment in combination with or after chemotherapy has shown significant clinical benefits (42). However, trastuzumab increases overall survival rates still insufficiently, is often subject to development of resistance and bears the risk of cardiac side effects (42-44). This imposes the need for the identification of new therapeutic targets for the treatment of ErbB-2-overexpressing breast cancers. The present data clearly indicate that the inhibition of Plexin-B1 reduces cancer cell invasiveness. Under in vitro conditions the inventors could show that also the blockade of the ErbB-2/Plexin-B1 interaction by an anti-Plexin-B1 antibody or the recombinant extracellular domain of Plexin-B1 (P1xB1ext) inhibits Rho activity and cancer cell invasiveness. In contrast, the therapeutic anti-ErbB-2-antibody trastuzumab did not directly interfere with ErbB-2-dependent Plexin-B1 regulation. Consistent with this, the inhibitory effects of trastuzumab and P1xB1ext on invasion of breast cancer cells in vitro were additive. These data indicate that compared to conventional anti-ErbB-2 therapy the additional inhibition of Plexin-B1 signaling downstream of ErbB-2 is likely to increase the efficacy of the therapy.

The major side effect of trastuzumab is a cardiomyopathy due to the inhibition of ErbB-2 function in cardiomyocytes (42-43). Similar effects can be seen in mice with cardiomyocyte-specific deletion of the ErbB-2 gene which develop a dilated cardiomyopathy (45-46). In contrast, Plexin-B1-deficient mice have no obvious phenotype as loss of Plexin-B1 function is obviously compensated under physiological conditions (31-32). This suggests that a therapy based on the interference with Plexin-B1-mediated signaling is less prone to side effects.

In summary, the present data show that Plexin-B1 couples ErbB-2 overexpression to Rho signaling and tumor cell invasiveness and that Plexin-B1 is centrally involved in the metastasis of ErbB-2-overexpressing breast cancer. Therefore, inhibition of the ErbB-2/Plexin-B1 interaction or of Plexin-B1-mediated signaling may reduce the risk of metastasis in patients with ErbB-2-overexpressing breast cancer and therefore represent a promising new therapeutic principle.

REFERENCES

1. Slamon, D. J., Clark, G. M., Wong, S. G., Levin, W. J., Ullrich, A., and McGuire, W. L. 1987. Human breast cancer: correlation of relapse and survival with amplification of the HER-2/neu oncogene. Science 235:177-182.
2. Slamon, D. J., Godolphin, W., Jones, L. A., Holt, J. A., Wong, S. G., Keith, D. E., Levin, W. J., Stuart, S. G., Udove, J., Ullrich, A., et al. 1989. Studies of the HER-2/neu proto-oncogene in human breast and ovarian cancer. Science 244:707-712.
3. Feigin, M. E., and Muthuswamy, S. K. 2009. ErbB receptors and cell polarity: new pathways and paradigms for understanding cell migration and invasion. Exp Cell Res 315:707-716.
4. Hynes, N. E., and MacDonald, G. 2009. ErbB receptors and signaling pathways in cancer. Curr Opin Cell Biol 21:177-184.
5. Ursini-Siegel, J., Schade, B., Cardiff, R. D., and Muller, W. J. 2007. Insights from transgenic mouse models of ERBB2-induced breast cancer. Nat Rev Cancer 7:389-397.
6. Brantley-Sieders, D. M., Zhuang, G., Hicks, D., Fang, W. B., Hwang, Y., Cates, J. M., Coffman, K., Jackson, D., Bruckheimer, E., Muraoka-Cook, R. S., et al. 2008. The receptor tyrosine kinase EphA2 promotes mammary adenocarcinoma tumorigenesis and metastatic progression in mice by amplifying ErbB2 signaling. J Clin Invest 118:64-78.
7. Guo, W., Pylayeva, Y., Pepe, A., Yoshioka, T., Muller, W. J., Inghirami, G., and Giancotti, F. G. 2006. Beta 4 integrin amplifies ErbB2 signaling to promote mammary tumorigenesis. Cell 126:489-502.
8. Bentires-Alj, M., Gil, S. G., Chan, R., Wang, Z. C., Wang, Y., Imanaka, N., Harris, L. N., Richardson, A., Neel, B. G., and Gu, H. 2006. A role for the scaffolding adapter GAB2 in breast cancer. Nat Med 12:114-121.
9. Ju, X., Katiyar, S., Wang, C., Liu, M., Jiao, X., Li, S., Zhou, J., Turner, J., Lisanti, M. P., Russell, R. G., et al. 2007. Akt1 governs breast cancer progression in vivo. Proc Natl Acad Sci USA 104:7438-7443.
10. Julien, S. G., Dube, N., Read, M., Penney, J., Paquet, M., Han, Y., Kennedy, B. P., Muller, W. J., and Tremblay, M. L. 2007. Protein tyrosine phosphatase 1B deficiency or inhibition delays ErbB2-induced mammary tumorigenesis and protects from lung metastasis. Nat Genet 39:338-346.
11. Schade, B., Lam, S. H., Cernea, D., Sanguin-Gendreau, V., Cardiff, R. D., Jung, B. L., Hallett, M., and Muller, W. J. 2007. Distinct ErbB-2 coupled signaling pathways promote mammary tumors with unique pathologic and transcriptional profiles. Cancer Res 67:7579-7588.
12. Seton-Rogers, S. E., Lu, Y., Hines, L. M., Koundinya, M., LaBaer, J., Muthuswamy, S. K., and Brugge, J. S. 2004. Cooperation of the ErbB2 receptor and transforming growth factor beta in induction of migration and invasion in mammary epithelial cells. Proc Natl Acad Sci USA 101:1257-1262.
13. Tamagnone, L., Artigiani, S., Chen, H., He, Z., Ming, G. I., Song, H., Chedotal, A., Winberg, M. L., Goodman, C. S., Poo, M., et al. 1999. Plexins are a large family of receptors for transmembrane, secreted, and GPI-anchored semaphorins in vertebrates. Cell 99:71-80.
14. Neufeld, G., and Kessler, O. 2008. The semaphorins: versatile regulators of tumour progression and tumour angiogenesis. Nat Rev Cancer 8:632-645.
15. Suzuki, K., Kumanogoh, A., and Kikutani, H. 2008. Semaphorins and their receptors in immune cell interactions. Nat Immunol 9:17-23.
16. Tran, T. S., Kolodkin, A. L., and Bharadwaj, R. 2007. Semaphorin regulation of cellular morphology. Annu Rev Cell Dev Biol 23:263-292.
17. Swiercz, J. M., Worzfeld, T., and Offermanns, S. 2008. ErbB-2 and met reciprocally regulate cellular signaling via plexin-B1. J Biol Chem 283:1893-1901.

18. Swiercz, J. M., Worzfeld, T., and Offermanns, S. 2009. Semaphorin 4D signaling requires the recruitment of phospholipase C gamma into the plexin-B1 receptor complex. Mol Cell Biol 29:6321-6334.
19. Swiercz, J. M., Kuner, R., and Offermanns, S. 2004. Plexin-B1/RhoGEF-mediated RhoA activation involves the receptor tyrosine kinase ErbB-2. J Cell Biol 165:869-880.
20. Aurandt, J., Vikis, H. G., Gutkind, J. S., Ahn, N., and Guan, K. L. 2002. The semaphorin receptor plexin-B1 signals through a direct interaction with the Rho-specific nucleotide exchange factor, LARG. Proc Natl Acad Sci USA 99:12085-12090.
21. Perrot, V., Vazquez-Prado, J., and Gutkind, J. S. 2002. Plexin B regulates Rho through the guanine nucleotide exchange factors leukemia-associated Rho GEF (LARG) and PDZ-RhoGEF. J Biol Chem 277:43115-43120.
22. Swiercz, J. M., Kuner, R., Behrens, J., and Offermanns, S. 2002. Plexin-B1 directly interacts with PDZ-RhoGEF/LARG to regulate RhoA and growth cone morphology. Neuron 35:51-63.
23. Clark, E. A., Golub, T. R., Lander, E. S., and Hynes, R. O. 2000. Genomic analysis of metastasis reveals an essential role for RhoC. Nature 406:532-535.
24. Hall, A. 2009. The cytoskeleton and cancer. Cancer Metastasis Rev 28:5-14.
25. Sahai, E., and Marshall, C. J. 2002. RHO-GTPases and cancer. Nat Rev Cancer 2:133-142.
26. Vega, F. M., and Ridley, A. J. 2008. Rho GTPases in cancer cell biology. FEBS Lett 582:2093-2101.
27. Simpson, K. J., Dugan, A. S., and Mercurio, A. M. 2004. Functional analysis of the contribution of RhoA and RhoC GTPases to invasive breast carcinoma. Cancer Res 64:8694-8701.
28. Tang, Y., Olufemi, L., Wang, M. T., and Nie, D. 2008. Role of Rho GTPases in breast cancer. Front Biosci 13:759-776.
29. Oinuma, I., Ishikawa, Y., Katoh, H., and Negishi, M. 2004. The Semaphorin 4D receptor Plexin-B1 is a GTPase activating protein for R-Ras. Science 305:862-865.
30. Prendergast, G. C. 2001. Actin' up: RhoB in cancer and apoptosis. Nat Rev Cancer 1:162-168.
31. Deng, S., Hirschberg, A., Worzfeld, T., Penachioni, J. Y., Korostylev, A., Swiercz, J. M., Vodrazka, P., Mauti, O., Stoeckli, E. T., Tamagnone, L., et al. 2007. Plexin-B2, but not Plexin-B1, critically modulates neuronal migration and patterning of the developing nervous system in vivo. J Neurosci 27:6333-6347.
32. Giacobini, P., Messina, A., Morello, F., Ferraris, N., Corso, S., Penachioni, J., Giordano, S., Tamagnone, L., and Fasolo, A. 2008. Semaphorin 4D regulates gonadotropin hormone-releasing hormone-1 neuronal migration through PlexinB1-Met complex. J Cell Biol 183:555-566.
33. Rody, A., Holtrich, U., Gaetje, R., Gehrmann, M., Engels, K., von Minckwitz, G., Loibl, S., Diallo-Danebrock, R., Ruckhaberle, E., Metzler, D., et al. 2007. Poor outcome in estrogen receptor-positive breast cancers predicted by loss of plexin B1. Clin Cancer Res 13:1115-1122.
34. Fazzari, P., Penachioni, J., Gianola, S., Rossi, F., Eickholt, B. J., Maina, F., Alexopoulou, L., Sottile, A., Comoglio, P. M., Flavell, R. A., et al. 2007. Plexin-B1 plays a redundant role during mouse development and in tumour angiogenesis. BMC Dev Biol 7:55.
35. Ye, S., Hao, X., Zhou, T., Wu, M., Wei, J., Wang, Y., Zhou, L., Jiang, X., Ji, L., Chen, Y., et al. 2010. Plexin-B1 silencing inhibits ovarian cancer cell migration and invasion. BMC Cancer 10:611.
36. Argast, G. M., Croy, C. H., Couts, K. L., Zhang, Z., Litman, E., Chan, D. C., and Ahn, N. G. 2009. Plexin B1 is repressed by oncogenic B-Raf signaling and functions as a tumor suppressor in melanoma cells. Oncogene 28:2697-2709.
37. Gomez Roman, J. J., Garay, G. O., Saenz, P., Escuredo, K., Sanz Ibayondo, C., Gutkind, S., Junquera, C., Simon, L., Martinez, A., Fernandez Luna, J. L., et al. 2008. Plexin B1 is downregulated in renal cell carcinomas and modulates cell growth. Transl Res 151:134-140.
38. Qiang, R., Wang, F., Shi, L. Y., Liu, M., Chen, S., Wan, H. Y., Li, Y. X., Li, X., Gao, S. Y., Sun, B. C., et al. 2011. Plexin-B1 is a target of miR-214 in cervical cancer and promotes the growth and invasion of HeLa cells. Int J Biochem Cell Biol 43:632-641.
39. Barberis, D., Casazza, A., Sordella, R., Corso, S., Artigiani, S., Settleman, J., Comoglio, P.M., and Tamagnone, L. 2005. p190 Rho-GTPase activating protein associates with plexins and it is required for semaphorin signalling. J Cell Sci 118:4689-4700.
40. Giordano, S., Corso, S., Conrotto, P., Artigiani, S., Gilestro, G., Barberis, D., Tamagnone, L., and Comoglio, P. M. 2002. The semaphorin 4D receptor controls invasive growth by coupling with Met. Nat Cell Biol 4:720-724.
41. Franco, M., and Tamagnone, L. 2008. Tyrosine phosphorylation in semaphorin signalling: shifting into overdrive. EMBO Rep 9:865-871.
42. Hudis, C. A. 2007. Trastuzumab—mechanism of action and use in clinical practice. N Engl J Med 357:39-51.
43. Jones, K. L., and Buzdar, A. U. 2009. Evolving novel anti-HER2 strategies. Lancet Oncol 10:1179-1187.
44. Lan, K. H., Lu, C. H., and Yu, D. 2005. Mechanisms of trastuzumab resistance and their clinical implications. Ann N Y Acad Sci 1059:70-75.
45. Crone, S. A., Zhao, Y. Y., Fan, L., Gu, Y., Minamisawa, S., Liu, Y., Peterson, K. L., Chen, J., Kahn, R., Condorelli, G., et al. 2002. ErbB2 is essential in the prevention of dilated cardiomyopathy. Nat Med 8:459-465.
46. Ozcelik, C., Erdmann, B., Pilz, B., Wettschureck, N., Britsch, S., Hubner, N., Chien, K. R., Birchmeier, C., and Garratt, A. N. 2002. Conditional mutation of the ErbB2 (HER2) receptor in cardiomyocytes leads to dilated cardiomyopathy. Proc Natl Acad Sci USA 99:8880-8885.
47. Kohler, G., and Milstein, C. 1975. Continuous cultures of fused cells secreting antibody of predefined specificity. Nature 256:495-497.
48. Hill, C. S., Wynne, J., and Treisman, R. 1995. The Rho family GTPases RhoA, Rac1, and CDC42Hs regulate transcriptional activation by SRF. Cell 81:1159-1170.
49. Wild, R., Ramakrishnan, S., Sedgewick, J., and Griffioen, A. W. 2000. Quantitative assessment of angiogenesis and tumor vessel architecture by computer-assisted digital image analysis: effects of VEGF-toxin conjugate on tumor microvessel density. Microvasc Res 59:368-376.
50. Press, M. F., Finn, R. S., Cameron, D., Di Leo, A., Geyer, C. E., Villalobos, I. E., Santiago, A., Guzman, R., Gasparyan, A., Ma, Y., et al. 2008. HER-2 gene amplification, HER-2 and epidermal growth factor receptor mRNA and protein expression, and lapatinib efficacy in women with metastatic breast cancer. Clin Cancer Res 14:7861-7870.

The invention claimed is:

1. A method for treating metastasizing cancer in a subject suffering therefrom comprising administering to the subject a therapeutically effective amount of an antagonist of a B-type plexin, wherein the antagonist prevents the interaction of the B-type plexin with ErbB-2.

2. The method of claim 1, wherein the metastasizing cancer is selected from the group consisting of breast cancer, ovarian cancer, stomach cancer, and uterine cancer.

3. The method of claim 1, wherein the antagonist is a nucleic acid that is capable of hybridizing specifically to the B-type plexin gene or to its transcripts and that prevents expression of the B-type plexin polypeptide.

4. The method of claim 3, wherein the nucleic acid is selected from the group consisting of an siRNA, a micro RNA, an antisense RNA, a morpholino oligonucleotides, a ribozymes, and a triple helix forming agents.

5. The method of claim 1, wherein the antagonist specifically binds to the B-type plexin polypeptide and inhibits binding of the B-type plexin polypeptide to Erb-B2.

6. The method of claim 5, wherein the antagonist binds to the extracellular domain of B-type plexin.

7. The method of claim 5, wherein the antagonist is selected from the group consisting of an antibody, an aptamer, a peptides, and a polypeptides.

8. The method of claim 1, wherein the antagonist is administered in combination with a cytotoxic compound, wherein the compound inhibits cell proliferation or differentiation of cancer cells, induces apoptosis of cancer cells, or prevents tumor angiogenesis.

9. The method of claim 1, wherein the compound is selected from the group consisting of trastuzumab, bevacizumab, tamoxifen, 5-fluorouracil, methotrexate, gemcitabine, Ara-C(Cytarabine), CCNU (Chloroethylcyclohexylnotrisourea), hydroxyurea, adriamycin, mitomycin C, mitoxantrone, doxorubicin, epirubicin, cisplatin, carboplatin, cyclophosphamide, ifosfamide, paclitaxel, docetaxel, vincristine, etoposide, irinotecan, and topotecan.

10. The method of claim 1, wherein the antagonist is a B-type plexin polypeptide that lacks a functional intracellular domain.

11. The method of claim 7, wherein the agonist is an antibody.

* * * * *

SEQUENCE LISTING

<160> NUMBER OF SEQ ID NOS: 20

<210> SEQ ID NO 1
<211> LENGTH: 7143
<212> TYPE: DNA
<213> ORGANISM: Homo sapiens

<400> SEQUENCE: 1

| | | | | | |
|---|---|---|---|---|---|
| agggccaggt | gcgcagggga | gaaacaaggc | gccttggagt | tcaggtgact | cccacacggg | 60 |
| tcatgctgtt | gtctcctgat | ccagccggcc | ctgccaggtg | accatgcctg | ctctgggccc | 120 |
| agctcttctc | caggctctct | gggccgggtg | gtcctcacc | ctccagcccc | ttccaccaac | 180 |
| tgcattcact | cccaatggca | cgtatctgca | gcacctggca | agggacccca | cctcaggcac | 240 |
| cctctacctg | ggggctacca | acttcctgtt | ccagctgagc | cctgggctgc | agctggaggc | 300 |
| cacagtgtcc | accggccctg | tgctagacag | cagggactgc | ctgccacctg | tgatgcctga | 360 |
| tgagtgcccc | caggccagc | ctaccaacaa | cccgaatcag | ctgctcctgg | tgagcccagg | 420 |
| ggccctggtg | gtatgcggga | gcgtgcacca | ggggtctgt | gaacagcggc | gcctggggca | 480 |
| gctcgagcag | ctgctgctgc | ggccagagcg | gcctggggac | acacaatatg | tggctgccaa | 540 |
| tgatcctgcg | gtcagcacgg | tggggctggt | agcccagggc | ttggcagggg | agcccctcct | 600 |
| gtttgtgggg | cgaggataca | ccagcagggg | tgtggggggg | ggcattccac | ccatcacaac | 660 |
| ccgggccctg | tggccgcccg | accccaagc | tgccttctcc | tatgaggaga | cagccaagct | 720 |
| ggcagtgggc | cgcctctccg | agtacagcca | ccacttcgtg | agtgcctttg | cacgtggggc | 780 |
| cagcgcctac | ttcctgttcc | tgcggcggga | cctgcaggct | cagtctagag | cttttcgtgc | 840 |
| ctatgtatct | cgagtgtgtc | tccgggacca | gcactactac | tcctatgtgg | agttgcctct | 900 |
| ggcctgcgaa | ggtggccgct | acgggctgat | ccaggctgca | gctgtggcca | cgtccaggga | 960 |
| ggtggcgcat | ggggaggtgc | tctttgcagc | tttctcctcg | gctgcacccc | ccactgtggg | 1020 |
| ccggcccca | tcggcggctg | ctggggcatc | tggagcctct | gccctctgtg | ccttccccct | 1080 |
| ggatgaggtg | gaccggcttg | ctaatcgcac | gcgagatgcc | tgctacaccc | gggagggtcg | 1140 |
| tgctgaggat | gggaccgagg | tggcctacat | cgagtatgat | gtcaattctg | actgtgcaca | 1200 |
| gctgccagtg | gacaccctgg | atgcttatcc | ctgtggctca | gaccacacgc | ccagccccat | 1260 |
| ggccagccgg | gtcccgctgg | aagccacacc | aattctggag | tggccaggga | ttcagctaac | 1320 |
| agctgtggca | gtcaccatgg | aagatggaca | caccatcgct | ttcctgggtg | atagtcaagg | 1380 |
| gcagctgcac | agggtctact | tgggcccagg | gagcgatggc | cacccatact | ccacacagag | 1440 |
| catccagcag | gggtctgcag | tgagcagaga | cctcacctt | gatgggacct | ttgagcacct | 1500 |
| gtatgtcatg | acccagagca | cacttctgaa | ggttcctgtg | gcttcctgtg | ctcagcacct | 1560 |
| ggactgtgca | tcttgccttg | ctcacaggga | cccatactgt | gggtggtgcg | tgctccttgg | 1620 |
| caggtgcagt | cgccgttctg | agtgctcgag | gggccagggc | ccagagcagt | ggctatggag | 1680 |
| cttccagcct | gagctgggct | gtctgcaagt | ggcagccatg | agtcctgcca | acatcagccg | 1740 |
| agaggagacg | agggaggttt | tcctatcagt | gccagacctg | ccaccctgt | ggccagggga | 1800 |
| gtcatattcc | tgccactttg | gggaacatca | gagtcctgcc | ctgctgactg | gttctggtgt | 1860 |
| gatgtgcccc | tccccagacc | ctagtgaggc | cccagtgctg | ccgagaggag | ccgactacgt | 1920 |
| atccgtgagc | gtggagctca | gatttggcgc | tgttgtgatc | gccaaaactt | ccctctcttt | 1980 |
| ctatgactgt | gtggcggtca | ctgaactccg | cccatctgcg | cagtgccagg | cctgtgtgag | 2040 |
| cagccgctgg | gggtgtaact | ggtgtgtctg | gcagcacctg | tgcacccaca | aggcctcgtg | 2100 |

```
tgatgctggg cccatggttg caagccatca gagcccgctt gtctcccag accctcctgc    2160 aagaggtgga cccagcccct ccccacccac agccccaaa gccctggcca ccctgctcc    2220 tgacacccctt cccgtggagc ctggggctcc ctccacagcc acagcttcgg acatctcacc  2280
tggggctagt ccttccctgc tcagccctg ggggccatgg gcaggttctg gctccatatc   2340
ttcccctggc tccacagggt cgcctctcca tgaggagccc tcccctccca gcccccaaaa   2400
tggacctgga accgctgtcc ctgccccac tgacttcaga ccctcagcca cctgagga     2460 cctcttggcc tccccgctgt caccgtcaga ggtagcagca gtgcccctg cagaccctgg   2520 ccccgaggct cttcatccca cagtgccct ggacctgccc cctgccactg ttcctgccac   2580
cactttccca ggggccatgg gctccgtgaa gcccgccctg gactggctca cgagagaagg  2640
cggcgagctg cccgaggcgg acgagtggac gggggtgac gcacccgcct tctccacttc   2700
caccctcctc tcaggtgatg gagactcagc agagcttgag ggccctcccg cccccctcat  2760
cctcccgtcc agcctcgact accagtatga cacccccggg ctctgggagc tggaagaggc  2820
gaccttgggg gcaagctcct gcccctgtgt ggagagcgtt cagggctcca cgttgatgcc  2880
ggtccatgtg gagcgggaaa tccggctgct aggcaggaac ctgcacctttt tccaggatgg 2940 cccaggagac aatgagtgtg tgatggagct ggagggcctc gaggtggtgg ttgaggcccg  3000
ggtcgagtgt gagccaccte cagatacccca gtgccatgtc acctgccagc agcaccagct 3060
cagctatgag gctctgcagc cggagctccg tgtggggctg tttctgcgtc gggccggccg  3120
tctgcgtgtg gacagtgctg aggggctgca tgtggtactg tatgactgtt ccgtgggaca  3180
tggagactgc agccgctgcc aaactgccat gccccagtat ggctgtgtgt ggtgtgaggg  3240
ggagcgtcca cgttgtgtga cccgggaggc ctgtggtgag gctgaggctg tggccaccca  3300
gtgcccagcg cccctcatcc actcggtgga gccactgact gggcctgtag acggaggcac  3360
ccgtgtcacc atcaggggct ccaacctggg ccagcatgtg caggatgtgc tgggcatggt  3420
cacggtggct ggagtgccct gtgctgtgga tgccaggag tacgaggtct ccagcagcct   3480
cgtgtgcatc accggggcca gtggggagga ggtggccggc gccacagcgg tggaggtgcc  3540
gggaagagga cgtggtgtct cagaacacga ctttgcctac caggatccga aggtccattc  3600
catcttcccg gcccgcggcc ccagagctgg gggcacccgt ctcaccctga atggctccaa  3660
gctcctgact gggcggctgg aggacatccg agtggtggtt ggagaccagc cttgtcactt  3720
gctgccggag cagcagtcag aacaactgcg gtgtgagacc agcccacgcc ccacgcctgc  3780
cacgctccct gtggctgtgt ggtttggggc cacgagcgg aggcttcaac gcggacagtt   3840
caagtatacc ttggacccca acatcacctc tgctggcccc accaagagct tcctcagtgg  3900
aggacgtgag atatgcgtcc gtggccagaa tctggacgtg gtacagacgc caagaatccg  3960
ggtgaccgtg gtctcgagaa tgctgcagcc cagccagggg cttggacgga ggcgtcgcgt  4020
ggtcccggaa acggcatgtt cccttggacc ctcctgcagt agccagcaat ttgaggagcc  4080
gtgccatgtc aactcctccc agctcatcac gtgccgcaca cctgccctcc caggcctgcc  4140
tgaggacccc tgggtccggg tggaatttat ccttgacaac ctggtctttg actttgcaac  4200
actgaacccc acacctttct cctatgaggc cgaccccacc ctgcagccac tcaaccctga  4260
ggaccccacc atgccattcc ggcacaagcc tgggagtgtg ttctccgtgg aggggagaa   4320 cctggacctt gcaatgtcca aggaggaggt ggtggctatg ataggggatg gccctgtgt   4380 ggtgaagacg ctgacgcggc accacctgta ctgcgagccc ccgtggagc agcccctgcc    4440
```

```
acggcaccat gccctccgag aggcacctga ctctttgcct gagttcacgg tgcagatggg   4500
gaacttgcgc ttctccctgg gtcacgtgca gtatgacggc gagagccctg gggcttttcc   4560
tgtggcagcc caggtgggct tgggggtggg cacctctctt ctggctctgg gtgtcatcat   4620
cattgtcctc atgtacagga ggaagagcaa gcaggccctg agggactata agaaggttca   4680
gatccagctg gagaatctgg agagcagtgt gcgggaccgc tgcaagaagg aattcacaga   4740
cctcatgact gagatgaccg atctcaccag tgacctcctg gcagcggca tcccttcct    4800 cgactacaag gtgtatgcgg agaggatctt cttccctggg caccgcgagt cgcccttgca   4860
ccgggacctg ggtgtgcctg agagcagacg gcccactgtg gagcaagggc tggggcagct   4920
ctctaacctg ctcaacagca agctcttcct caccaagttc atccacacgc tggagagcca   4980
gcgcaccttt tcagctcggg accgtgccta cgtggcatct ctgctcaccg tggcactgca   5040
tgggaagctt gagtatttca ctgacatcct ccgcactctc tcagtgacc tggttgccca    5100 gtatgtggcc aagaacccca agctgatgct gcgcaggaca gagactgtgg tggagaagct   5160
gctcaccaac tggatgtcca tctgtctgta taccttcgtg agggactccg taggggagcc   5220
tctgtacatg ctctttcgag ggattaagca ccaagtggat aaggggccag tggacagtgt   5280
gacaggcaag gccaaataca ccttgaacga caaccgcctg ctcagagagg atgtggagta   5340
ccgtcccctg accttgaatg cactattggc tgtgggcct ggggcaggag aggcccaggg    5400
cgtgcccgtg aaggtcctag actgtgacac catctcccag gcaaaggaga gatgctgga   5460 ccagctttat aaaggagtgc ctctcaccca gcggccagac cctcgcaccc ttgatgttga   5520
gtggcggtct ggggtggccg ggcacctcat tctttctgac gaggatgtca cttctgaggt   5580
ccagggtctg tggaggcgcc tgaacacact gcagcattac aaggtcccag atggagcaac   5640
tgtgcccctc gtccctgcc tcaccaagca tgtgctccgg gaaaaccagg attatgtccc    5700
tggagagcgg accccaatgc tggaggatgt agatgagggg ggcatccggc cctggcacct   5760
ggtgaagcca agtgatgagc cggagccgcc caggcctcgg aggggcagcc ttcggggcgg   5820
ggagcgtgag cgcgccaagg ccatccctga gatctacctg acccgcctgc tgtccatgaa   5880
gggcaccctg cagaagttcg tggatgacct gttccaggtg attctcagca ccagccgccc   5940
cgtgccgctc gctgtgaagt acttctttga cctgctggat gagcaggccc agcagcatgg   6000
catctccgac caggacacca tccacatctg gaagaccaac agcttgcctc tgaggttctg   6060
gatcaatata ataaaaaacc cgcagtttgt gttcgacgtg caaacatctg ataacatgga   6120
tgcggtgctc cttgtcattg cacagacctt catggacgcc tgcaccctgg ccgaccacaa   6180
gctgggccgg gactccccga tcaacaaact tctgtatgca cgggacattc cccggtacaa   6240
gcggatggtg gaaaggtact atgcagacat cagacagact gtcccagcca gcgaccaaga   6300
gatgaactct gtcctggctg aactgtcctg gaactactcc ggagacctcg gggcgcgagt   6360
ggccctgcat gaactctaca gtacatcaa caagtactat gaccagatca tcactgccct    6420
ggaggaggat ggcacggccc agaagatgca gctgggctat cggctccagc agattgcagc   6480
tgctgtggaa acaaggtca cagatctata ggaacccagg agccacggcc tgctgttgct    6540
tcagcctggc ctgggcagcc ctggaagctc ggaggagagg ccaccttctt aggtgcctgt   6600
agtgactgac aagcagagtt agtggaaggt gactcccagt ctcctggtgg ctctggcctc   6660
ggccctgctg gatccacctc ctagacccgg ggcctcaagg ctcatggggt agtacccagc   6720
ctgctccccg agtccagcga ccctgtgaca ccggtctgca gggagttggg gactaagggc   6780
ttccagagag tggctggaag agactccagg cccctgggga gactgtactg ttcctgaaca   6840
```

-continued

```
ctggccttgg ccacactggg attcggagag gaaggaggag agccccatgc ttcctgtctg    6900
cctcctccac catccctgac ctcagttgag ctgcctctgg ccttgttgct gctgccacat    6960
cctaggtcta agagttgaac gcctctccta ggccactaca aactgacccc tcagcagggc    7020
tggctgccac agggctgccc tgcctcatag gtagccatgg tgagggctat ctgctgcagg    7080
ggggtcttgg ggagagtggt gactccattg acccagcttt tcattaaagg ataacacact    7140
gca                                                                  7143
```

<210> SEQ ID NO 2
<211> LENGTH: 2135
<212> TYPE: PRT
<213> ORGANISM: Homo sapiens

<400> SEQUENCE: 2

```
Met Pro Ala Leu Gly Pro Ala Leu Leu Gln Ala Leu Trp Ala Gly Trp
1               5                   10                  15

Val Leu Thr Leu Gln Pro Leu Pro Pro Thr Ala Phe Thr Pro Asn Gly
            20                  25                  30

Thr Tyr Leu Gln His Leu Ala Arg Asp Pro Thr Ser Gly Thr Leu Tyr
        35                  40                  45

Leu Gly Ala Thr Asn Phe Leu Phe Gln Leu Ser Pro Gly Leu Gln Leu
    50                  55                  60

Glu Ala Thr Val Ser Thr Gly Pro Val Leu Asp Ser Arg Asp Cys Leu
65                  70                  75                  80

Pro Pro Val Met Pro Asp Glu Cys Pro Gln Ala Gln Pro Thr Asn Asn
                85                  90                  95

Pro Asn Gln Leu Leu Leu Val Ser Pro Gly Ala Leu Val Val Cys Gly
            100                 105                 110

Ser Val His Gln Gly Val Cys Glu Gln Arg Arg Leu Gly Gln Leu Glu
        115                 120                 125

Gln Leu Leu Leu Arg Pro Glu Arg Pro Gly Asp Thr Gln Tyr Val Ala
    130                 135                 140

Ala Asn Asp Pro Ala Val Ser Thr Val Gly Leu Val Ala Gln Gly Leu
145                 150                 155                 160

Ala Gly Glu Pro Leu Leu Phe Val Gly Arg Gly Tyr Thr Ser Arg Gly
                165                 170                 175

Val Gly Gly Gly Ile Pro Pro Ile Thr Thr Arg Ala Leu Trp Pro Pro
            180                 185                 190

Asp Pro Gln Ala Ala Phe Ser Tyr Glu Glu Thr Ala Lys Leu Ala Val
        195                 200                 205

Gly Arg Leu Ser Glu Tyr Ser His His Phe Val Ser Ala Phe Ala Arg
    210                 215                 220

Gly Ala Ser Ala Tyr Phe Leu Phe Leu Arg Arg Asp Leu Gln Ala Gln
225                 230                 235                 240

Ser Arg Ala Phe Arg Ala Tyr Val Ser Arg Val Cys Leu Arg Asp Gln
                245                 250                 255

His Tyr Tyr Ser Tyr Val Glu Leu Pro Leu Ala Cys Glu Gly Gly Arg
            260                 265                 270

Tyr Gly Leu Ile Gln Ala Ala Val Ala Thr Ser Arg Glu Val Ala
        275                 280                 285

His Gly Glu Val Leu Phe Ala Ala Phe Ser Ser Ala Ala Pro Pro Thr
    290                 295                 300

Val Gly Arg Pro Pro Ser Ala Ala Ala Gly Ala Ser Gly Ala Ser Ala
```

```
            305                 310                 315                 320
Leu Cys Ala Phe Pro Leu Asp Glu Val Asp Arg Leu Ala Asn Arg Thr
                325                 330                 335
Arg Asp Ala Cys Tyr Thr Arg Glu Gly Arg Ala Glu Asp Gly Thr Glu
                340                 345                 350
Val Ala Tyr Ile Glu Tyr Asp Val Asn Ser Asp Cys Ala Gln Leu Pro
                355                 360                 365
Val Asp Thr Leu Asp Ala Tyr Pro Cys Gly Ser Asp His Thr Pro Ser
        370                 375                 380
Pro Met Ala Ser Arg Val Pro Leu Glu Ala Thr Pro Ile Leu Glu Trp
385                 390                 395                 400
Pro Gly Ile Gln Leu Thr Ala Val Ala Val Thr Met Glu Asp Gly His
                405                 410                 415
Thr Ile Ala Phe Leu Gly Asp Ser Gln Gly Gln Leu His Arg Val Tyr
                420                 425                 430
Leu Gly Pro Gly Ser Asp Gly His Pro Tyr Ser Thr Gln Ser Ile Gln
            435                 440                 445
Gln Gly Ser Ala Val Ser Arg Asp Leu Thr Phe Asp Gly Thr Phe Glu
        450                 455                 460
His Leu Tyr Val Met Thr Gln Ser Thr Leu Leu Lys Val Pro Val Ala
465                 470                 475                 480
Ser Cys Ala Gln His Leu Asp Cys Ala Ser Cys Leu Ala His Arg Asp
                485                 490                 495
Pro Tyr Cys Gly Trp Cys Val Leu Leu Gly Arg Cys Ser Arg Arg Ser
            500                 505                 510
Glu Cys Ser Arg Gly Gln Gly Pro Glu Gln Trp Leu Trp Ser Phe Gln
        515                 520                 525
Pro Glu Leu Gly Cys Leu Gln Val Ala Ala Met Ser Pro Ala Asn Ile
        530                 535                 540
Ser Arg Glu Glu Thr Arg Glu Val Phe Leu Ser Val Pro Asp Leu Pro
545                 550                 555                 560
Pro Leu Trp Pro Gly Glu Ser Tyr Ser Cys His Phe Gly Glu His Gln
            565                 570                 575
Ser Pro Ala Leu Leu Thr Gly Ser Gly Val Met Cys Pro Ser Pro Asp
            580                 585                 590
Pro Ser Glu Ala Pro Val Leu Pro Arg Gly Ala Asp Tyr Val Ser Val
        595                 600                 605
Ser Val Glu Leu Arg Phe Gly Ala Val Val Ile Ala Lys Thr Ser Leu
        610                 615                 620
Ser Phe Tyr Asp Cys Val Ala Val Thr Glu Leu Arg Pro Ser Ala Gln
625                 630                 635                 640
Cys Gln Ala Cys Val Ser Ser Arg Trp Gly Cys Asn Trp Cys Val Trp
                645                 650                 655
Gln His Leu Cys Thr His Lys Ala Ser Cys Asp Ala Gly Pro Met Val
                660                 665                 670
Ala Ser His Gln Ser Pro Leu Val Ser Pro Asp Pro Ala Arg Gly
            675                 680                 685
Gly Pro Ser Pro Ser Pro Thr Ala Pro Lys Ala Leu Ala Thr Pro
        690                 695                 700
Ala Pro Asp Thr Leu Pro Val Glu Pro Gly Ala Pro Ser Thr Ala Thr
705                 710                 715                 720
Ala Ser Asp Ile Ser Pro Gly Ala Ser Pro Ser Leu Leu Ser Pro Trp
                725                 730                 735
```

-continued

```
Gly Pro Trp Ala Gly Ser Gly Ser Ile Ser Ser Pro Gly Ser Thr Gly
                740                 745                 750
Ser Pro Leu His Glu Glu Pro Ser Pro Ser Pro Gln Asn Gly Pro
        755                 760                 765
Gly Thr Ala Val Pro Ala Pro Thr Asp Phe Arg Pro Ser Ala Thr Pro
770                 775                 780
Glu Asp Leu Leu Ala Ser Pro Leu Ser Pro Ser Glu Val Ala Ala Val
785                 790                 795                 800
Pro Pro Ala Asp Pro Gly Pro Glu Ala Leu His Pro Thr Val Pro Leu
                805                 810                 815
Asp Leu Pro Pro Ala Thr Val Pro Ala Thr Thr Phe Pro Gly Ala Met
                820                 825                 830
Gly Ser Val Lys Pro Ala Leu Asp Trp Leu Thr Arg Glu Gly Gly Glu
                835                 840                 845
Leu Pro Glu Ala Asp Glu Trp Thr Gly Gly Asp Ala Pro Ala Phe Ser
850                 855                 860
Thr Ser Thr Leu Leu Ser Gly Asp Gly Asp Ser Ala Glu Leu Glu Gly
865                 870                 875                 880
Pro Pro Ala Pro Leu Ile Leu Pro Ser Ser Leu Asp Tyr Gln Tyr Asp
                885                 890                 895
Thr Pro Gly Leu Trp Glu Leu Glu Ala Thr Leu Gly Ala Ser Ser
                900                 905                 910
Cys Pro Cys Val Glu Ser Val Gln Gly Ser Thr Leu Met Pro Val His
                915                 920                 925
Val Glu Arg Glu Ile Arg Leu Leu Gly Arg Asn Leu His Leu Phe Gln
                930                 935                 940
Asp Gly Pro Gly Asp Asn Glu Cys Val Met Glu Leu Glu Gly Leu Glu
945                 950                 955                 960
Val Val Val Glu Ala Arg Val Glu Cys Glu Pro Pro Asp Thr Gln
                965                 970                 975
Cys His Val Thr Cys Gln Gln His Gln Leu Ser Tyr Glu Ala Leu Gln
                980                 985                 990
Pro Glu Leu Arg Val Gly Leu Phe Leu Arg Arg Ala Gly Arg Leu Arg
                995                 1000                1005
Val Asp Ser Ala Glu Gly Leu His Val Val Leu Tyr Asp Cys Ser
    1010                1015                1020
Val Gly His Gly Asp Cys Ser Arg Cys Gln Thr Ala Met Pro Gln
    1025                1030                1035
Tyr Gly Cys Val Trp Cys Glu Gly Glu Arg Pro Arg Cys Val Thr
    1040                1045                1050
Arg Glu Ala Cys Gly Glu Ala Glu Val Ala Thr Gln Cys Pro
    1055                1060                1065
Ala Pro Leu Ile His Ser Val Glu Pro Leu Thr Gly Pro Val Asp
    1070                1075                1080
Gly Gly Thr Arg Val Thr Ile Arg Gly Ser Asn Leu Gly Gln His
    1085                1090                1095
Val Gln Asp Val Leu Gly Met Val Thr Val Ala Gly Val Pro Cys
    1100                1105                1110
Ala Val Asp Ala Gln Glu Tyr Glu Val Ser Ser Leu Val Cys
    1115                1120                1125
Ile Thr Gly Ala Ser Gly Glu Glu Val Ala Gly Ala Thr Ala Val
    1130                1135                1140
```

```
Glu Val Pro Gly Arg Gly Arg Gly Val Ser Glu His Asp Phe Ala
    1145            1150                1155

Tyr Gln Asp Pro Lys Val His Ser Ile Phe Pro Ala Arg Gly Pro
    1160            1165                1170

Arg Ala Gly Gly Thr Arg Leu Thr Leu Asn Gly Ser Lys Leu Leu
    1175            1180                1185

Thr Gly Arg Leu Glu Asp Ile Arg Val Val Gly Asp Gln Pro
    1190            1195                1200

Cys His Leu Leu Pro Glu Gln Gln Ser Glu Gln Leu Arg Cys Glu
    1205            1210                1215

Thr Ser Pro Arg Pro Thr Pro Ala Thr Leu Pro Val Ala Val Trp
    1220            1225                1230

Phe Gly Ala Thr Glu Arg Arg Leu Gln Arg Gly Gln Phe Lys Tyr
    1235            1240                1245

Thr Leu Asp Pro Asn Ile Thr Ser Ala Gly Pro Thr Lys Ser Phe
    1250            1255                1260

Leu Ser Gly Gly Arg Glu Ile Cys Val Arg Gly Gln Asn Leu Asp
    1265            1270                1275

Val Val Gln Thr Pro Arg Ile Arg Val Thr Val Val Ser Arg Met
    1280            1285                1290

Leu Gln Pro Ser Gln Gly Leu Gly Arg Arg Arg Val Val Pro
    1295            1300                1305

Glu Thr Ala Cys Ser Leu Gly Pro Ser Cys Ser Ser Gln Gln Phe
    1310            1315                1320

Glu Glu Pro Cys His Val Asn Ser Ser Gln Leu Ile Thr Cys Arg
    1325            1330                1335

Thr Pro Ala Leu Pro Gly Leu Pro Glu Asp Pro Trp Val Arg Val
    1340            1345                1350

Glu Phe Ile Leu Asp Asn Leu Val Phe Asp Phe Ala Thr Leu Asn
    1355            1360                1365

Pro Thr Pro Phe Ser Tyr Glu Ala Asp Pro Thr Leu Gln Pro Leu
    1370            1375                1380

Asn Pro Glu Asp Pro Thr Met Pro Phe Arg His Lys Pro Gly Ser
    1385            1390                1395

Val Phe Ser Val Glu Gly Glu Asn Leu Asp Leu Ala Met Ser Lys
    1400            1405                1410

Glu Glu Val Val Ala Met Ile Gly Asp Gly Pro Cys Val Val Lys
    1415            1420                1425

Thr Leu Thr Arg His His Leu Tyr Cys Glu Pro Pro Val Glu Gln
    1430            1435                1440

Pro Leu Pro Arg His His Ala Leu Arg Glu Ala Pro Asp Ser Leu
    1445            1450                1455

Pro Glu Phe Thr Val Gln Met Gly Asn Leu Arg Phe Ser Leu Gly
    1460            1465                1470

His Val Gln Tyr Asp Gly Glu Ser Pro Gly Ala Phe Pro Val Ala
    1475            1480                1485

Ala Gln Val Gly Leu Gly Val Gly Thr Ser Leu Leu Ala Leu Gly
    1490            1495                1500

Val Ile Ile Ile Val Leu Met Tyr Arg Arg Lys Ser Lys Gln Ala
    1505            1510                1515

Leu Arg Asp Tyr Lys Lys Val Gln Ile Gln Leu Glu Asn Leu Glu
    1520            1525                1530

Ser Ser Val Arg Asp Arg Cys Lys Lys Glu Phe Thr Asp Leu Met
```

-continued

```
            1535                1540                1545
Thr Glu Met Thr Asp Leu Thr Ser Asp Leu Leu Gly Ser Gly Ile
            1550                1555                1560
Pro Phe Leu Asp Tyr Lys Val Tyr Ala Glu Arg Ile Phe Phe Pro
            1565                1570                1575
Gly His Arg Glu Ser Pro Leu His Arg Asp Leu Gly Val Pro Glu
            1580                1585                1590
Ser Arg Arg Pro Thr Val Glu Gln Gly Leu Gly Gln Leu Ser Asn
            1595                1600                1605
Leu Leu Asn Ser Lys Leu Phe Leu Thr Lys Phe Ile His Thr Leu
            1610                1615                1620
Glu Ser Gln Arg Thr Phe Ser Ala Arg Asp Arg Ala Tyr Val Ala
            1625                1630                1635
Ser Leu Leu Thr Val Ala Leu His Gly Lys Leu Glu Tyr Phe Thr
            1640                1645                1650
Asp Ile Leu Arg Thr Leu Leu Ser Asp Leu Val Ala Gln Tyr Val
            1655                1660                1665
Ala Lys Asn Pro Lys Leu Met Leu Arg Arg Thr Glu Thr Val Val
            1670                1675                1680
Glu Lys Leu Leu Thr Asn Trp Met Ser Ile Cys Leu Tyr Thr Phe
            1685                1690                1695
Val Arg Asp Ser Val Gly Glu Pro Leu Tyr Met Leu Phe Arg Gly
            1700                1705                1710
Ile Lys His Gln Val Asp Lys Gly Pro Val Asp Ser Val Thr Gly
            1715                1720                1725
Lys Ala Lys Tyr Thr Leu Asn Asp Asn Arg Leu Leu Arg Glu Asp
            1730                1735                1740
Val Glu Tyr Arg Pro Leu Thr Leu Asn Ala Leu Leu Ala Val Gly
            1745                1750                1755
Pro Gly Ala Gly Glu Ala Gln Gly Val Pro Val Lys Val Leu Asp
            1760                1765                1770
Cys Asp Thr Ile Ser Gln Ala Lys Glu Lys Met Leu Asp Gln Leu
            1775                1780                1785
Tyr Lys Gly Val Pro Leu Thr Gln Arg Pro Asp Pro Arg Thr Leu
            1790                1795                1800
Asp Val Glu Trp Arg Ser Gly Val Ala Gly His Leu Ile Leu Ser
            1805                1810                1815
Asp Glu Asp Val Thr Ser Glu Val Gln Gly Leu Trp Arg Arg Leu
            1820                1825                1830
Asn Thr Leu Gln His Tyr Lys Val Pro Asp Gly Ala Thr Val Ala
            1835                1840                1845
Leu Val Pro Cys Leu Thr Lys His Val Leu Arg Glu Asn Gln Asp
            1850                1855                1860
Tyr Val Pro Gly Glu Arg Thr Pro Met Leu Glu Asp Val Asp Glu
            1865                1870                1875
Gly Gly Ile Arg Pro Trp His Leu Val Lys Pro Ser Asp Glu Pro
            1880                1885                1890
Glu Pro Pro Arg Pro Arg Arg Gly Ser Leu Arg Gly Gly Glu Arg
            1895                1900                1905
Glu Arg Ala Lys Ala Ile Pro Glu Ile Tyr Leu Thr Arg Leu Leu
            1910                1915                1920
Ser Met Lys Gly Thr Leu Gln Lys Phe Val Asp Asp Leu Phe Gln
            1925                1930                1935
```

```
Val Ile Leu Ser Thr Ser Arg Pro Val Pro Leu Ala Val Lys Tyr
    1940                1945                1950

Phe Phe Asp Leu Leu Asp Glu Gln Ala Gln Gln His Gly Ile Ser
    1955                1960                1965

Asp Gln Asp Thr Ile His Ile Trp Lys Thr Asn Ser Leu Pro Leu
    1970                1975                1980

Arg Phe Trp Ile Asn Ile Ile Lys Asn Pro Gln Phe Val Phe Asp
    1985                1990                1995

Val Gln Thr Ser Asp Asn Met Asp Ala Val Leu Leu Val Ile Ala
    2000                2005                2010

Gln Thr Phe Met Asp Ala Cys Thr Leu Ala Asp His Lys Leu Gly
    2015                2020                2025

Arg Asp Ser Pro Ile Asn Lys Leu Leu Tyr Ala Arg Asp Ile Pro
    2030                2035                2040

Arg Tyr Lys Arg Met Val Glu Arg Tyr Tyr Ala Asp Ile Arg Gln
    2045                2050                2055

Thr Val Pro Ala Ser Asp Gln Glu Met Asn Ser Val Leu Ala Glu
    2060                2065                2070

Leu Ser Trp Asn Tyr Ser Gly Asp Leu Gly Ala Arg Val Ala Leu
    2075                2080                2085

His Glu Leu Tyr Lys Tyr Ile Asn Lys Tyr Tyr Asp Gln Ile Ile
    2090                2095                2100

Thr Ala Leu Glu Glu Asp Gly Thr Ala Gln Lys Met Gln Leu Gly
    2105                2110                2115

Tyr Arg Leu Gln Gln Ile Ala Ala Ala Val Glu Asn Lys Val Thr
    2120                2125                2130

Asp Leu
    2135

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      siRNA human plexin B1 oligonucleotide

<400> SEQUENCE: 3
accacgguca cccggauuc                                                   19

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer 5' plexin

<400> SEQUENCE: 4
cagccaccac ttcgtgagtg cc                                               22

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer 3' plexin

<400> SEQUENCE: 5
```
ggtgactgcc acagctgtta gctg                                    24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer 5' plexin-B1

<400> SEQUENCE: 6
cagccaccac ttcgtgagtg cc                                      22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer 5' beta-actin

<400> SEQUENCE: 7
atggatgatg atatcgccgc g                                       21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer 3' beta-actin

<400> SEQUENCE: 8
gaagcatttg cggtggacga t                                       21

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer 5' plexin-B1

<400> SEQUENCE: 9
ggtggaaagg tactatgcag acatcag                                 27

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer 3' plexin-B1

<400> SEQUENCE: 10
cctcctccag ggcagtgatg atc                                     23

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer 5' beta-actin

<400> SEQUENCE: 11

```
ggtgtgatgg tgggaatggg tcag                                              24
```

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer 3' beta-actin

<400> SEQUENCE: 12

```
gaggaagagg atgcggcagt gg                                                22
```

<210> SEQ ID NO 13
<211> LENGTH: 82
<212> TYPE: PRT
<213> ORGANISM: Mus musculus
<220> FEATURE:
<221> NAME/KEY: MOD_RES
<222> LOCATION: (3)..(4)
<223> OTHER INFORMATION: Any amino acid

<400> SEQUENCE: 13

```
His Leu Xaa Xaa Pro Thr Ser Ser Asn Thr Ala Tyr Met Gln Leu Ser
1               5                   10                  15

Ser Leu Thr Ser Glu Asp Ser Ala Val Tyr Tyr Cys Val Arg Asn Tyr
            20                  25                  30

Gly Tyr Trp Gly Gln Gly Thr Leu Val Thr Val Ser Ala Ala Lys Thr
        35                  40                  45

Thr Pro Pro Ser Val Tyr Pro Leu Ala Pro Gly Ser Ala Ala Gln Thr
    50                  55                  60

Asn Ser Met Gly Pro Trp Asp Leu Arg Lys Leu Ser Leu Asp Tyr Ala
65                  70                  75                  80

Glu Lys
```

<210> SEQ ID NO 14
<211> LENGTH: 16
<212> TYPE: PRT
<213> ORGANISM: Mus musculus

<400> SEQUENCE: 14

```
Asn Glu Asn Val Ala Gly Ser Phe Leu Glu Leu Ala Val Trp His Gln
1               5                   10                  15
```

<210> SEQ ID NO 15
<211> LENGTH: 46
<212> TYPE: PRT
<213> ORGANISM: Mus musculus

<400> SEQUENCE: 15

```
Lys Asp Gln Val Gln Leu Val Gln Ser Ser Thr Tyr Ser Val Pro Thr
1               5                   10                  15

Ala Pro Arg Leu Leu Leu His Pro Met Ala Ser Leu Gly Leu Ile Ala
            20                  25                  30

Leu Ala Phe Gly Ser Asp Glu Asp Lys Asn Gly Trp Ile Leu
        35                  40                  45
```

<210> SEQ ID NO 16
<211> LENGTH: 55
<212> TYPE: PRT
<213> ORGANISM: Mus musculus
<220> FEATURE:
<221> NAME/KEY: MOD_RES -continued

```
<222> LOCATION: (51)..(51)
<223> OTHER INFORMATION: Any amino acid
<220> FEATURE:
<221> NAME/KEY: MOD_RES
<222> LOCATION: (55)..(55)
<223> OTHER INFORMATION: Any amino acid

<400> SEQUENCE: 16

Asn Gln Phe Trp Pro Ser Gly Ser Ser Arg Val Gln Leu Cys Met Ala
1               5                   10                  15

Gln Glu Gly Lys Arg Ser Pro Thr Val Thr Ser Arg Gln Leu Gly Thr
            20                  25                  30

Gly Trp Gly Phe Pro Met Thr Val Ala Ala Pro Ser Val Ile Leu Arg
        35                  40                  45

Lys Thr Xaa Ala Ser Glu Xaa
    50                  55

<210> SEQ ID NO 17
<211> LENGTH: 74
<212> TYPE: PRT
<213> ORGANISM: Mus musculus
<220> FEATURE:
<221> NAME/KEY: MOD_RES
<222> LOCATION: (16)..(17)
<223> OTHER INFORMATION: Any amino acid

<400> SEQUENCE: 17

Thr Pro Tyr Pro Ser Gly Val Ile Arg Leu Thr Ile Gly Arg Ala Xaa
1               5                   10                  15

Xaa Thr Ile Phe Arg Met Ala Arg Val Phe Gln Gln Asp Glu Val Gln
            20                  25                  30

Leu Val Gln Trp Pro Ser Phe Tyr Leu Gly Val Arg Ile Gln Thr Ser
        35                  40                  45

Ser Gln Thr Cys Trp Ala Ser Thr Leu Pro Gly Lys Leu Ser Phe Gln
    50                  55                  60

Ser Leu Asp Arg Gln Phe Leu Phe His Ile
65                  70

<210> SEQ ID NO 18
<211> LENGTH: 36
<212> TYPE: PRT
<213> ORGANISM: Mus musculus

<400> SEQUENCE: 18

Phe Phe Pro Ile Arg Gly Cys Val Phe Ala Asp Gln Ser Val Leu Thr
1               5                   10                  15

Gln Pro Trp Glu Ala Ser Pro Val Ser Cys Ala Leu Pro Gly Arg Cys
            20                  25                  30

Glu Trp Arg Leu
        35

<210> SEQ ID NO 19
<211> LENGTH: 56
<212> TYPE: PRT
<213> ORGANISM: Mus musculus

<400> SEQUENCE: 19

Phe Ser Glu Leu Arg Ile Ser Glu Asp Thr Met Val Gln Pro Gln Leu
1               5                   10                  15

Trp Gly Leu Gln Trp Ala Glu Pro Leu Val Cys Ser Arg Ser Gln Ala
            20                  25                  30
```

```
Gly Cys Arg Ala Ser Ser Ala Gln Ala His Thr Arg Ala Leu Arg Met
            35                  40                  45

Pro Gln Trp Ala Pro Ser Ala Leu
    50                  55

<210> SEQ ID NO 20
<211> LENGTH: 65
<212> TYPE: PRT
<213> ORGANISM: Mus musculus
<220> FEATURE:
<221> NAME/KEY: MOD_RES
<222> LOCATION: (5)..(5)
<223> OTHER INFORMATION: Any amino acid

<400> SEQUENCE: 20

Asn Phe Arg Arg Xaa Ser Val Leu Thr Gln Pro Asp Lys His Thr Gly
1               5                   10                  15

Leu Pro Val Pro Gly His Asp Tyr Pro Ala Ala Asp Leu Asn Asp Gln
            20                  25                  30

Glu Asp Ala His Glu Ser Asp Leu Val Trp Arg Val Ser Ala Trp Pro
            35                  40                  45

Leu Leu Tyr His Leu Lys Val Pro Leu Met Lys Asp Gln Leu Val Ala
    50                  55                  60

Leu
65
```